(12) United States Patent
He et al.

(10) Patent No.: US 7,220,845 B2
(45) Date of Patent: May 22, 2007

(54) NUCLEIC ACID MOLECULES ASSOCIATED WITH PLANT CELL PROLIFERATION AND GROWTH AND USES THEREOF

(75) Inventors: Steve Sichuan He, St. Louis, MO (US); Stanton B. Dotson, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 780 days.

(21) Appl. No.: 10/024,632

(22) Filed: Dec. 19, 2001

(65) Prior Publication Data

US 2002/0170093 A1  Nov. 14, 2002

Related U.S. Application Data

(60) Provisional application No. 60/257,896, filed on Dec. 21, 2000.

(51) Int. Cl.
    *C12N 15/29* (2006.01)
(52) U.S. Cl. .................... 536/23.1; 536/23.6
(58) Field of Classification Search .............. 536/23.1, 536/23.6; 800/278, 298; 435/320.1, 468
    See application file for complete search history.

(56) References Cited

U.S. PATENT DOCUMENTS 6,329,567 B1  12/2001  Jofuku et al.

FOREIGN PATENT DOCUMENTS

| WO | WO0129240 | 4/2001 |
|----|-----------|--------|
| WO | WO0136595 | 5/2001 |

OTHER PUBLICATIONS

Bowie et al, Science 247:1306-1310, 1990.*
McConnell et al, Nature 411 (6838):709-713, 2001.*
Lazar et al (1988, Mol. Cell. Biol. 8:1247-1252).*
Hill et al (1998, Biochem. Biophys. Res. Comm. 244:573-577).*
Fourgoux-Nicol et al (1999, Plant Molecular Biology 40 :857-872).*
Kano-Murakami et al (1993, FEBS 334:365-368).*
Elliot et al (1996, The Plant Cell 8:155-168).*
Wilson, et al., DNA binding properties of the *Arabidopsis* floral development protein *AINTEGUMENTA*, Nucleic Acids Research 28:4076-4082, 2000.

Krizek, Ectopic expression of *AINTEGUMENTA* in *Arabidopsis* plants results in increased growth of floral organs, Developmental Genetics 25:224-236, 1999.
Mizukami, et al., Plant organ size control : *AINTEGUMENTA* regulates growth and cell numbers during organogenesis, Proceedings of the National Academy of Sciences, USA 97:942-947, 2000.
Okamura, et al., The AP2 domain of *APETALA2* defines a large new family of DNA binding proteins in *Arabidopsis*, Proceedings of the National Academy of Sciences, USA 94:7076-7081, 1997.
Mian, et al., RFLP tagging of QTLs conditioning specific leaf weight and leaf size in soybean, Theor Appl Genet 96: 354-360, 1998.
Klucher, et al, The *AINTEGUMENTA* gene of *Arabidopsis* required for ovule and female gametophyte development is realted to the floral homeotic gene *APETALA2*, The Plant Cell 8:137-153, 1996.
Gu, et al., The *Fruitfull* Mads-box gene mediates cell differentiation during *Arabidopsis* development, Development 125:1509-1517, 1998.
Liu, et al., Transcription factors and their genes in higher plants, European Journal of Biochemistry 262:247-257, 1999.
Long, et al., The developmental of apical embryonic pattern in *Arabidopsis*, Development 125 :3027-3035, 1998.
Schneitz, et al., Pattern formation and growth during floral organogenesis : *HUELLENLOS* and *AINTEGUMENTA* are required for the formation of the proximal region of the ovule primordium in *Arabidopsis thalania*, Development 125:2555-2563.
Elliot, et al., *AINTEGUMENTA*, an *APETALA2*-like gene of *arabidopsis* with pleiotropic roles in ovule development and floral organ growth, The Plant Cell 8:155-168, 1996.
Long, et al., Initiation of Axillary and Floral meristems in *Arabidopsis*, Developmental Biology 218 :341-353, 2000.

* cited by examiner

*Primary Examiner*—Stuart F. Baum
(74) *Attorney, Agent, or Firm*—Matthew L. Madsen; Howrey LLP

(57) ABSTRACT

The present invention provides a gene encoding ANT-like polypeptide comprising in the N-terminal to C-terminal direction two AP2 DNA binding domains followed in the C-terminal by an amino acid subsequence selected from the group consisting of Xaa-Ser-Ser-Ser-Arg-Glu, Xaa-Ser-Asn-Ser-Arg-Glu, and Asn-Ser-Ser-Ser-Arg-Asn, wherein Xaa is an amino acid residue selected from the group consisting of Gly, Ala, Val, Leu, and Ile. Such gene encoding ANT-like polypeptide can be over-expressed in a transgenic plant to provide agronomically desired traits based on increased size of selected plant organs.

3 Claims, 18 Drawing Sheets

Figure 1

```
         1                                                                              50
GmANT1  MKRINESNNT DDGNNHNWLG FSLSPHM... .....KMEAT SAATVPTTFY
GmANT2  MKSMENDDNA DLNNQNNWLG FSLSPQMHNI GVSSHSQPSS AAEVVPTSFY
   ANT  MKSFCDNDDN NHSNTTNLLG FSLSSNMMKM GGRGGREAIY SSSTSSAATS 51                                                                             100
GmANT1  MSPSQSHL.. .....SNFGMC YGV.GENGNF HSPLTVMPLK SDGSLCILEA
GmANT2  HHTAP..L.. .....SSYGFY YGLEAENVGL YSALPIMPLK SDGSLYGLET
   ANT  SSSVPPQLVV GDNTSNFGVC YG..SNPNGGI YSHMSVMPLR SDGSLCLMEA 101                                                                            150
GmANT1  LKRSQTQVMV PTSSPKLEDF LGGATMGT.H EY...GSHER GLSLDSIYYN
GmANT2  LSRSQAQAMA TTSTPKLENF LGGEAMGTPH HYECSATETM PLSLDSVFY.
   ANT  LNRSSHSNHH QDSSPKVEDF FG......TH HNNTSHKEAM DLSLDSLFYN 151                                                                            200
GmANT1  SQNAEAQPNR DLLSQPFRQ. ....QGHMSV QTHPYYSGLA CHGLYQAPLE
GmANT2  IQPSRRDENN NQTYQNHVQH ISTNQQQQQQ ELQAYYSTLR NHDMILEGSK
   ANT  ..TTHEPNT TTNFQEFPSF PQTRNHEEET RNYGNDPSL. THG........

201                                                                            250
GmANT1  EETTKET... HVSDCSSLMP QMTEGLKNWV APTREF.STH QQVLEQQMNC
GmANT2  QSQTSDNNNL HVQNMGDDA VPVPGLKSW. .EVRNFQASH AHESKMIVPH
   ANT  ...GSFNVGV YGEFQQSLSL SMSPGSQSSC .....ITGSH HHQONQNQNH 251                                                                            300
GmANT1  GMGNERNGVS LGSVGCGELQ SLSLSMSPGS QSSCVT..... .APSGTDSVA
GmANT2  VEERNAGESGS IGSMAYGDLQ SLSLSMSPSS QSSSVTSSHR ASPAVVDSVA
   ANT  QSQNH...... ..........Q QISEALVETS VGFEIT..... .......TMA 301                                                                            350
GmANT1  VDAKKRGHAK ...LGQKQPV HRKSIDTFGQ RTSQYRGVTR HRWTGRYEAH
GmANT2  MDTKKRGPEK ...VDQKQIV HRKSIDTFGQ RTSQYRGVTR HRWTGRYEAH
   ANT  AAKKRGQED VVVVGQKQIV HRKSIDTFGQ RTSQYRGVTR HRWTGRYEAH 351                                                                            400
GmANT1  LWDNSCKKEG QTRKGRQVYL GGYDMEEKAA RAYDLAALKY WGPSTHINFS
GmANT2  LWDNSCKKEG QSRKGRQVYL GGYDMEEKAA RAYDLAALKY WGPSTHINFP
   ANT  LWDNSFKKEG HSRKGRQVYL GGYDMEEKAA RAYDLAALKY WGPSTHTNFS 401                                                                            450
GmANT1  IENYQVQLEE MKNMSRQEYV AHLRRKSSGF SRGASIYRGV TRHHQHGRWQ
GmANT2  LENYQNELEE MKNMTRQEYV AHLRRKSSGF SRGASMYRGV TRHHQHGRWQ
   ANT  AENYQKEIED MKNMTRQEYV AHLRRKSSGF SRGASIYRGV TRHHQHGRWQ 451                                                                            500
GmANT1  ARIGRVAGNK DLYLGTFSTQ EEAAEAYDVA AIKFRGANAV TNFDISRYDV
GmANT2  ARIGRVAGNK DLYLGTFSTQ EEAAEAYDIA AIKFRGANAV TNFDITRYDV
   ANT  ARIGRVAGNK DLYLGTFGTQ EEAAEAYDVA AIKFRGTNAV TNFDITRYDV 501                                                                            550
GmANT1  ERIMASSNLL AGELARRKKD NDPRNKDIDY NKSVVTSV.N NEETVQVQAG
GmANT2  EKIMASSNLL SSELARRNRE TDNETQCIDQ NHNKPSAYED TQEAILMHQK
   ANT  DRIMSSNTLL SGELARRN.. ...NNSIVVR NTEDQTALNA VVEGGSNKEV 551                                                                            600
GmANT1  NNNNENDSEW KMVLFNHPSQ QQ.QANGNGS DQKIMNCGNY RNSAFSMALQ
GmANT2  SCESEND.QW KMVLY.QSSQ QL.EQNPPTI E......SDR TNQSFAVALD
   ANT  STPERLLSFP AIFALPQVNQ KMFGSNMGGN MSPWTSNPNA ELKTVALTLP 601                                                                            650
GmANT1  DLIGIDSVGS GQHNMLDESS KIGTHFSNTS SLVTSLSSSR EASPEKRGPS
GmANT2  NMF....... .HQEVEESS KARTHVSNPS SLATSLSSSR EGSPDRTSLP
   ANT  QMPVFAAWAD S-------- ---------- ---------- ----------

651                                                                            700
GmANT1  LLFPMPEMET KIVNPIGTSV TSWLPSPTVQ MRPSPAISLS HLPVFASWTD
GmANT2  MLSGMPSTAS KLLATNPNNV NSWDPSPHLR ....PALTLP QMPVFAAWTD
   ANT  ---------- ---------- ---------- ---------- ----------

701
GmANT1  T
GmANT2  A
   ANT  -
```

Figure 2

```
g1244708    1  ----------------MKSFCDNDDNNHSNTTNLIGFSLSSNMKMGGRGREAIY-----------------  40
GmANT1      1  ----------------MKRINESNNTDDGNNHNMIGFSLGP-HKMEA-------------------------  31
OsANT2      1  MASGNSSSSGSMAATAGGVGGWIGFSLSP-HMATYCAGGVDDVG-HHHH-----------------------  48
GhANT1      1  ----------------MSNWIGFSLTP-DLRIDESFGREDHGGFP--------------------------  28
GmANT2      1  ----------MKSMENDDNADLNNQNWIGFSLSPQMHHNIGVSSHSQPSSAAEVVPTSFYHHTAPLSSYGFYY  63
OsANT1      1  -----------------MASGGGSNMIGFSLSPHMPAMEVPSSSEPSTAAHHH-----HHHHPPAA------  45 g1244708   41  ----------------SSSTSSAATSSSSVPPQLMVGDNTSNFGVCYGSNPNGG-----IYSHMSV-----  85
GmANT1     32  ----------------TSAATVPTTFYMSPSQ-----SHLSNFGMCYGVGENGN-----FHSPLTV-----  71
OsANT2     49  HHVHQHQQHGGGGLEYN--PAAVASSFYYGGGHDAVVTSAAGGGSYYGAGFSS------------------  99
GhANT1     29  GLEAENVGLYSALP---------------------------------------------------SV----  30
GmANT2     64  --AAAGAMSSPP------------------------------------------------------II----  78
OsANT1     46  DSATTCNFLESPPAAQMVAPSPGYYYVGGAYGDGTSTAGVYY--SHLPM----------------------  103 g1244708   86  MPLRSDGSLCLMEALNRS---------SHSNHHQDS-SPKVEDFFG--THHN-------------------  125
GmANT1     72  MPLKSDGSLCILEALKRS---------QTQVMVPTS-SPKIEDFLGATMGT-------------------  113
OsANT2    100  MPLRSDGSLCIMEALRGG---------DQEQQGVVVSASPKLIEDFLG---------------------  137
GhANT1     31  MPLRSDGSLCVVDPFRRSIAADEDWRYENGIGSATANEQGPKLIEDFLGCYSNPSQETKAYCGTHEN----  98
GmANT2     79  MPLKSDGSLYGLETLSRS---------QAQAMATTS-TPKLMENFLGEAMGTPHHYECSATETMP-----  133
OsANT1    104  MPIKSDGSLCIMEGMMPS---------S-SPKLEDFLG-------------------------------  131 g1244708  126  ----------------NTSHKEAMDLSLDSLFYN----TTHEPNTTTNFQEFFS------------------  159
GmANT1    114  ----------------HEYGSHERGLSLDSIYNSQNAEAQPNRDLLSQPFRQQGHMSVQT-----------  158
OsANT2    138  ----------------AGPAMALSLDNSAFYYGGHGHQGHAQDGGAVGGDPHHGG---------------  177
GhANT1     99  QNTVPSPTRINVNAPNYNSSSGD---AEAAENFLNPSSFIQTYRNYNENPQTLMAGG--------------  152
GmANT2    134  LSLDSVFYIQPSRRDPNNNQTY----QNHVQHISTNQQQQQELQAYYSTLRNHDMILE-------------  188
OsANT1    132  ----------------CGNGSGHDPATMYSQGQEAEDASRAAYQHHQLVP---------------------  165 g1244708  160  ----------FPQTRNHEEETRN-YGND-------PSLTHGGSFNVGVYGEF----QQSLSLSMSPGS---  205
GmANT1    159  HPYYSGLACHGLYAPVLEEETTKETHVSDCSSLMPQMTEGLKNWVAPTREFSTHQQVLEQQMNCQMGN---  226
OsANT2    178  ----GGFLQCAVIPGAGAG-----HD-------AALVHDQSAAVAAGWAAMHGGGYDIANAAADDV----  228
GhANT1    153  ----HSLQQCDPNPNHNQR-----SG-------VHHVPFESATSVSGFKSWLRQTPFPGGKASGN-----  201
GmANT2    189  -GSKQSQTSDNNNLHVQNMG-GDDAVPVPGLKSWJEVRNFQASHAHESKMIVPHVEENAG-----------  245
OsANT1    166  YNYQPLTEAEMLQEARARP-MEDAMAAA--KNFLVTSYGACYGNQ-EMPQPLSLSMSP-----------  219 g1244708  206  -QSSCITGSHHHQNQMQHQSQNHQQISEALVETSVGFETTTMAAAKKKRGQEDVVVGQKQIVHRK------  272
GmANT1    227  ERNGVSLGSVGCGELQSLSLSMSPGSQSQSSCVTAPS---GTDSVAVDAKKRGH--AKLGKKQPVHRK---  287
OsANT2    229  CAAGPIIPTGGHLHPLTLSMSSAGSQSCVTVQAAAAGEPYMAMDAVSKKRGG--ADRAGQKQPVHRK----  294
GhANT1    202  -ETNNNFNFQALSLTMS---PTSRNGFPAIAP-----LEVVDNRKRP--VGKNLTRESVPRK--------  252
GmANT2    246  ESGSIGSMAYGDLQSLSLSMSPS-SQSSVTSSHRASPAVVDSVAMDTKKRGP--EKVDKKIVHRK------  309
OsANT1    220  GSQSSCVSAAPQQHQQMAVVAA-AAAGDGQGSNDGGEQRVG----GKGGQKQPVHRKT------------  280
```

US 7,220,845 B2

NUCLEIC ACID MOLECULES ASSOCIATED WITH PLANT CELL PROLIFERATION AND GROWTH AND USES THEREOF

CROSS-REFERENCE TO RELATED APPLICATIONS

This application claims priority under 35 U.S.C. § 119(e) of U.S. Provisional Application Ser. No. 60/257,896 filed on Dec. 21, 2000, the disclosures of which application is incorporated herein by reference in its entirety.

INCORPORATION OF SEQUENCE LISTING

This application contains a sequence listing, which is contained on three identical CD-ROMs: two copies of a sequence listing (Copy 1 and Copy 2) and a sequence listing Computer Readable Form (CRF), all of which are herein incorporated by reference. All three CD-ROMs each contain one file called "Ant.51837-B.txt" which is 87,009 bytes in size and was created on Dec. 17, 2001.

FIELD OF THE INVENTION

Described herein are inventions in the field of plant molecular biology and plant genetic engineering, including isolated nucleic acid molecules encoding AINTEGUMENTA-like (ANT-like) polypeptides that are useful in improving agronomic, horticultural and quality traits of plants. In addition, polypeptides so encoded and antibodies capable of binding the polypeptides are encompassed by the present invention. The present invention also relates to methods of identifying and isolating nucleic acid molecules encoding ANT-like polypeptides. Also disclosed are polypeptides, antibodies, recombinant DNA constructs, transgenic plants characterized by the increased size of plant organs, methods for making and using the nucleic acid molecules, polypeptides, antibodies, and recombinant DNA constructs.

BACKGROUND OF THE INVENTION

One of the goals of plant genetic engineering is to produce plants with agronomically, horticulturally or economically important characteristics or traits. Traits of particular interest include high yield, improved quality and high stability. Although the yield from a plant is influenced greatly by external environmental factors, it appears that the yield of the plant is determined, in part, by the intrinsic size of various organs/tissues (such as seeds, fruits, roots, leaves, tubers, stems, and bulbs) which are in turn determined by internal developmental factors. Enhancement of the yield of a plant may be achieved by genetically modifying the plant so that the intrinsic size of plant organs is increased.

Plants have unique developmental features that distinguish them from other eukaryotes. Plant cells do not undergo migration. It is thus believed that cell division and cell expansion are the predominant mechanisms by which the number and position of organ primordia are determined and also by which the intrinsic size and shape of each of plant organs are controlled. It is also believed that there are developmental regulators that control cell proliferation and growth and intrinsic size of plant organs. When interacting with external environmental factors, the developmental regulators determine the eventual size of plant organs. Therefore, identification/isolation of developmental regulators that control cell proliferation and growth and the intrinsic size of organs would be desirable. Such developmental regulators could be used in the genetic engineering to produce transgenic plants having increased intrinsic size of organs of interest and subsequently higher yield.

Gu et al.(*Development* 125:1509–1517 (1998)) recently reported that the *Arabidopsis* AGL8 gene, a MADS-box gene, might be involved in mediating cell differentiation in *Arabidopsis* plants during fruit and leaf development. Like AGAMOUS and other plant MADS-box genes, AGL8 encodes a polypeptide of about 260 amino acids including a highly conserved DNA-binding MADS domain of about 56 amino acids (Riechmann and Meyerowitz, *Biol. Chem.* 378:1079–1101 (1997)). They also reported that the ectopic expression of the AGL8 gene under control of a constitutive promoter in *Arabidopsis* plants could increase the size of seeds and fruits and delay senescence in the transgenic *Arabidopsis* plants (WO 99/00503).

The *Arabidopsis* APETALA2 (AP2) gene has recently been shown to be able to control seed mass in transgenic *Arabidopsis* and tobacco plants (WO 97/14659). The AP2 polypeptide contains two tandemly repeated 68-amino acid motifs designated as AP2 DNA binding domain (Jofuku, et al., *Plant Cell* 6:1211–1225 (1994), which are homologous to the DNA binding domain of ethylene response element binding polypeptides. Several studies suggested that the AP2 gene is a homeotic gene which controls three processes during flower development in *Arabidopsis* plants: (1) the establishment of flower meristem identity (Irish and Sussex, *Plant cell* 2:741–753 (1990); Bowman et al., *Development* 119:721–743 (1993)); (2) the specification of flower organ identity and regulation of floral organogenesis (Komaki et al., *Development* 104:195–203 (1988); Bowman et al., *Plant Cell* 1:37–42 (1989); Bowman et al., *Development* 112:1–20 (1991); Kunst et al., *Plant Cell* 1:1195–1208 (1989); Jofuku et al., *Plant Cell* 6:1211–1225 (1994)); and (3) the temporal and spatial regulation of flower homeotic gene activity (Drews et al., *Cell* 65:991–1002 (1991)). Genetic studies have shown that AP2 gene is also required for normal ovule and seed development (Jofuku et al., *Plant Cell* 6:1211–1225 (1994); Leon-Kloosterziel et al., *Plant Cell* 6:385–392 (1994); and Modrusan et al., *Plant Cell* 6:339–349 (1994)). Transgenic *Arabidopsis* plants, where the AP2 gene was expressed in the antisense orientation under the control of the cauliflower mosaic virus 35S constitutive promoter, produced seed with increased mass and total protein and fatty acid contents (WO 97/14659). *Arabidopsis* and tobacco transgenic plants, where the AP2 gene was overexpressed in the sense orientation under control of the cauliflower mosaic virus 35S constitutive promoter, produced seed with decreased mass and decreased total protein content (WO 97/14659).

It has been shown by two recent studies that the AINTEGUMENTA (ANT) gene of *Arabidopsis* might play a role in regulating cell growth and cell numbers during organogenesis (Mizukami and Fisher, *Proc. Natl. Acad. Sci. USA* 97:942–947 (2000); Krizek, *Develop. Genet.* 25:224–236 (1999)). The ANT gene belongs to the large AP2 gene family and encodes a transcription factor that may play a critical role in regulating ovule and female gametophyte development (Klucher et al., *Plant Cell* 8:137–153 (1996); Elliott et al., *Plant Cell* 8:155–168 (1996)). In one study (Mizukami and Fisher, *Proc. Natl. Acad. Sci. USA* 97:942–947 (2000)), it was reported that when the ANT gene was ectopically expressed in *Arabidopsis* plants under the control of a cauliflower mosaic virus 35S constitutive promoter, the leaves, stems, pedicels, sepals, petals, stamens, gynocia, ovules, and fruits of the transgenic plants were dramatically enlarged without altering their superficial morphology. Mass of leaves and flowers was increased as much as three times over those in control plants, due to the ectopic expression of the ANT gene. Ectopic expression of the ANT gene in tobacco plant also resulted in organs of increased size comparing to wild type. However, the transgenic plants containing a 35S/ANT expression construct were male sterile and most transgenic plants containing a 35S/ANT expression construct were also female sterile. Only T1 plants expressing relatively low levels of the ANT gene could generate seeds when pollinated by hand with wild-type pollen. In the other study, Krizek (Krizek, *Develop. Genet.* 25:224–236 (1999)) reported that ectopic expression of the ANT gene under the control of a cauliflower mosaic virus 35S constitutive promoter produced larger floral organs without altering the number and shape of these organs. The transgenic plants containing a 35S/ANT expression construct were male sterile and showed severe reduction in female fertility. Krizek did not observe the increased size of vegetative organs.

No DNAs encoding ANT-like polypeptides in other plants, especially corn, soybean, rice and cotton, have been isolated, sequenced or functionally characterized. Considering that the complex nature of organ size control in plants and that the genetic basis for plant interspecies diversity of phenotype might be minor changes in the structure or expression of orthologous regulatory genes (Doebley and Lukens, *Plant Cell* 10:1075–1082 (1998); Somerville and Somerville, *Science* 285:380–383 (1999)), there is a great deal of interest in identifying in plants the genes that, like ANT gene, may be used to control the intrinsic organ size of plants when ectopically expressed in plant cells and subsequently enhance the economic yield of plants.

SUMMARY OF THE INVENTION

The present invention, in one aspect, provides an isolated nucleic acid molecule comprising a nucleotide sequence or complement thereof, wherein the nucleotide sequence encodes an ANT-like polypeptide having in the N-terminal to C-terminal direction two AP2 DNA binding domains followed in the C-terminal by an amino acid subsequence selected from the group consisting of Xaa-Ser-Ser-Ser-Arg-Glu, (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue having an aliphatic side chain and selected from the group consisting of Gly, Ala, Val, Leu, and Ile.

The present invention, in another aspect, provides an isolated nucleic acid molecule comprising: (1) a nucleotide sequence which encodes a polypeptide having an amino acid sequence that has at least 60% sequence identity to a sequence selected from the group consisting of SEQ ID Nos: 2, 4, 6, 9, 11, and 13; (2) a nucleotide sequence which hybridizes under stringent conditions to the complement of a second nucleotide sequence which encodes a polypeptide having an amino acid sequence selected from the group consisting of SEQ ID Nos: 2, 4, 6, 9, 11, and 13; (3) a nucleotide sequence which has at least 60% sequence identity to a member selected from the group consisting of SEQ ID Nos: 1, 3, 5, 7, 8, 10, and 12; or (4) a nucleotide sequence which is complementary to (1), (2), or (3).

The isolated nucleic acid molecules of the present invention may further comprise an operably linked promoter or partial promoter region. The promoter can be a constitutive promoter, an inducible promoter or a tissue-specific promoter. The constitutive promoter can be, for example, a cauliflower mosaic virus (CaMV) 35S promoter (U.S. Pat. Nos. 5,858,742 and 5,352,605) or the rice actin (RACT1) promoter (U.S. Pat. No. 5,641,876). The tissue-specific promoter can be active in vegetative tissue or reproductive tissue. The tissue-specific promoter active in reproductive tissue can be a seed-specific promoter. The tissue-specific promoter active in vegetative tissue can be a root-specific, shoot-specific, meristem-specific or leaf-specific promoter. The isolated nucleic acid molecule of the present invention can still further comprise a 5' non-translated sequence, 3' non-translated sequence, introns, or the combination thereof.

The present invention also provides a method for obtaining an isolated nucleic acid molecule encoding all or a substantial portion of the amino acid sequence of an ANT-like polypeptide, the method comprising the steps of: (a) probing a cDNA or genomic library with a hybridization probe comprising a nucleotide sequence encoding all or a portion of the amino acid sequence of a polypeptide, wherein the amino acid sequence of the polypeptide is selected from the group consisting of SEQ ID Nos: 2, 4, 6, 9, 11, and 13; (b) identifying a DNA clone that hybridizes under stringent conditions to hybridization probe; (c) isolating the DNA clone identified in step (b); and (d) sequencing the cDNA insert or genomic fragment contained in the DNA clone isolated in step (c) wherein the sequenced nucleic acid molecule encodes all or a substantial portion of the amino acid sequence of the ANT-like polypeptide.

The present invention also further provides a method for obtaining a nucleic acid molecule encoding all or a substantial portion of the amino acid sequence of an ANT-like polypeptide comprising: (a) synthesizing a first and a second oligonucleotide primers, wherein the sequences of the first and second oligonucleotide primers encode two different portions of a polypeptide having an amino acid sequence selected from the group consisting of SEQ ID Nos: 2, 4, 6, 9, 11, and 13; and (b) amplifying and obtaining the nucleic acid molecule directly from mRNA samples, from genomic libraries or from cDNA libraries using the first and second oligonucleotide primers of step (a) wherein the nucleic acid molecule encodes all or a substantial portion of the amino acid sequence of the ANT-like polypeptide.

The present invention, in another aspect, provides a substantially purified polypeptide the amino acid sequence of which: (1) comprises in the N-terminal to C-terminal direction two AP2 DNA binding domains followed in the C-terminal by an amino acid subsequence selected from group consisting of Xaa-Ser-Ser-Ser-Arg-Glu, (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue having an aliphatic side chain and selected from the group consisting of Gly, Ala, Val, Leu, and Ile; (2) is encoded by a first nucleotide sequence which specifically hybridizes under stringent conditions to the complement of a second nucleotide sequence selected from the groups consisting of SEQ ID NO: 1, 3, 5, 7, 8, 10, and 12; (3) is encoded by a third nucleotide sequence that has at least 60% sequence identity to a member selected from the group consisting of SEQ ID NOs: 1, 3, 5, 7, 8, 10, and 12; or (4) has at least 60% sequence identity to a member selected from the group consisting of SEQ ID Nos: 2, 4, 6, 9, 11, and 13.

The present invention, in another aspect, provides antibodies that specifically bind to the ANT-like polypeptides of the present invention and recombinant DNA constructs that comprise nucleic acid molecules encoding the ANT-like polypeptides of the present invention.

The present invention also provides a transformed plant comprising in its genome an isolated nucleic acid molecule which comprises: (A) a 5' non-coding sequence which functions in the cell to cause the production of an mRNA molecule; which is operably linked to (B) a structural nucleotide sequence, wherein the structural nucleotide sequence encodes a polypeptide the amino acid sequence of which has at least 60% sequence identity to a member selected from group consisting of SEQ ID NOs: 2, 4, 6, 9, 11, and 13; which is operably linked to (C) a 3' non-translated sequence that functions in said cell to cause termination of transcription.

The present invention also provides a method for increasing the size of one or more plant organs of a plant by expressing ectopically a nucleic acid molecule that encode a polypeptide the amino acid sequence of which has at least 60% sequence identity to a member selected from the group consisting of SEQ ID NOs: 2, 4, 6, 9, 11, and 13 or comprises in the N-terminal to C-terminal direction two AP2 DNA binding domains followed in the C-terminal by an amino acid subsequence selected from group consisting of Xaa-Ser-Ser-Ser-Arg-Glu (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue having an aliphatic side chain and selected from the group consisting of Gly, Ala, Val, Leu, and Ile. The method of the present invention for increasing the size of one or more plant organs of a plant comprises the steps of: (a) inserting into the genome of a plant an exogenous nucleic acid molecule comprising in the 5' to 3' direction and operably linked, (i) a promoter that functions in the cells of a selected plant tissue, (ii) a structural nucleotide sequence that causes the production of an ANT-like polypeptide the amino acid sequence of which has at least 60% sequence identity to a member selected from the group consisting of SEQ ID Nos: 2, 4, 6, 9, 11, and 13, or comprises in the N-terminal to C-terminal direction two AP2 DNA binding domains followed in the C-terminal by an amino acid subsequence selected from group consisting of Xaa-Ser-Ser-Ser-Arg-Glu (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue having an aliphatic side chain and selected from the group consisting of Gly, Ala, Val, Leu, and Ile, and (iii) a 3' non-translated nucleotide sequence that functions in plant cells to cause transcriptional termination and the addition of polyadenylated nucleotides to the 3' end of a RNA sequence; (b) obtaining transformed plant cells containing the exogenous nucleic acid molecule of step (a); and (c) regenerating from the transformed plant cells a transformed plant that ectopically expresses the ANT-like polypeptide in the plant cells. The exogenous nucleic acid molecule may optionally include introns, 5' untranslated leader sequences or other nucleotide sequences designed to enhance transcription and/or translation.

The present invention further provides a plant tissue, such as a seed, which is derived from a transformed plant of the present invention.

The present invention also further provides a method for selecting a plant having increased size of plant organs, said method comprising the steps of: (A) obtaining genomic DNA from a plurality of plants; (B) analyzing genomic DNA from each of the plurality of plants to determine the presence or absence of a DNA marker that is genetically linked to a nucleotide sequence complementary to a nucleotide sequence selected from the group consisting of SEQ ID NOS: 1, 3, 5, 7, 10, and 12 or complements thereof; and (C) selecting said plant containing said DNA marker.

The present invention also provides for the expression of ANT molecules in corn plants. Specifically it provides for the expression of *Arabidopsis* ANT molecules in corn plants under the SSU1A promoter and the pox1 promoter.

BRIEF DESCRIPTION OF THE FIGURES AND SEQUENCE LISTINGS

FIG. 1 shows a comparison of the amino acid sequences of the *Arabidopsis* ANT and two soybean ANT-like polypeptides. The amino acid sequences were aligned using Window32 MegAlign™ 4.00 expert sequence analysis software from DNASTAR, Inc. (Madison, Wis.) using the set of default parameters (Gap Penalty: 11; Gap Length Penalty: 3; Ktuple: 2), based on Hein's method (Hein, Methods Mol. Biol. 25:349–364 (1994)). (SEQ ID NOS 2, 4 & 34 are disclosed respectively in order of appearance).

FIG. 2 shows a comparison of the amino acid sequences of the *Arabidopsis* ANT and soybean, rice, cotton and corn ANT-like polypeptides (gl244708 disclosed as residues 1–551 of SEQ ID NO: 34; GmANT1 disclosed as residues 1–659 of SEQ ID NO: 2; OsANT1 disclosed as residues 1–665 of SEQ ID NO: 9; GhANT1 disclosed as residues 1–582 of SEQ ID NO: 11; ZmANT1 disclosed as residues 6–251 of SEQ ID NO: 13; GmANT2 disclosed as residues 1–661 of SEQ ID NO: 4; OsANT1 disclosed as residues 1–638 of SEQ ID NO: 6).

Figure 3:
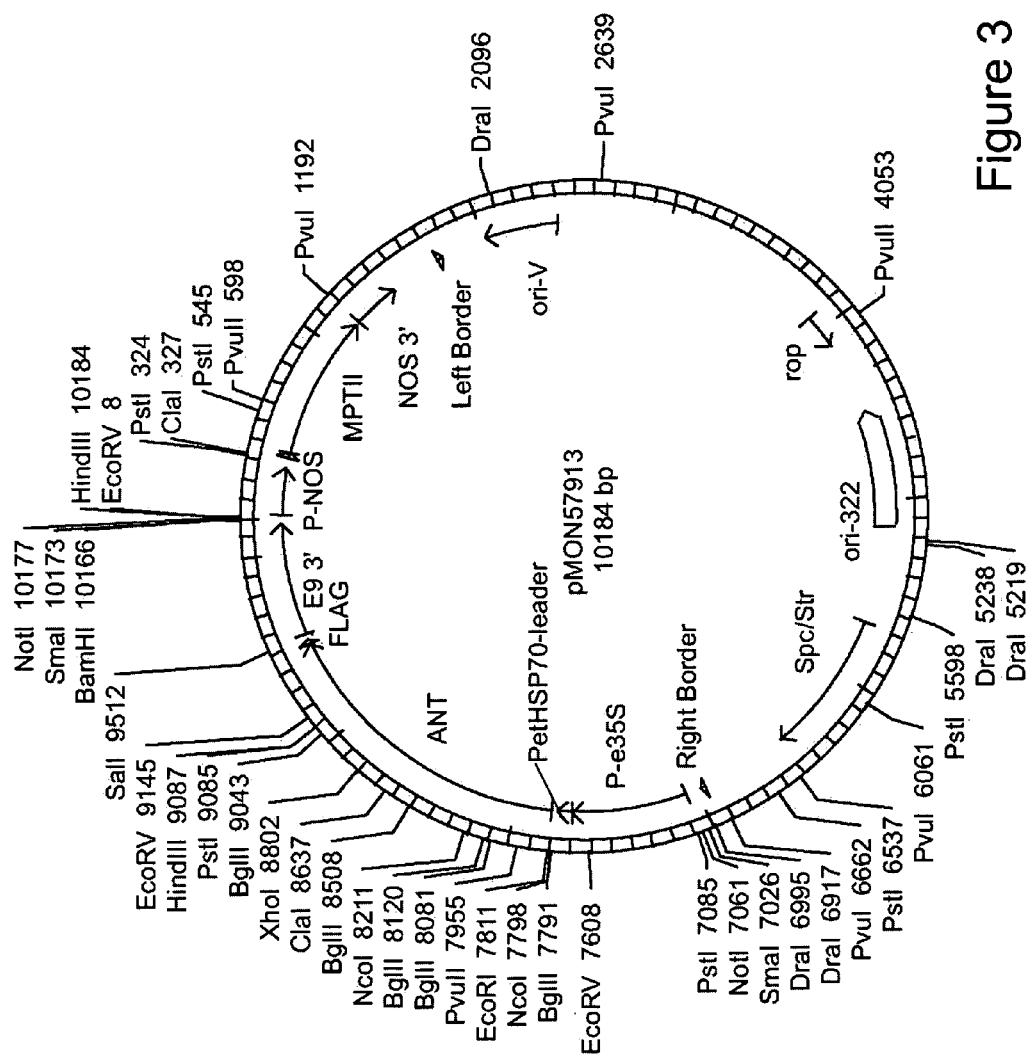
FIG. 3 shows a plasmid map for plant transformation vector pMON57913.
Figure 4:
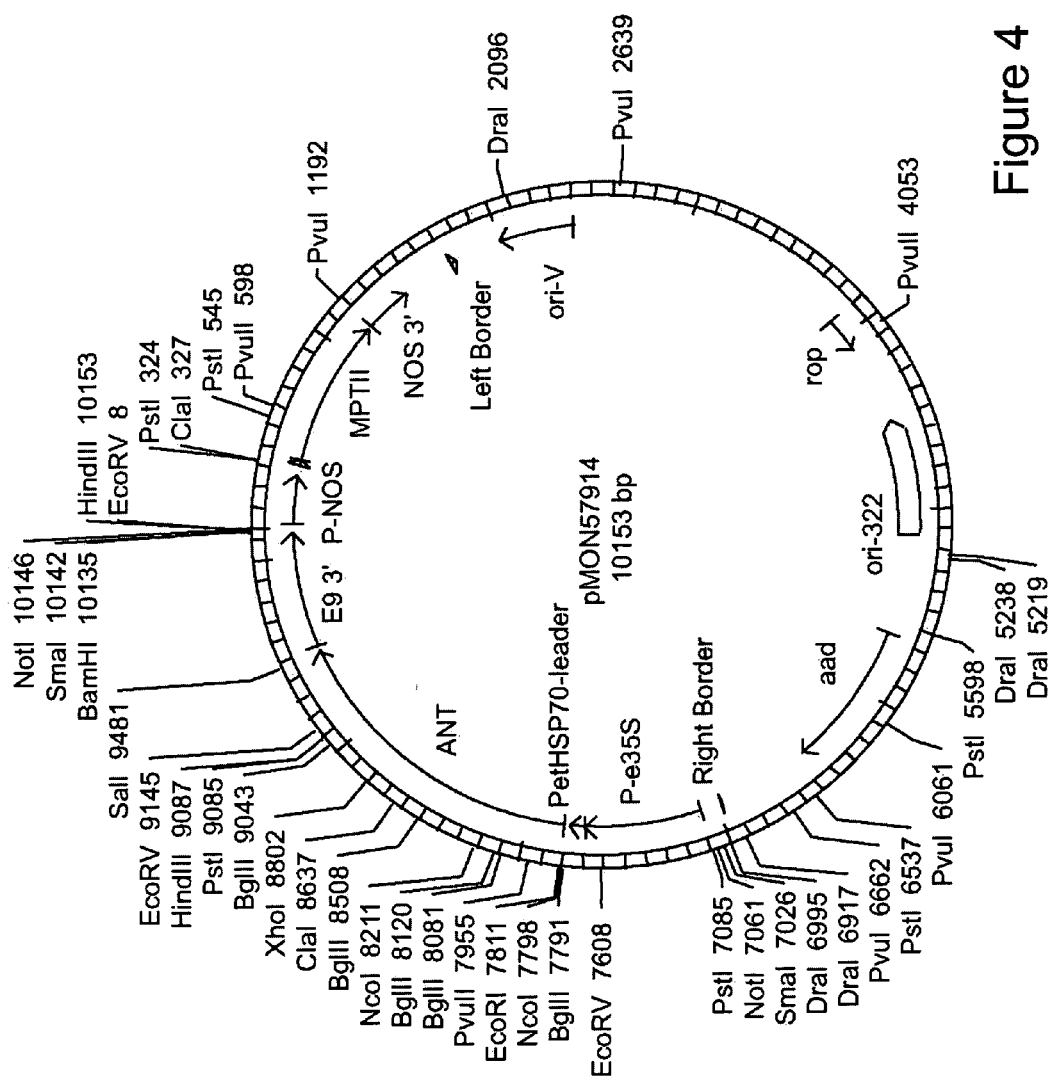
FIG. 4 shows a plasmid map for plant transformation vector pMON57914.
Figure 5:
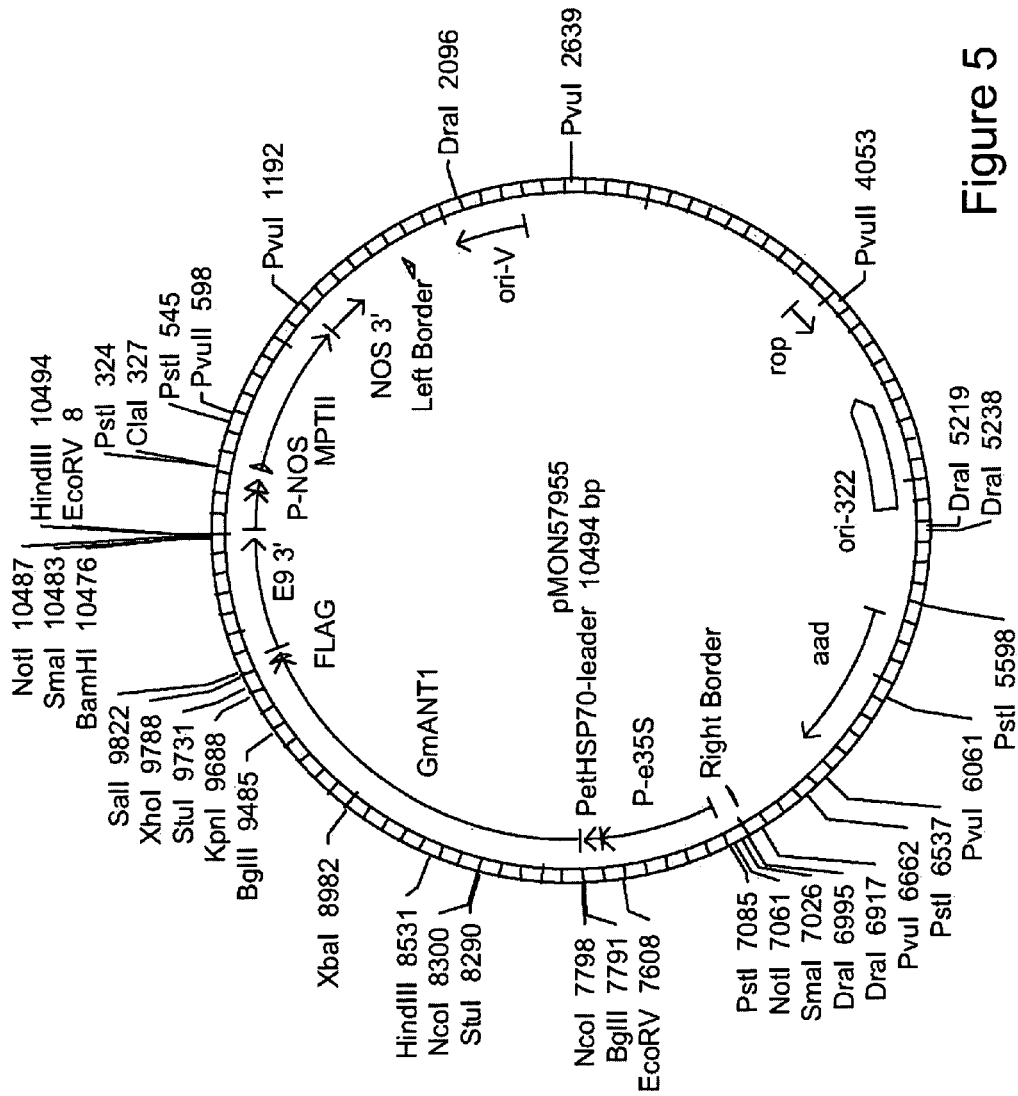
FIG. 5 shows a plasmid map for plant transformation vector pMON57955.
Figure 6:
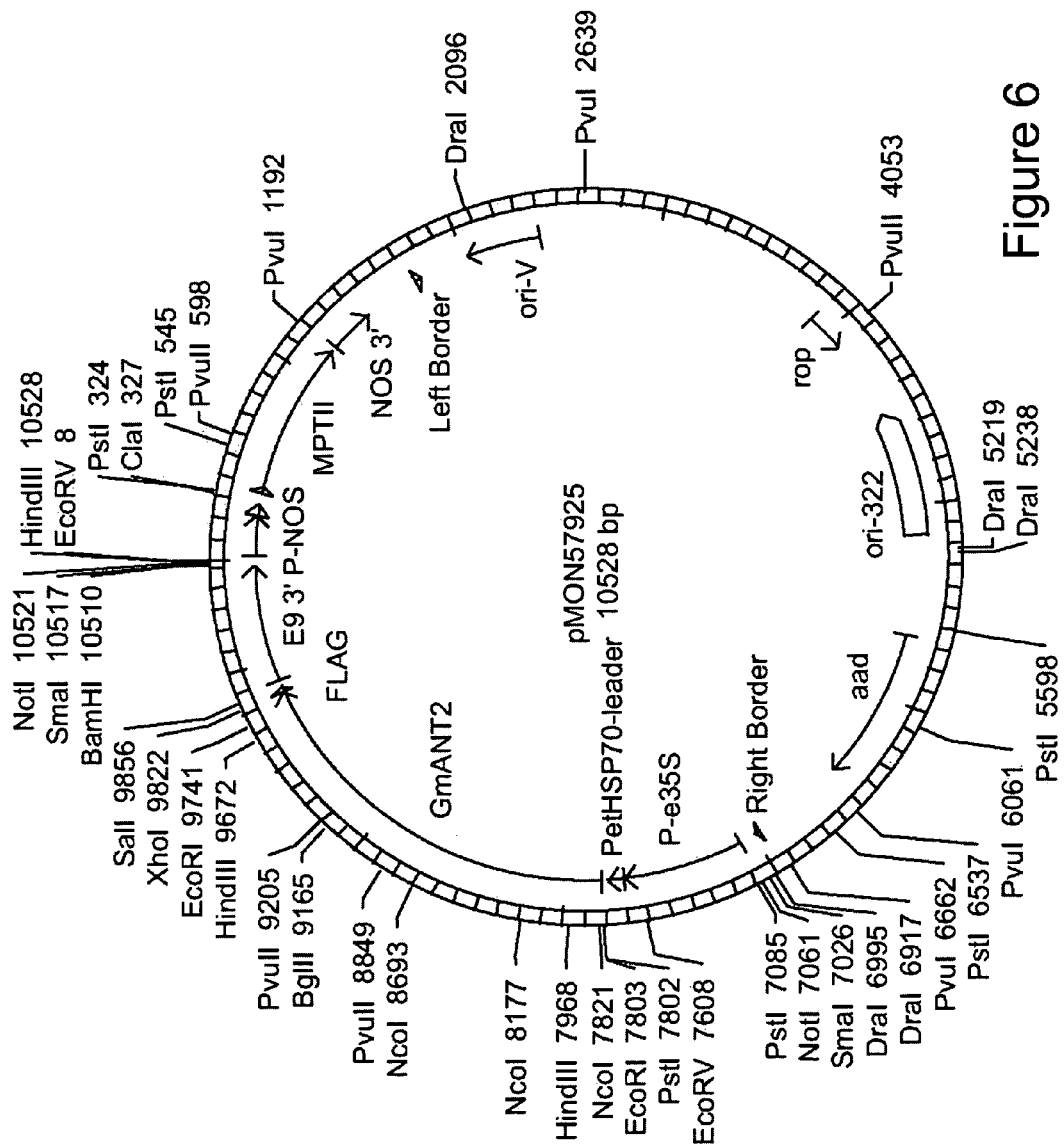
FIG. 6 shows a plasmid map for plant transformation vector pMON57925.
Figure 7:
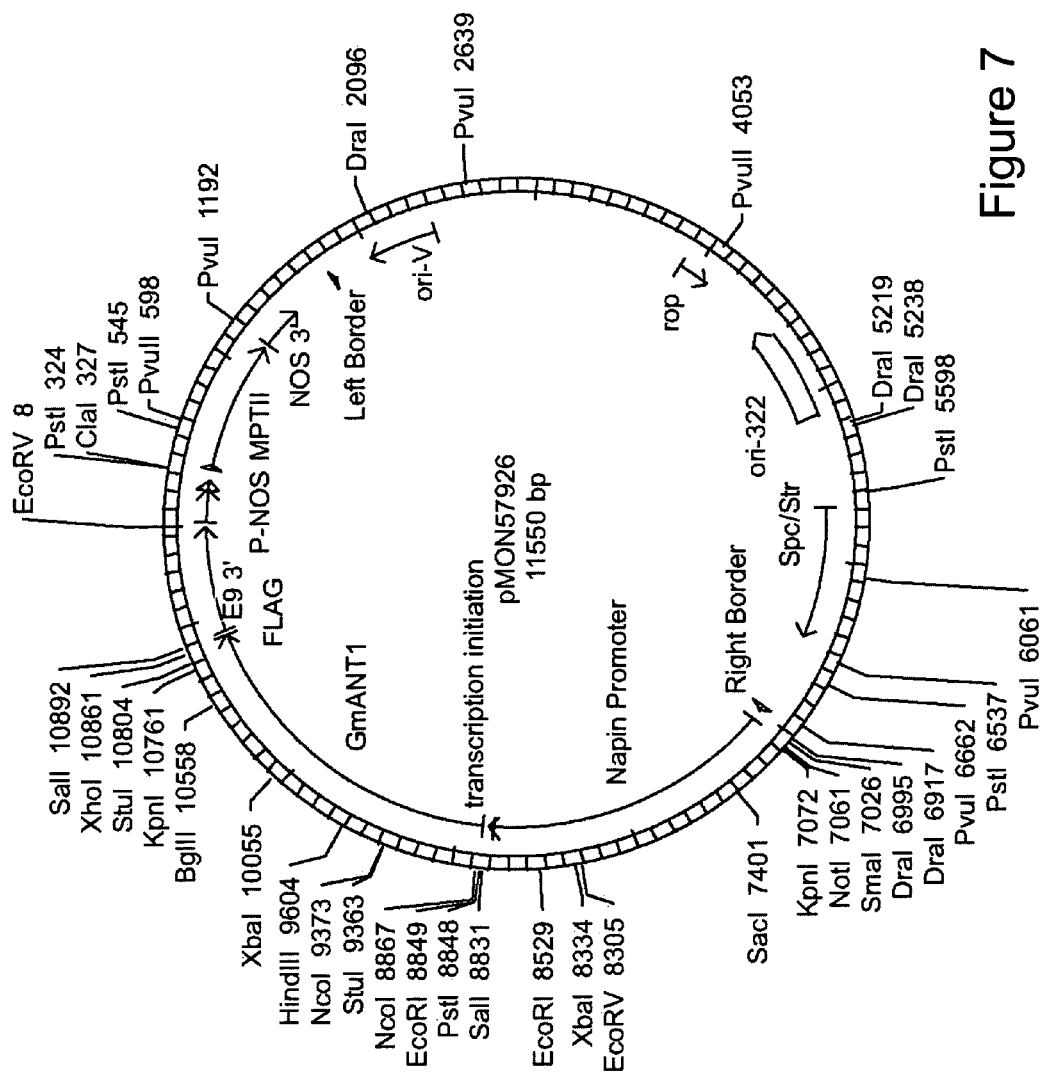
FIG. 7 shows a plasmid map for plant transformation vector pMON57926.
Figure 8:
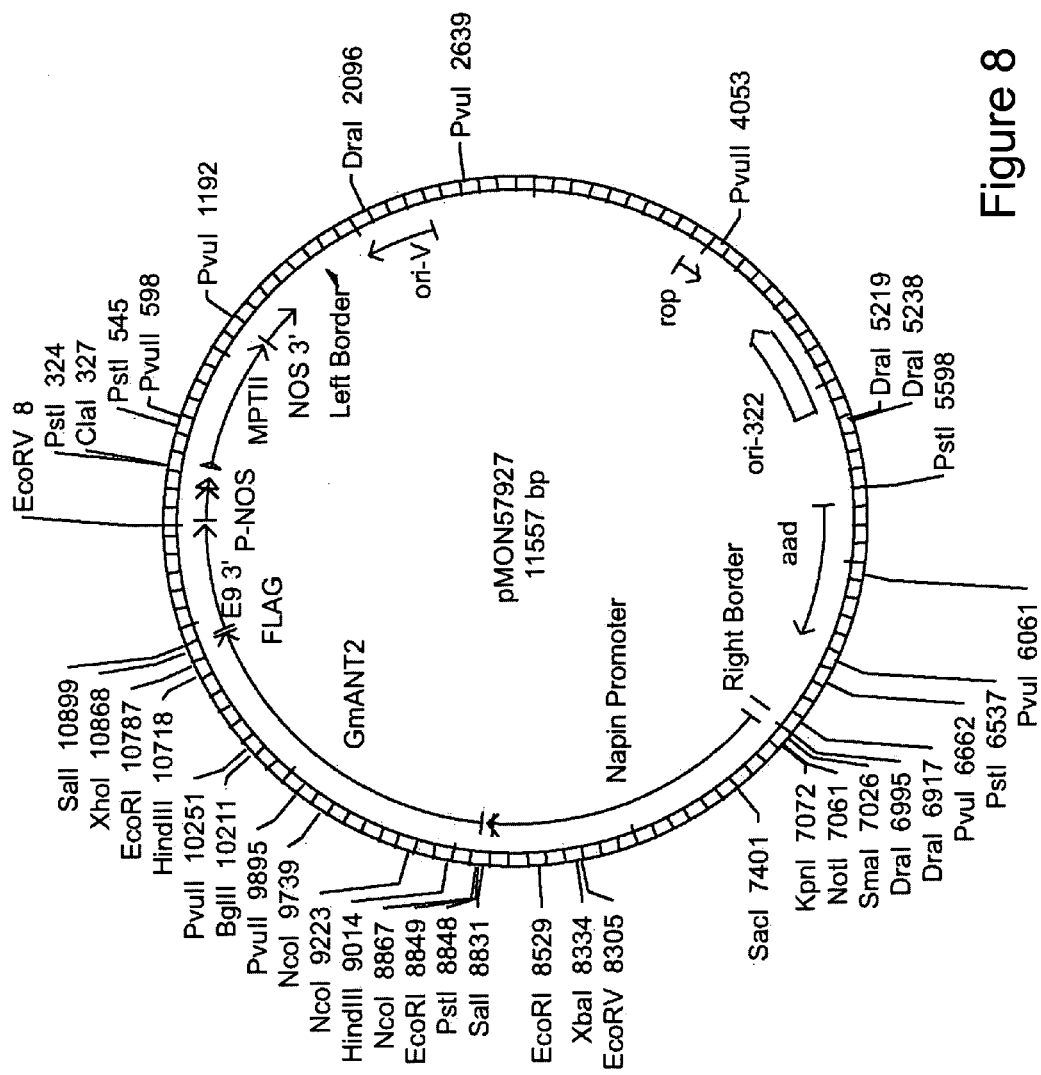
FIG. 8 shows a plasmid map for plant transformation vector pMON57927.
Figure 9:
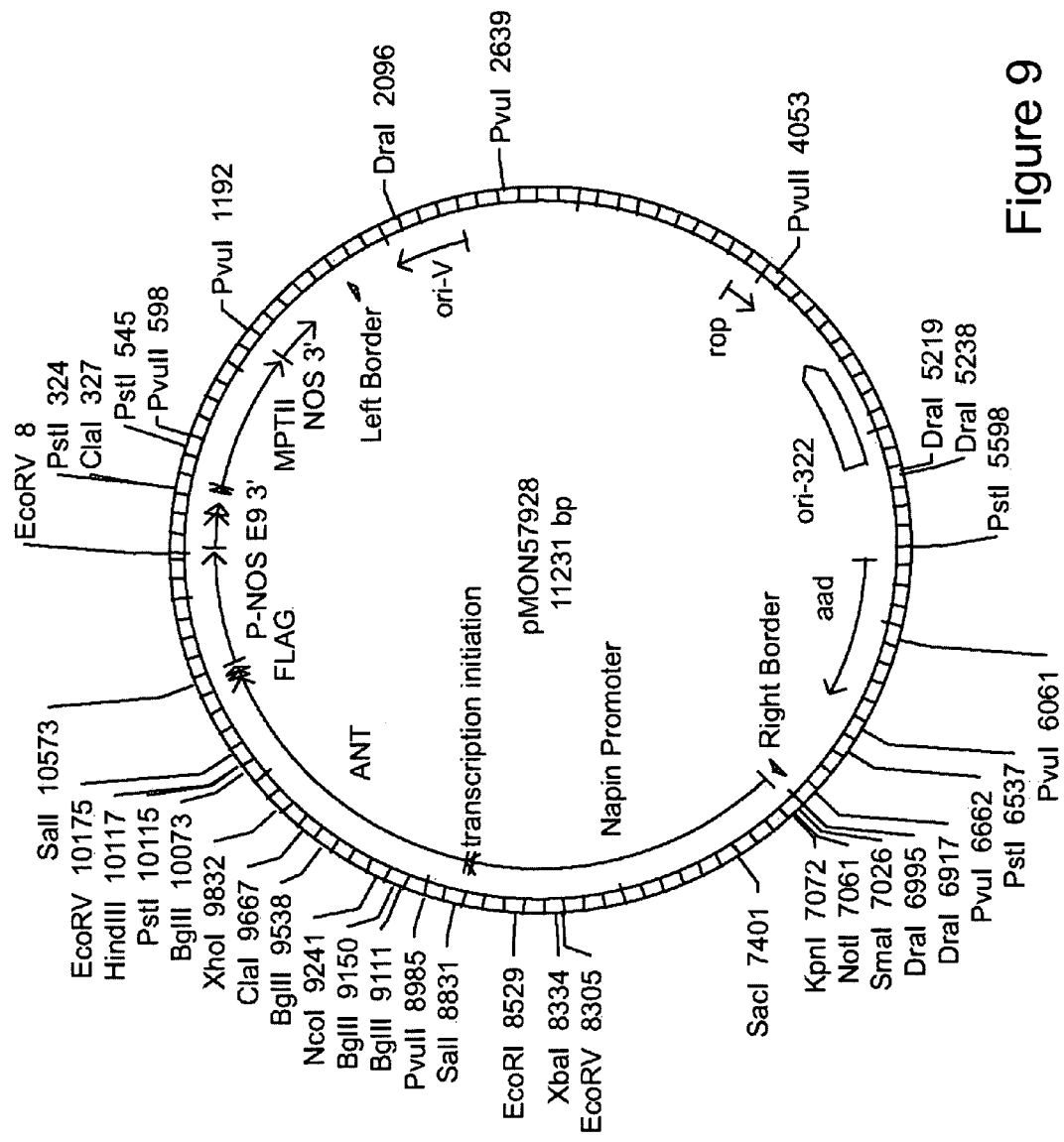
FIG. 9 shows a plasmid map for plant transformation vector pMON57928.
Figure 10:
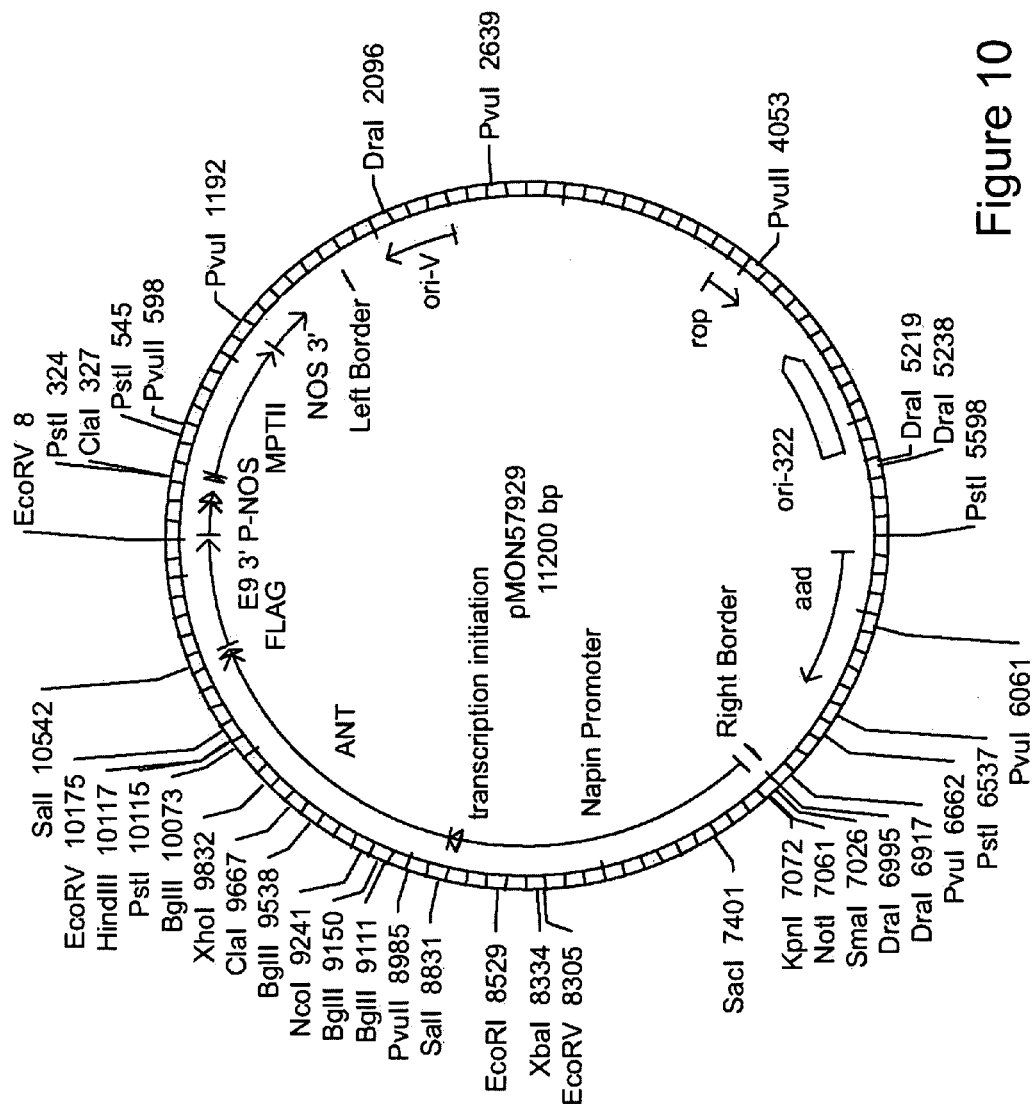
FIG. 10 shows a plasmid map for plant transformation vector pMON57929.
Figure 11:
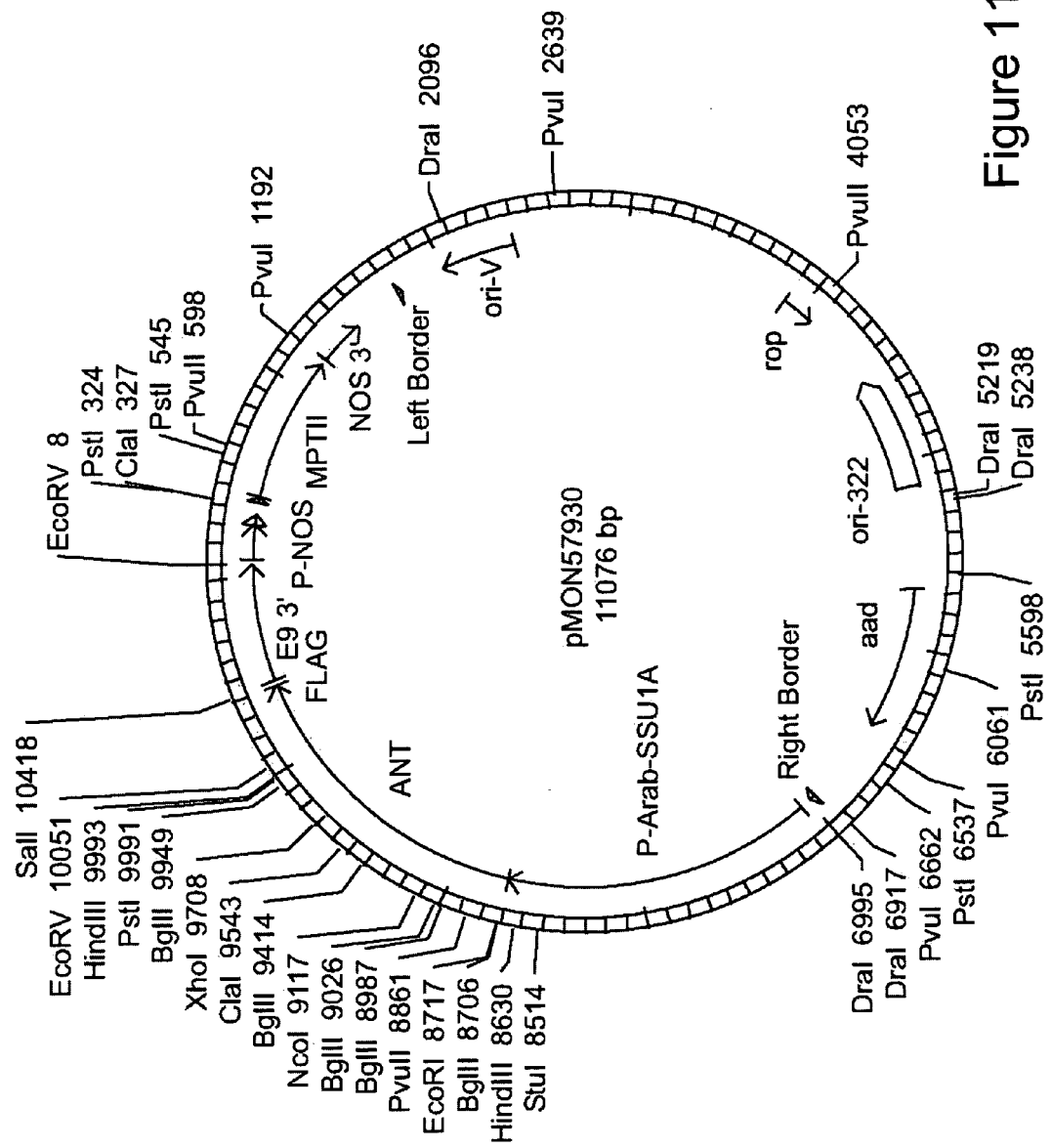
FIG. 11 shows a plasmid map for plant transformation vector pMON57930.
Figure 12:
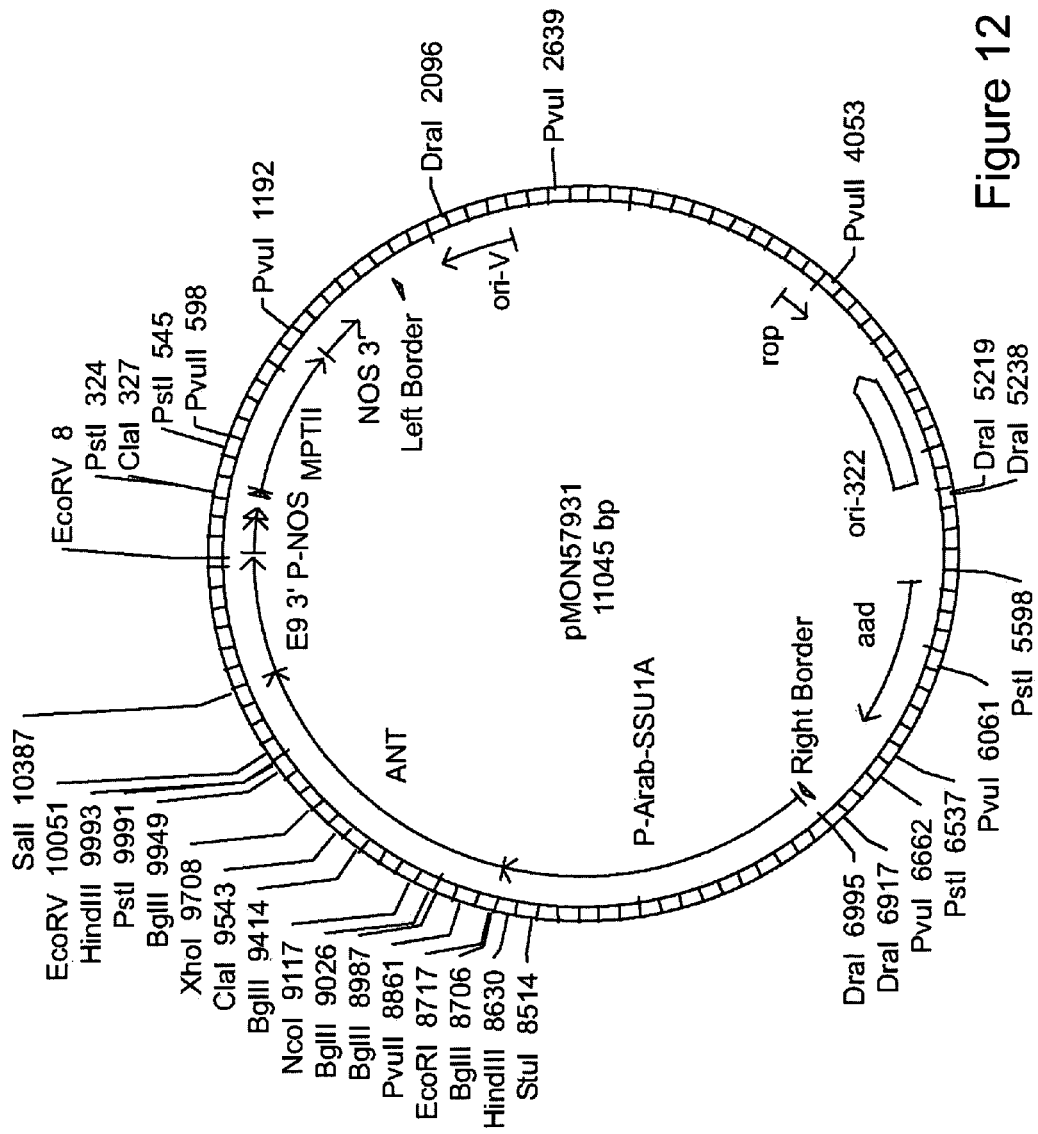
FIG. 12 shows a plasmid map for plant transformation vector pMON57931.
Figure 13:
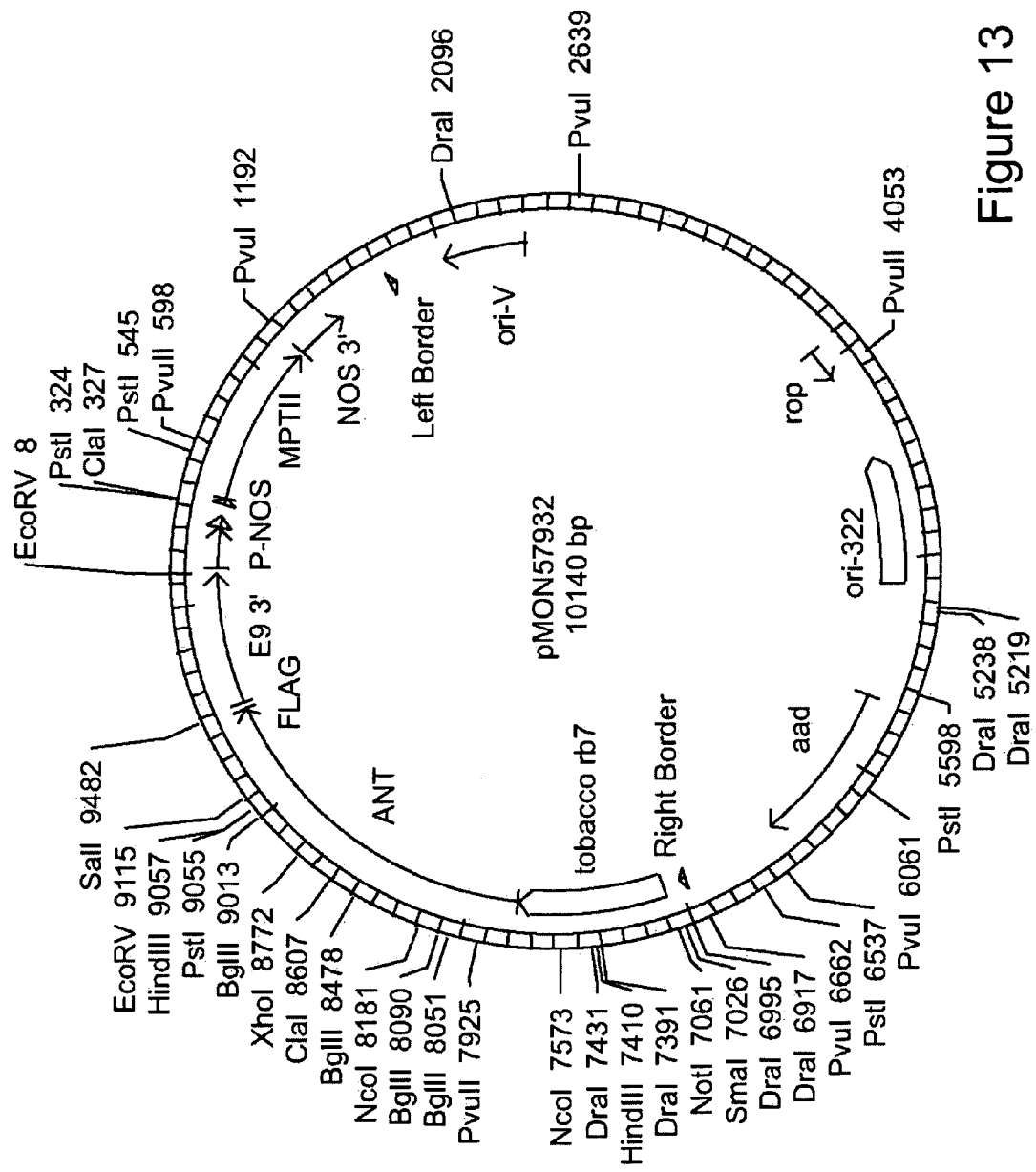
FIG. 13 shows a plasmid map for plant transformation vector pMON57932.
Figure 14:
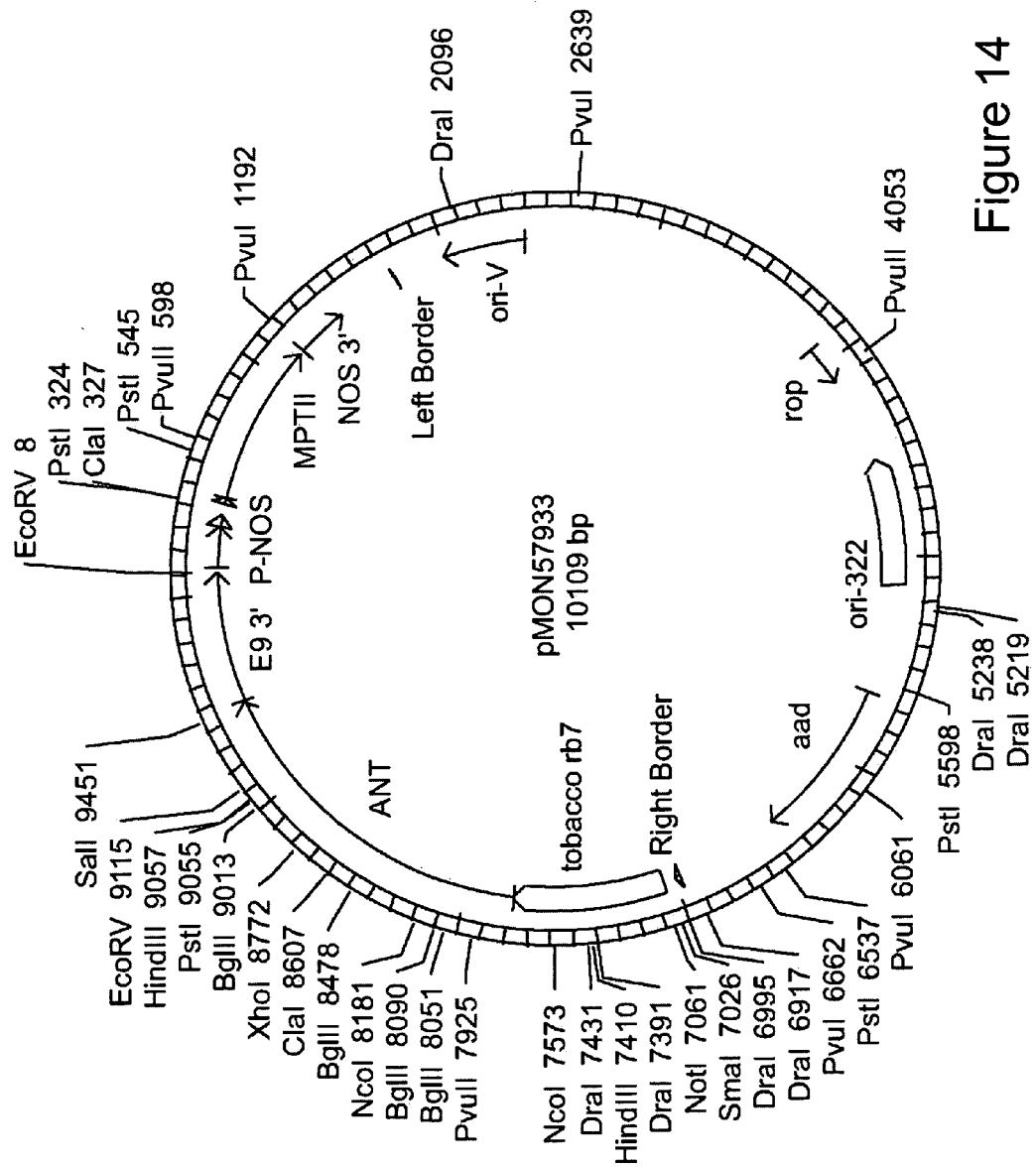
FIG. 14 shows a plasmid map for plant transformation vector pMON57933.
Figure 15:
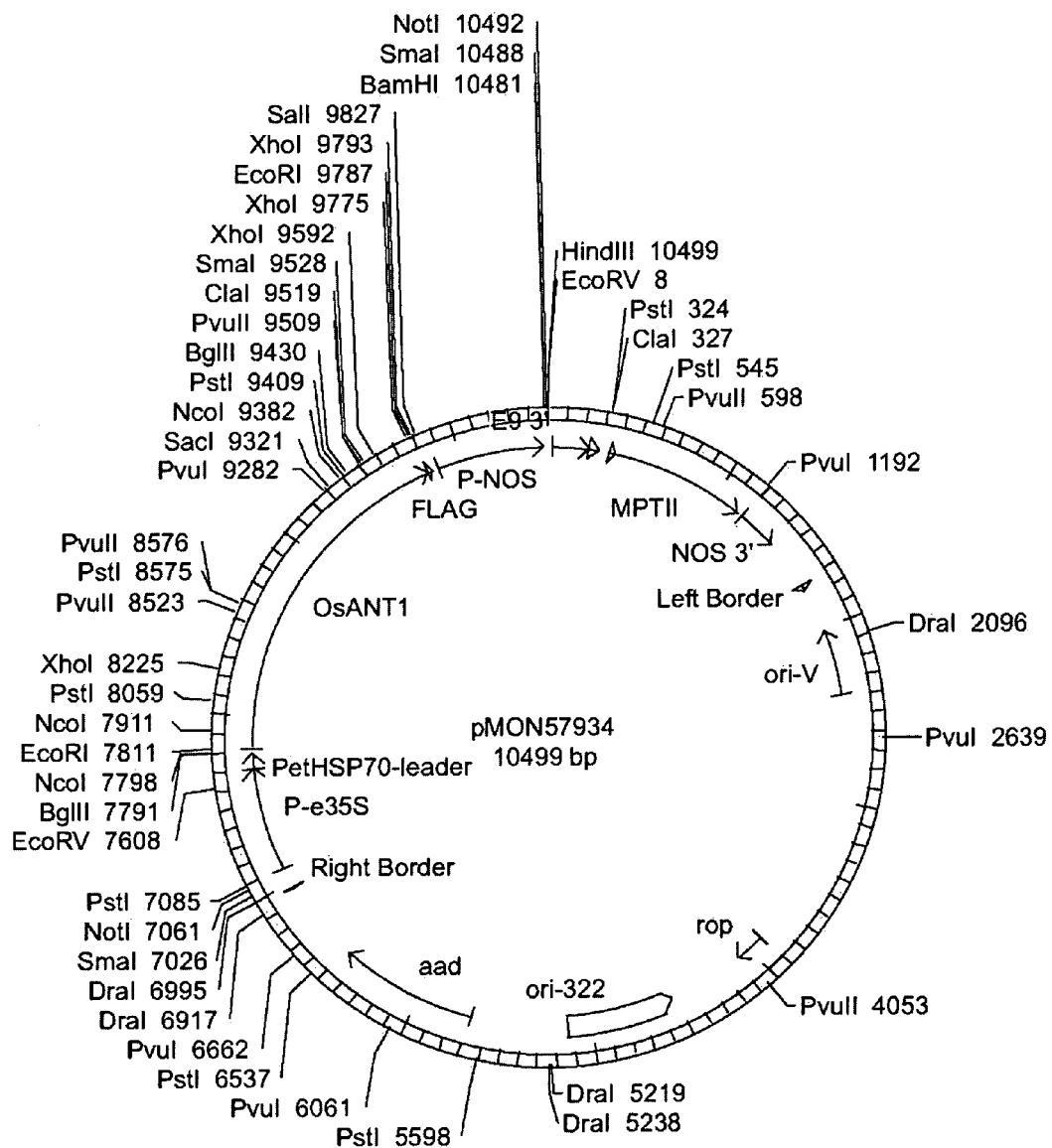
FIG. 15 shows a plasmid map for plant transformation vector pMON57934.
Figure 16:
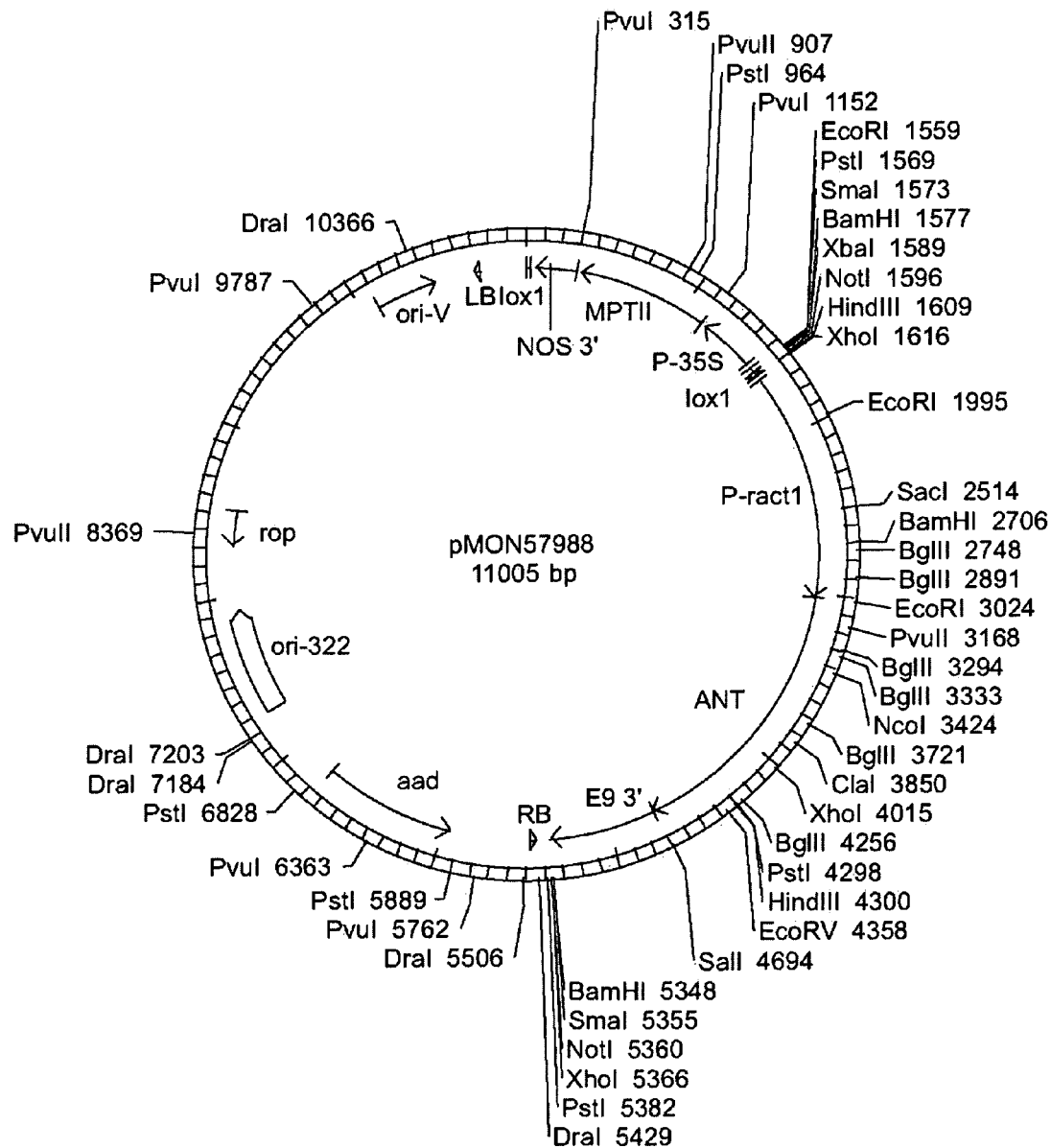
FIG. 16 shows a plasmid map for plant transformation vector pMON57988.
Figure 17:
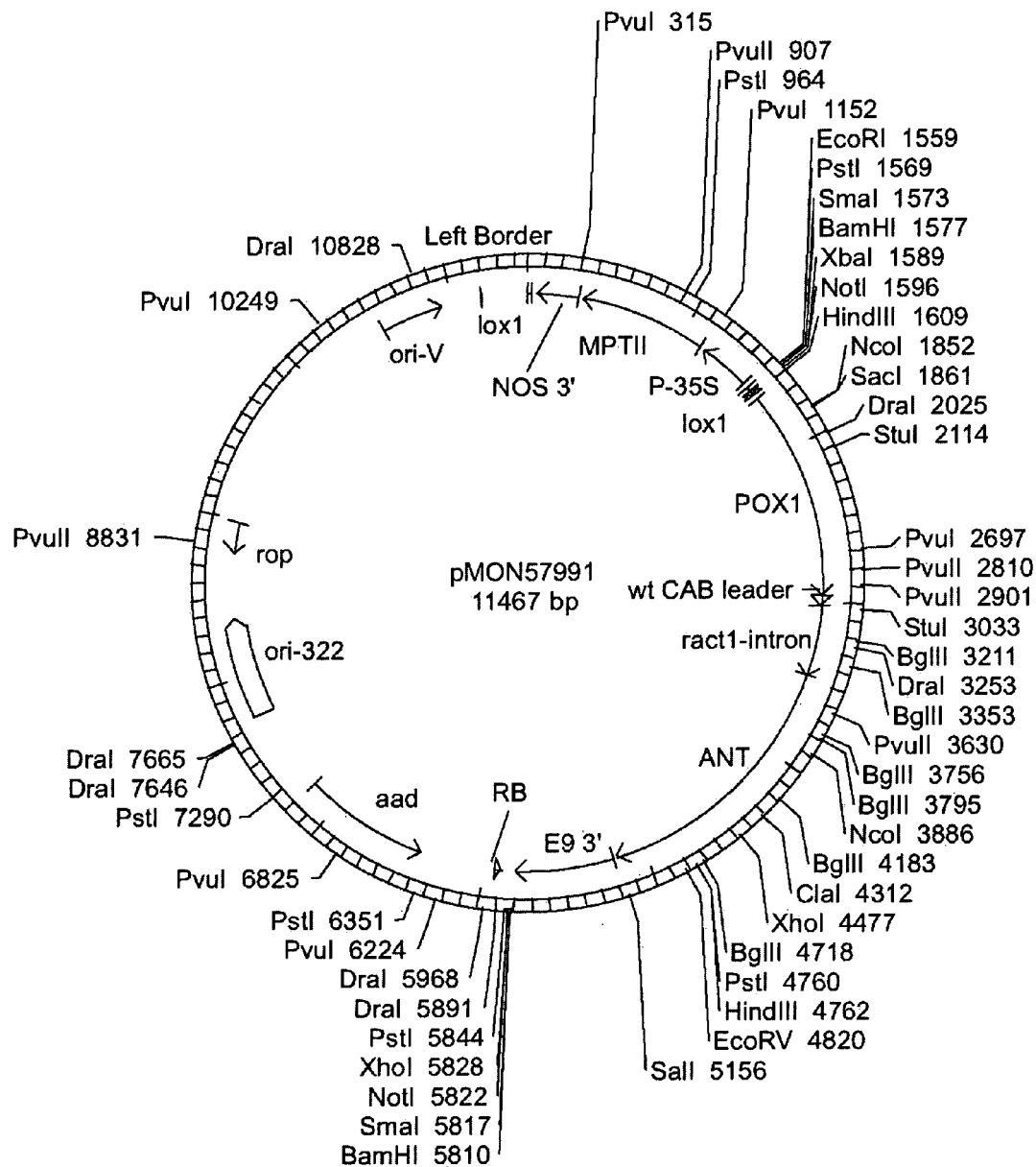
FIG. 17 shows a plasmid map for plant transformation vector pMON57991.
Figure 18:
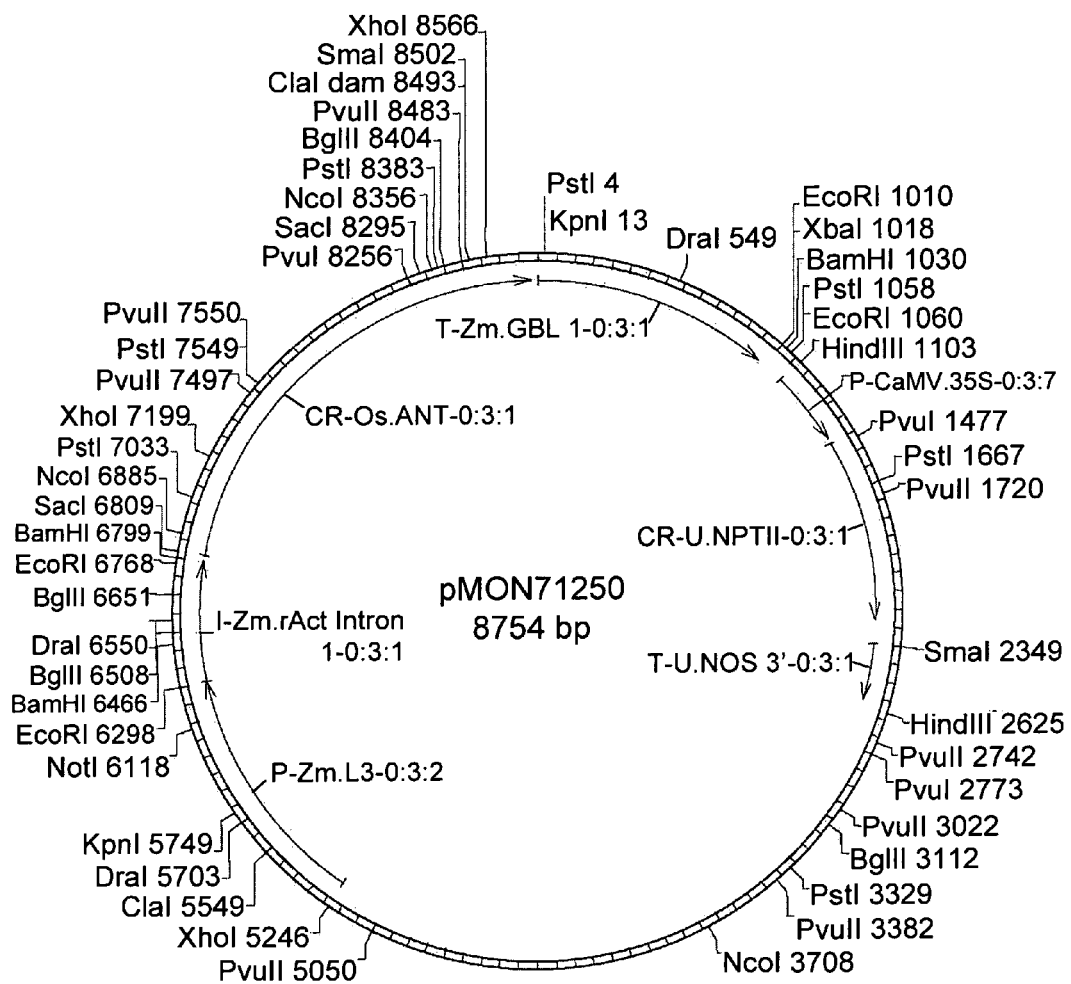
FIG. 18 shows a plasmid map for plant transformation vector pMON71250.

The invention can be more fully understood from the following detailed description and the accompanying Sequence Listing which form a part of this application.

DETAILED DESCRIPTION OF THE INVENTION

The present invention is based, in part, on the isolation and characterization of nucleic acid molecules encoding ANT-like polypeptides from plants including soybean, maize, rice, and cotton. The ANT-like polypeptides of the present invention, like the ANT polypeptide of *Arabidopsis*, contain two highly conserved AP2 DNA-binding domains. It has also been discovered that the ANT-like polypeptides of the present invention and the *Arabidopsis* ANT polypeptide comprise three highly conserved regions in the N-terminal before the AP2 DNA binding domains, and one conserved region in the end of the C-terminal. However, the polypeptides encoded by the nucleic acid molecules disclosed herein share less than 60% amino acid sequence identity to the *Arabidopsis* ANT polypeptide or less than 60% nucleotide sequence identity to the nucleic acid molecule encoding *Arabidopsis* ANT polypeptide, as shown in Tables 1 and 2. In addition, the C-terminal of each of the ANT-like polypeptides disclosed herein is longer than that of the *Arabidopsis* ANT polypeptide after the AP2 DNA binding domains. Finally, two additional conserved regions (shaded) in the C-terminus are only present in the ANT-like polypeptides of the present invention but absent in the *Arabidopsis* ANT polypeptide. A "crop ANT protein" as used herein is a protein with substantial identity to SEQ ID NOs: 2, 4, 6, 9, 11, and 13 or which comprises a polypeptide having in the N-terminal to C-terminal direction two AP2 DNA binding domains followed in the C-terminal by an amino acid subsequence selected from the group consisting of Xaa-Ser-Ser-Ser-Arg-Glu (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue selected from the group consisting of Gly, Ala, Val, Leu, and Ile.

TABLE 1

Percentage sequence identity of Amino Acid sequences of ANT (gi1244708), GhANT1, GmANT1, GmANT2, OsANT1, OsANT2, and ZmANT1 polypeptides*

| | ANT (gi1244708) | GhANT1 (SEQ ID NO:11) | GmANT1 (SEQ ID NO:2) | GmANT2 (SEQ ID NO:4) | OsANT1 (SEQ ID NO:6) | OsANT2 (SEQ ID NO:9) | ZmANT1 (SEQ ID NO:13) |
|---|---|---|---|---|---|---|---|
| ANT (gi1244708) | | 51.03 | 55.77 | 54.31 | 50.87 | 51.12 | 58.10 |
| GhANT1 (SEQ ID NO: 11) | 51.03 | | 50.09 | 49.10 | 47.05 | 46.88 | 45.46 |
| GmANT1 (SEQ ID NO: 2) | 55.77 | 50.09 | | 58.56 | 55.13 | 57.36 | 56.28 |
| GmANT2 (SEQ ID NO: 4) | 54.31 | 49.10 | 58.56 | | 53.48 | 53.08 | 55.83 |
| OsANT1 (SEQ ID NO: 6) | 50.87 | 47.05 | 55.13 | 53.48 | | 59.49 | 63.22 |
| OsANT2 (SEQ ID NO: 9) | 51.12 | 46.88 | 57.36 | 53.08 | 59.49 | | 75.82 |
| ZmANT1 (SEQ ID NO: 13) | 58.10 | 45.46 | 56.28 | 55.83 | 63.22 | 75.82 | |

*See Example 5 for detail.

TABLE 2

Percentage sequence identity of nucleotide sequences encoding ANT (gi1244708), GhANT1, GmANT1, GmANT2, OsANT1, OsANT2, and ZmANT1 polypeptides*

| | ANT (gi1244707) | GhANT1 (SEQ ID NO:10) | GmANT1 (SEQ ID NO:1) | GmANT2 (SEQ ID NO:3) | OsANT1 (SEQ ID NO:5) | OsANT2 (SEQ ID NO:8) | ZmANT1 (SEQ ID NO:12) |
|---|---|---|---|---|---|---|---|
| ANT (gi1244707) | | 51.60 | 58.36 | 59.06 | 53.39 | 51.75 | 54.41 |
| GhANT1 (SEQ ID NO:10) | 51.60 | | 52.66 | 54.09 | 50.91 | 49.46 | 47.38 |
| GmANT1 (SEQ ID NO: 1) | 58.36 | 52.66 | | 63.31 | 53.15 | 53.85 | 53.79 |
| GmANT2 (SEQ ID NO: 3) | 59.06 | 54.09 | 63.31 | | 55.83 | 50.21 | 55.47 |
| OsANT1 (SEQ ID NO: 5) | 53.39 | 50.91 | 53.15 | 55.83 | | 58.52 | 62.23 |
| OsANT2 (SEQ ID NO: 8) | 51.75 | 49.46 | 53.85 | 50.21 | 58.52 | | 75.56 |
| ZmANT1 (SEQ IDNO: 12) | 54.41 | 47.38 | 53.79 | 55.47 | 62.23 | 75.56 | |

*See Example 5 for detail.

The designations of amino acid residues referred to herein, as recommended by the IUPAC-IUB Biochemical Nomenclature Commission, are list in Table 3.

TABLE 3

| Amino Acid | Three-Letter Abbreviation | One-letter Symbol | Amino Acid | Three-Letter Abbreviation | One-letter Symbol |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic Acid | Asp | D | Phenylalanine | Phe | F |
| Cysteine | Cys | C | Proline | Pro | P |
| Glutamine | Gln | Q | Serine | Ser | S |
| Glutamic acid | Glu | E | Threonine | Thr | T |
| Glycine | Gly | G | Tryptophan | Trp | W |

TABLE 3-continued

| Amino Acid | Three-Letter Abbreviation | One-letter Symbol | Amino Acid | Three-Letter Abbreviation | One-letter Symbol |
|---|---|---|---|---|---|
| Histidine | His | H | Tyrosine | Tyr | Y |
| Isoleucine | Ile | I | Valine | Val | V |

Isolated Nucleic Acid Molecules of the Present Invention

One aspect of the present invention relates to an isolated nucleic acid molecule comprising a nucleotide sequence or complement thereof, wherein the nucleotide sequence encodes a polypeptide having in the N-terminal to C-terminal direction two AP2 DNA binding domains followed in the C-terminal by an amino acid subsequence selected from group consisting of Xaa-Ser-Ser-Ser-Arg-Glu (SEQ ID NO: 25), Xaa-Ser-Asn-Ser-Arg-Glu (SEQ ID NO: 26), and Asn-Ser-Ser-Ser-Arg-Asn (SEQ ID NO: 27), wherein Xaa is an amino acid residue having an aliphatic side chain and selected from the group consisting of Gly, Ala, Val, Leu, and Ile. In a preferred embodiment, the amino acid subsequence is selected from the group consisting of Ser-Ser-Leu-Xaa-Thr-Ser-Xaa-Ser-Ser-Ser-Arg-Glu (SEQ ID NO: 28), Ser-Ser-Leu-Xaa-Pro-Ser-Xaa-Ser-Asn-Ser-Arg-Glu (SEQ ID NO: 29), Ser-Ser-Leu-Xaa-Thr-Ser-Xaa-Ser-Asn-Ser-Arg-Glu (SEQ ID NO: 30), and Ser-Leu-Xaa-Asn-Ser-Ser-Ser-Arg-Asn (SEQ ID NO: 31). In a particular preferred embodiment, the polypeptide of the present invention further comprises a second amino acid subsequence selected from the group consisting of Leu-Gly-Phe-Ser-Leu-Ser (SEQ ID NO: 35), Leu-Gly-Phe-Ser-Leu-Thr (SEQ ID NO: 36), Met-Pro-Leu-Lys-Ser-Asp-Gly-Ser (SEQ ID NO: 37), Met-Pro-Leu-Arg-Ser-Asp-Gly-Ser (SEQ ID NO: 38), Met-Pro-Ile-Lys-Ser-Asp-Gly-Ser (SEQ ID NO: 39), Pro-Lys-Leu-Glu-Asp-Phe (SEQ ID NO: 40), and Pro-Lys-Val-Glu-Asp-Phe (SEQ ID NO: 41).

The term "nucleic acid molecule" as used herein means a deoxyribonucleic acid (DNA) molecule or ribonucleic acid (RNA) molecule. Both DNA and RNA molecules are constructed from nucleotides linked end to end, wherein each of the nucleotides contains a phosphate group, a sugar moiety, and either a purine or a pyrimidine base. Nucleic acid molecules can be a single or double-stranded polymer of nucleotides read from the 5' to the 3' end. Nucleic acid molecules may also optionally contain synthetic, non-natural or altered nucleotide bases that permit correct read through by a polymerase and do not alter expression of a polypeptide encoded by that nucleic acid molecule.

The term "an isolated nucleic acid molecule" as used herein means a nucleic acid molecule that is no longer accompanied by some of materials with which it is associated in its natural state or to a nucleic acid molecule the structure of which is not identical to that of any of naturally occurring nucleic acid molecule. Examples of an isolated nucleic acid molecule include: (1) DNAs which have the sequence of part of a naturally occurring genomic DNA molecule but are not flanked by two coding sequences that flank that part of the molecule in the genome of the organism in which it naturally occurs; (2) a nucleic acid molecule incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid molecule may also be comprised of one or more segments of cDNA, genomic DNA or synthetic DNA.

It is also contemplated by the inventors that the isolated nucleic acid molecules of the present invention also include known types of modifications, for example, labels which are known in the art, methylation, "caps", substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, toxins, antibodies, signal peptides, poly-L-lysine, etc.), those with intercalators (acridine, psoralen, etc.), those containing chelators (metals, radioactive metals, boron, oxidative metals, etc.), those containing alkylators, and those with modified linkages.

The term "nucleotide sequence" as used herein means both the sense and antisense strands of a nucleic acid molecule as either individual single strands or in the duplex. It includes, but is not limited to, self-replicating plasmids, chromosomal sequences, and infectious polymers of DNA or RNA.

A nucleotide sequence is said to be the "complement" of another nucleotide sequence if they exhibit complete complementarity. As used herein, molecules are said to exhibit "complete complementarity" when every nucleotide of one of the sequences is complementary to a nucleotide of the other.

As used herein both terms "a coding sequence" and "a structural nucleotide sequence" mean a nucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant nucleotide sequences.

The ANT-like polypeptides of the invention, like other polypeptides, have different domains which perform different functions. Thus, the coding sequences need not be full length, so long as the desired functional domain of the polypeptide is expressed. The distinguishing features of ANT-like polypeptides are discussed in detail in Examples.

The term "recombinant DNAs" or "recombinant DNA molecules" as used herein means DNAs that contains a genetically engineered modification through manipulation via mutagenesis, restriction enzymes, and the like. The nucleic acid itself can come form either naturally occurring sources or can be created in the laboratory. It can also include all vectors created by DNA engineering, for example, all the DNA molecules included herein designated by pMON. For example, it can include molecules containing naturally occurring DNA or cDNA, or DNA molecules of synthetic origin in a plasmid, or isolated.

The term "synthetic DNAs" as used herein means DNAs assembled from oligonucleotide building blocks that are chemically synthesized using procedures known to those skilled in the art. These building blocks are ligated and annealed to form DNA segments which are then enzymatically assembled to construct the entire DNA. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines.

Both terms "polypeptide" and "protein", as used herein, mean a polymer composed of amino acids connected by peptide bonds. An amino acid unit in a polypeptide (or protein) is called a residue. The terms "polypeptide" and "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a polypeptide, that polypeptide is specifically reactive to antibodies elicited to the same polypeptide but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties*, 2nd ed., T. E. Creighton, W. H. Freeman and Company, New York (1993), herein incorporated by reference in its entirety. Many detailed reviews are available on this subject, such as, for example, those provided by Wold, F., Post-translational Protein Modifications. Perspectives and Prospects, pp. 1–12 in *Post-translational Covalent Modification of Proteins*, B. C. Johnson, Ed., Academic Press, New York (1983); Seifter et al., *Meth. Enzymol.* 182:626-M (1990) and Rattan et al., *Protein Synthesis: Post-translational Modifications and Aging, Ann. N.Y. Acad. Sci.* 663:48–62 (1992), herein incorporated by reference in their entirety. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine-containing and the methionine-less amino terminal variants of the polypeptide of the invention. Thus, as used herein, the terms "protein" and "polypeptide" include any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids. This definition is meant to include norleucine, ornithine, homocysteine, and homoserine.

The term "amino acid sequence" means the sequence of amino acids in a polypeptide (or protein) that is written starting with the amino-terminal (N-terminal) residue and ending with the carboxyl-terminal (C-terminal) residue.

The term "an amino acid subsequence" means a portion of the amino acid sequence of a polypeptide. An amino acid subsequence generally has a length of 3 to 50 amino acid residues.

Both terms "substantially purified polypeptide" and "substantially purified protein", as used herein, means a polypeptide or protein that is separated substantially from all other molecules normally associated with it in its native state and is the predominant species present in a preparation. A substantially purified molecule may be greater than 60% free, preferably 75% free, more preferably 90% free, and most preferably 95% free from the other molecules (exclusive of solvent) present in the natural mixture.

As used herein the term "AP2 DNA binding domain" means a 68 amino acid motif found in the *Arabidopsis* APETALA2 (AP2) polypeptide as reported by Jofuku, et al., *Plant Cell* 6:1211–1225 (1994) and in WO 97/14659 as being homologous to the DNA binding domain of ethylene response element binding proteins. With reference to FIGS. 2*a* and 2*b* for purposes of defining amino acid sequence of polypeptides of the present invention an AP2 DNA binding domain means an amino acid motif the amino acid sequence of which is determined to have at least 85% sequence identity to the amino acid sequence of the *Arabidopsis* ANT polypeptide (gi1244708) between amino acid 281 and amino acid 354 or between amino acid 383 and amino acid 448, using the Gap program in the WISCONSIN PACKAGE version 10.0-UNIX from Genetics Computer Group, Inc. based on the method of Needleman and Wunsch (J. Mol. Biol. 48:443–453 (1970), herein incorporated by reference in its entirety) using the set of default parameters for pairwise comparison (for amino acid sequence comparison: Gap Creation Penalty=8, Gap Extension Penalty=2).

"Percentage of sequence identity" is determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein the term "ANT-like polypeptide" means a polypeptide, wherein the overexpression of an exogenous nucleic acid molecule encoding said polypeptide in a transgenic plant wherein the amino acid sequence of said polypeptide is substantially identical to a sequence selected from the group consisting of SEQ ID Nos: 2, 4, 6, 9, 11, and 13. Preferably, the overexpression of an exogenous nucleic acid molecule encoding an ANT-like polypeptide of the present invention under the control of a constitutive promoter in a transgenic plant will have minimal effects on the female fertility or male fertility or both thereof of the trangenic plant.

The term "intrinsic size" as used herein means the size of an organ or tissue of a plant, that is grown under optimal growth conditions, at maturity or any other defining time in its life cycle.

Both terms "substantially identical" and "substantial identity", used in reference to amino acid sequences or nucleotide sequences, means that one amino acid sequence or one nucleotide sequence has at least 60% sequence identity compared to the other amino acid sequence or nucleotide sequence as a reference sequence using the Gap program in the WISCONSIN PACKAGE version 10.0-UNIX from Genetics Computer Group, Inc. based on the method of Needleman and Wunsch (J. Mol. Biol. 48:443–453 (1970), herein incorporated by reference in its entirety) using the set of default parameters for pairwise comparison (for amino acid sequence comparison: Gap Creation Penalty=8, Gap Extension Penalty=2; for nucleotide sequence comparison: Gap Creation Penalty=50; Gap Extension Penalty=3).

One aspect of the present invention provides an isolated nucleic acid molecule comprising a nucleotide sequence or complement thereof, wherein the nucleotide sequence encodes a polypeptide having an amino acid sequence that has at least 60% sequence identity, preferably at least 70% or 75% sequence identity, more preferably at least 80% or 85% sequence identity, even more preferably at least 90% or 95% sequence identity, and most preferably at least 98% sequence identity to a member selected from group consisting of SEQ ID NOs: 2, 4, 6, 9, 11, and 13.

Polypeptides which are "substantially similar" share sequences as noted above except that residue positions which are not identical may differ by conservative amino acid changes. Conservative amino acid substitutions refer to the interchangeability of residues having similar side chains. "Conservative amino acid substitutions" mean substitutions of one or more amino acids in a native amino acid sequence with another amino acid(s) having similar side chains. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine.

One skilled in the art will recognize that the values of the above substantial identity of nucleotide sequences can be appropriately adjusted to determine corresponding sequence identity of two nucleotide sequences encoding the polypeptides of the present invention by taking into account codon degeneracy, conservative amino acid substitutions, reading frame positioning and the like. Substantial identity of nucleotide sequences for these purposes normally means sequence identity of at least 35%.

As used herein yeast regularly refers to *Saccharomyces cerevissiae* but could also include *Schizosacchoramyces pombe* and other varieties (from the genus *Pichia*, for example). Corn refers to *Zea Mays* and all species and varieties that can be bred with it. Wheat refers to all of *Triticum aestivum* varieties including but not limited to spring, winter, and all facultative wheat varieties. Wheat includes any other wheat species, including but not limited to durum wheat (*Triticum durum*), spelt (*Triticum spelta*), emmer (*Triticum dicoccum*), and wild wheat (*Triticum monococcum*). Wheat also includes any species that can be bred with any of the aforementioned wheat species and offspring of said crosses (including triticale, a hybrid of wheat and rye). Soybeans refers to *Glycine max* or *Glycine soja* and any species or variety that can be bred with them. Rice refers to *Oryza sativa* and any species or variety that can be bred with it. Barley refers to *Hordeum vulgare* and any species or variety that can be bred with it. Oats refers to *Avena sativa* and any species or variety that can be bred with it. Canola is a coined name recently given to seed, oil, and meal produced by genetically modified rapeseed plants, oilseed rape (*Brassica napus* L.) and turnip rape (*B. campestris* L), herein canola includes all rapeseed plants and organisms that can be bred with them. *E. coli* and *Escherichia coli* as used herein includes organisms of the *Escherichia coli* species and all strains of that this organism; i.e. *E. coli* K12. *E. coli* and *Escherichia coli* as used herein can also includes any organism that can conjugate with any *E. coli* strain when one is an F$^+$ or Hfr strain, and the other is not. *B. subtilis* and *Bacillus subtilis* refers to all organism of the genus *Bacillus*, species *subtilis*. *Agrobacterium tumifaciens* as used herein includes all strains and types of this species. Turf grasses include all species and strains of grass ever planted, or that could be planted, to produce a turf, including but not limited to; a lawn, a field for playing a game (i.e. football, baseball, or soccer), and all areas of a golf course (i.e. tee, fairway, green, rough, etc.). Cotton refers to all plants in the genus Gossypium and all plants that can be bred with them.

The term "codon degeneracy" means divergence in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for ectopic expression in a host cell, it is desirable to design the gene such that its frequency of codon usage approaches the frequency of preferred codon usage of the host cell.

In another aspect, the present invention provides an isolated nucleic acid molecule comprising a nucleotide sequence or complement thereof, wherein the nucleotide sequence hybridizes under stringent conditions to the complement of a second nucleotide sequence encoding a polypeptide having an amino acid sequence selected from the group consisting of SEQ ID Nos: 2, 4, 6, 9, 11, and 13.

Hybridization conditions are sequence dependent and will be different in different circumstances. As used herein "stringent conditions" are selected to be about 5° C. lower than the thermal melting point (Tm) for the specific sequence at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6, incorporated herein by reference in its entirety. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0×SSC at a temperature of at least about 50° C. for 20 minutes, or equivalent conditions.

In a preferred embodiment, an isolated nucleic acid molecule of the present invention comprises a nucleotide sequence or complement thereof, wherein the nucleotide sequence hybridizes under moderately stringent conditions such as 2.0×SSC and about 65° C. to the complement of a second nucleotide sequence encoding a polypeptide having an amino acid sequence selected from the group consisting of SEQ ID Nos: 2, 4, 6, 9, 11, and 13.

In a particularly preferred embodiment, an isolated nucleic acid molecule of the present invention comprises a nucleotide sequence or complement thereof, wherein the nucleotide sequence hybridizes under high stringency conditions such as 0.2×SSC and about 65° C. to the complement of a second nucleotide sequence encoding a polypeptide having an amino acid sequence selected from the group consisting of SEQ ID Nos: 2, 4, 6, 9, 11, and 13.

The nucleic acid molecules encoding an ANT-like polypeptide of the present invention may be combined with other non-native, or "heterologous" sequences in a variety of ways. By "heterologous" sequences it is meant any sequence which is not naturally found joined to the nucleotide sequence encoding ANT-like polypeptide, including, for example, combinations of nucleotide sequences from the same plant which are not naturally found joined together, or the two sequences originate from two different species.

In another aspect, the present invention provides an isolated nucleic acid molecule comprising a structural nucleotide sequence and operably linked regulatory sequences, wherein the structural nucleotide sequence encodes a polypeptide having an amino acid sequence that is substantially identical to a member selected from group consisting of SEQ ID NOs: 2, 4, 6, 9, 11, and 13.

The term "operably linked", as used in reference to a regulatory sequence and a structural nucleotide sequence, means that the regulatory sequence causes regulated expression of the operably linked structural nucleotide sequence. "Expression" means the transcription and stable accumulation of sense or antisense RNA derived from the nucleic acid molecule of the present invention. Expression may also refer to translation of mRNA into a polypeptide. "Sense" RNA means RNA transcript that includes the mRNA and so can be translated into polypeptide or protein by the cell. "Antisense RNA" means a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" means the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

The term "overexpression" means the expression of a polypeptide encoded by an exogenous nucleic acid molecule introduced into a host cell, wherein said polypeptide is either not normally present in the host cell, or wherein said polypeptide is present in said host cell at a higher level than that normally expressed from the endogenous gene encoding said polypeptide.

By "ectopic expression" it is meant that expression of a nucleic acid molecule encoding a polypeptide in a cell type other than a cell type in which the nucleic acid molecule is normally expressed, at a time other than a time at which the nucleic acid molecule is normally expressed or at a expression level other than the level at which the nucleic acid molecule normally is expressed.

"Antisense inhibition" means the production of antisense RNA transcripts capable of suppressing the expression of the target polypeptide. "Co-suppression" means the production of sense RNA transcripts capable of suppressing the expression of identical or substantially similar foreign or endogenous genes (U.S. Pat. No. 5,231,020, incorporated herein by reference).

The term "a gene" means the segment of DNA that is involved in producing a polypeptide. Such segment of DNA includes regulatory sequences preceding (5' non-coding sequences) and following (3' non-coding sequences) the coding region as well as intervening sequences (introns) between individual coding segments (exons). A "Native gene" means a gene as found in nature with its own regulatory sequences. "Chimeric gene" means any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" means a native gene in its natural location in the genome of an organism. A "foreign gene" means a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Regulatory sequences" mean nucleotide sequences located upstream (5' non-coding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

The term "promoter sequence" means a nucleotide sequence that is capable of, when located in cis to a structural nucleotide sequence encoding a polypeptide, functioning in a way that directs expression of one or more mRNA molecules that encodes the polypeptide. Such promoter regions are typically found upstream of the trinucleotide ATG sequence at the start site of a polypeptide coding region. Promoter sequences can also include sequences from which transcription of transfer RNA (tRNA) or ribosomal RNA (rRNA) sequences are initiated. Transcription involves the synthesis of a RNA chain representing one strand of a DNA duplex. By "representing" it is meant that the RNA is identical in sequence with one strand of the DNA; it is complementary to the other DNA strand, which provides the template for its synthesis. Transcription takes place by the usual process of complementary base pairing, catalyzed and scrutinized by the enzyme RNA polymerase. The reaction can be divided into three stages described as initiation, elongation and termination. Initiation begins with the binding of RNA polymerase to the double stranded (DS or ds)

DNA. The sequence of DNA required for the initiation reaction defines the promoter. The site at which the first nucleotide is incorporated is called the start-site or start-point of transcription. Elongation describes the phase during which the enzyme moves along the DNA and extends the growing RNA chain. Elongation involves the disruption of the DNA double stranded structure in which a transiently unwound region exists as a hybrid RNA-DNA duplex and a displaced single strand of DNA. Termination involves recognition of the point at which no further bases should be added to the chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA. The sequence of DNA required for the termination reaction is called the terminator.

The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions.

Promoters which are known or are found to cause transcription of DNA in plant cells can be used in the present invention. Such promoters may be obtained from a variety of sources such as plants and plant viruses. A number of promoters, including constitutive promoters, inducible promoters and tissue-specific promoters, that are active in plant cells have been described in the literature. It is preferred that the particular promoter selected should be capable of causing sufficient expression to result in the production of an effective amount of a polypeptide to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions.

The term "constitutive promoter" means a regulatory sequence which causes expression of a structural nucleotide sequence in most cells or tissues at most times. Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (CaMV) 19S and 35S (sometimes called 35S herein, or a derivative of which is called e35S {U.S. Pat. Nos. 5,359,142, 5,196,525, 5,322,938, 5,164,316, and 5,424,200}); the tobacco mosaic virus promoter; the figwort mosaic virus promoters; and actin promoters, such as the *Arabidopsis* actin gene promoter (see, e.g., Huang et al., *Plant Mol. Biol.* 33:125–139 (1997), herein incorporated by reference in its entirety).

The term "inducible promoter" means a regulatory sequence which causes conditional expression of a structural nucleotide sequence under the influence of changing environmental conditions or developmental conditions. Examples of inducible promoters include but are not limited to the light-inducible promoter from the small subunit of ribulose-1,5-bis-phosphate carboxylase (ssRUBISCO); the drought-inducible promoter of maize (Busk et al., *Plant J.* 11: 1285–1295 (1997), herein incorporated by reference in its entirety); the cold, drought, and high salt inducible promoter from potato (Kirch, *Plant Mol. Biol.* 33:897–909 (1997), herein incorporated by reference in its entirety); a nitrate-inducible promoter derived from the spinach nitrite reductase gene (Back et al., *Plant Mol. Biol.* 17:9 (1991), herein incorporated by its entirety); salicylic acid inducible promoter (Uknes et al., *Plant Cell* 5:159–169 (1993); Bi et al., *Plant J.* 8:235–245 (1995) herein incorporated by reference in their entireties); the auxin-response elements E1 promoter fragment (AuxREs) in the soybean (*Glycine max* L.) (Liu et al., *Plant Physiol.* 115:397–407 (1997), herein incorporated by reference in its entirety); the auxin-responsive *Arabidopsis* GST6 promoter (also responsive to salicylic acid and hydrogen peroxide) (Chen et al., *Plant J.* 10: 955–966 (1996), herein incorporated by reference in its entirety); the auxin-inducible parC promoter from tobacco (Sakai et al., *Plant Cell Physiol.* 37:906–913 (1996), herein incorporated by reference in its entirety); a plant biotin response element (Streit et al., *Mol. Plant Microbe Interact.* 10:933–937 (1997), herein incorporated by reference in its entirety); the promoter responsive to the stress hormone abscisic acid (Sheen et al., *Science* 274:1900–1902 (1996), herein incorporated by reference in its entirety); the maize In2-2 promoter activated by benzenesulfonamide herbicide safeners (De Veylder et al, *Plant Cell Physiol.* 38:568–577 (1997), herein incorporated by reference in its entirety); a tetracycline-inducible promoter, such as the promoter for the *Avena sativa* L. (oat) arginine decarboxylase gene (Masgrau et al., *Plant J.* 11:465–473 (1997), herein incorporated by reference in its entirety); and a salicylic acid-responsive element (Stange et al., *Plant J.* 11:1315–1324 (1997), herein incorporated by reference in its entirety).

The term "tissue-specific promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well. Another set of preferred promoters are root enhanced or specific promoters such as the CaMV derived 4 as-1 promoter or the wheat POX1 (also sometime called pox1) promoter (U.S. Pat. No. 5,023,179, specifically incorporated herein by reference; Hertig et al., 1991).

A variety of promoters specifically active in vegetative tissues, such as leaves, stems, roots and tubers, can be used to express the nucleic acid molecules of the present invention. Examples of tuber-specific promoters include but are not limited to the class I and II patatin promoters (Bevan et al., *EMBO J.* 8: 1899–1906 (1986); Koster-Topfer et al., *Mol Gen Genet.* 219: 390–396 (1989); Mignery et al., *Gene.* 62: 27–44 (1988); Jefferson et al., *Plant Mol. Biol.* 14: 995–1006 (1990), herein incorporated by reference in their entireties), the promoter for the potato tuber ADPGPP genes, both the large and small subunits; the sucrose synthase promoter (Salanoubat and Belliard, *Gene.* 60: 47–56 (1987), Salanoubat and Belliard, *Gene.* 84: 181–185 (1989), herein incorporated by reference in their entirety); and the promoter for the major tuber proteins including the 22 kd protein complexes and proteinase inhibitors (Hannapel, *Plant Physiol.* 101: 703–704 (1993), herein incorporated by reference in its entirety). Examples of leaf-specific promoters include but are not limited to the ribulose biphosphate carboxylase (RBCS or RuBISCO) promoters (see, e.g., Matsuoka et al., *Plant J.* 6:311–319 (1994), herein incorporated by reference in its entirety); the light harvesting chlorophyll a/b binding protein gene promoter (see, e.g., Shiina et al., *Plant Physiol.* 115:477–483 (1997); Casal et al., *Plant Physiol.* 116:1533–1538 (1998), herein incorporated by reference in their entireties); and the *Arabidopsis thaliana* myb-related gene promoter (Atmyb5) (Li et al., *FEBS Lett.* 379:117–121 (1996), herein incorporated by reference in its entirety). Examples of root-specific promoter include but are not limited to the promoter for the acid chitinase gene (Samac et al., *Plant Mol. Biol.* 25: 587–596 (1994), herein incorporated by reference in its entirety); the root specific subdomains of the CaMV35S promoter that have been identified (Lam et al., *Proc. Natl. Acad. Sci.* (*U.S.A.*) 86:7890–7894 (1989), herein incorporated by reference in its entirety); the ORF13 promoter from *Agrobacterium rhizogenes* which exhibits high activity in roots (Hansen et al., *Mol. Gen. Genet.* 254:337–343 (1997), herein incorporated by reference in its entirety); the promoter for the tobacco root-specific gene RB7 (U.S. Pat. No. 5,750, 386; Yamamoto et al., *Plant Cell* 3:371–382 (1991), herein incorporated by reference in its entirety); and the root cell specific promoters reported by Conkling et al. (Conkling et al., *Plant Physiol.* 93:1203–1211 (1990), herein incorporated by reference in its entirety).

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems (Di Laurenzio et al., *Cell* 86:423–433 (1996); Long, Nature 379:66–69 (1996); herein incorporated by reference in their entireties), can be used. Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto et al., *Plant Cell.* 7:517–527 (1995), herein incorporated by reference in its entirety). Also another example of a useful promoter is that which controls the expression of knl-related genes from maize and other species which show meristem-specific expression (see, e.g., Granger et al., *Plant Mol. Biol.* 31:373–378 (1996); Kerstetter et al., *Plant Cell* 6:1877–1887 (1994); Hake et al., *Philos. Trans. R. Soc. Lond. B. Biol. Sci.* 350:45–51 (1995), herein incorporated by reference in their entireties). Another example of a meristematic promoter is the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln et al., *Plant Cell* 6:1859–1876 (1994), herein incorporated by reference in its entirety).

Suitable seed-specific promoters can be derived from the following genes: MAC1 from maize (Sheridan et al., *Genetics* 142:1009–1020 (1996), herein incorporated by reference in its entirety); Cat3 from maize (GenBank No. L05934, Abler et al., *Plant Mol. Biol.* 22:10131–1038 (1993), herein incorporated by reference in its entirety); vivparous-1 from *Arabidopsis* (Genbank No. U93215); Atimyc1 from *Arabidopsis* (Urao et al., *Plant Mol. Biol.* 32:571–57 (1996); Conceicao et al., *Plant* 5:493–505 (1994), herein incorporated by reference in their entireties); napA from *Brassica napus* (GenBank No. J02798); the napin gene family from *Brassica napus* (Sjodahl et al., *Planta* 197:264–271 (1995), herein incorporated by reference in its entirety).

The ovule-specific promoter for BEL1 gene (Reiser et al. *Cell* 83:735–742 (1995), GenBank No. U39944; Ray et al, *Proc. Natl. Acad. Sci. USA* 91:5761–5765 (1994), all of which are herein incorporated by reference in their entireties) can also be used. The egg and central cell specific MEA (FIS1) and FIS2 promoters are also useful reproductive tissue-specific promoters (Luo et al., *Proc. Natl. Acad. Sci. USA,* 97:10637–10642 (2000); Vielle-Calzada, et al., *Genes Dev.* 13:2971–2982 (1999); herein incorporated by reference in their entireties).

A maize pollen-specific promoter has been identified in maize (Guerrero et al., Mol. Gen. Genet. 224:161–168 (1990), herein incorporated by reference in its entirety). Other genes specifically expressed in pollen have been described (see, e.g., Wakeley et al., Plant Mol. Biol. 37:187–192 (1998); Ficker et al., Mol. Gen. Genet. 257: 132–142 (1998); Kulikauskas et al., Plant Mol. Biol. 34:809–814 (1997); Treacy et al., *Plant Mol. Biol.* 34:603–611 (1997); all of which are herein incorporated by reference in their entireties).

Promoters derived from genes encoding embryonic storage proteins, which includes the gene encoding the 2S storage protein from *Brassica napus* (Dasgupta et al, Gene 133:301–302 (1993), herein incorporated by reference in its entirety); the 2s seed storage protein gene family from *Arabidopsis*; the gene encoding oleosin 20 kD from Brassica napus (GenBank No. M63985); the genes encoding oleosin A (GenBank No. U09118) and oleosin B (GenBank No. U09119) from soybean; the gene encoding oleosin from *Arabidopsis* (GenBank No. Z17657); the gene encoding oleosin 18 kD from maize (GenBank No. J05212, Lee, Plant Mol. Biol. 26:1981–1987 (1994), herein incorporated by reference in its entirety); and the gene encoding low molecular weight sulphur rich protein from soybean (Choi et al., Mol. Gen. Genet. 246:266–268 (1995), herein incorporated by reference in its entirety), can also be used.

Promoters derived from zein encoding genes (including the 15 kD, 16 kD, 19 kD, 22 kD, 27 kD, and gamma genes) (Pedersen et al., *Cell* 29: 1015–1026 (1982), herein incorporated by reference in its entirety) can be also used. The zeins are a group of storage proteins found in maize endosperm.

Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., *Mol. Cell Biol.* 13: 5829–5842 (1993), herein incorporated by reference in its entirety). Examples of promoters suitable for expression in wheat include those promoters for the ADPglucose pyrophosphorylase (AD-PGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

A tomato promoter active during fruit ripening, senescence and abscission of leaves and, to a lesser extent, of flowers can be used (Blume et al., *Plant J.* 12:731–746 (1997), herein incorporated by reference in its entirety). Other exemplary promoters include the pistol specific promoter in the potato (*Solarium tuberosum* L.) SK2 gene, encoding a pistil-specific basic endochitinase (Ficker et al., *Plant Mol. Biol.* 35:425–431 (1997), herein incorporated by reference in its entirety); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots. The tissue specific E8 promoter from tomato is also useful for directing gene expression in fruits.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., *The Plant Cell* 1:977–984 (1989), herein incorporated by reference in its entirety). It is further recognized that since in most cases the exact boundaries of regulatory sequences have not been completely defined, DNA fragments of different lengths may have identical promoter activity.

"For example" means an instance serving to illustrate a precept or to act as an exercise, and is not inclusive of all the possible examples, or embodiments, and acts as only a single representative of a much larger class.

"i.e." or "e.g." means in (for) example and can be read as "for example".

The "translation leader sequence" means a DNA sequence located between the promoter sequence of a gene and the coding sequence. The translation leader sequence is present in the fully processed mRNA upstream of the translation start sequence. The translation leader sequence may affect processing of the primary transcript to MRNA, MRNA stability or translation efficiency. Examples of translation leader sequences have been described (Turner and Foster, *Molecular Biotechnology* 3:225 (1995), herein incorporated by reference in its entirety).

The "3' non-translated sequences" means DNA sequences located downstream of a structural nucleotide sequence and include sequences encoding polyadenylation and other regulatory signals capable of affecting MRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (NOS 3'; Fraley et al., *Proc. Natl. Acad. Sci. USA* 80: 4803–4807 (1983), herein incorporated by reference in its entirety). The use of different 3' non-translated sequences is exemplified by Ingelbrecht et al., *Plant Cell* 1:671–680 (1989), herein incorporated by reference in its entirety.

"Propogule" includes all products of meiosis and mitosis, including but not limited to, seed and parts of the plant able to propogate a new plant. For example, propogule includes a shoot, root, or other plant part that is capable of growing into an entire plant. Propogule also includes grafts where one portion of a plant is grafted to another portion of a different plant (even one of a different species) to create a living organism. Propogule also includes all plants and seeds produced by cloning or by bringing together meiotic products, or allowing meiotic products to come together to form an embryo or fertilized egg (naturally or with human intervention).

The isolated nucleic acid molecules of the present invention may also include introns. Generally, optimal expression in monocotyledonous and some dicotyledonous plants is obtained when an intron sequence is inserted between the promoter sequence and the structural gene sequence or, optionally, may be inserted in the structural coding sequence to provide an interrupted coding sequence. An example of such an intron sequence is the HSP 70 intron described in WO 93/19189, herein incorporated by reference in its entirety.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

Another aspect of the present invention relates to an isolated nucleic acid molecule having a nucleotide sequence selected from the group consisting of SEQ ID NOS: 1, 3, 5, 7, 8, 10, and 12 or complements thereof, that contains DNA markers. DNA markers of the present invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and muti-allelic, codominant markers often become more informative of the genotype than dominant markers. Examples of DNA markers include restriction fragment length polymorphism (RFLP), random amplified fragment length polymorphism (RAPD), simple sequence repeat polymorphism (SSR), cleavable amplified polymorphic sequences (CAPS), amplified fragment length polymorphism (AFLP), and single nucleotide polymorphism (SNP).

DNA markers can be developed from nucleic acid molecules using restriction endonucleases, the PCR and/or DNA sequence information. Methods for isolating DNA markers are well known in the art (see for example, Birren and Lai, *Nonmammalian Genomic Analysis*, Academic Press, Inc, San Diego, Calif., USA; London, England, UK, pp. 75–134 (1996); Brown et al., *Methods of Genome Analysis in Plants*, ed. Jauhar, CRC Press, Inc, Boca Raton, Fla., USA; London, England, UK (1996), both of which are herein incorporated by reference in their entirety).

RFLP markers are codominant and highly abundant in plant genomes and have a medium level of polymorphism. RFLP is resulted from single base changes or insertions/deletions. The RFLP markers can be developed by a combination of restriction endonuclease digestion and Southern blotting hybridization.

CAPSs are codominant markers and highly abundant in plant genomes and have a medium level of polymorphism. CAPS is resulted from single base changes and insertions/deletions. The CAPs markers can be developed from restriction endonuclease digestion of PCR products.

RAPDs are dominant markers and very highly abundant in plant genomes and have a medium level of polymorphism. RAPD is result from single base changes and insertions and deletions in plant genomes. The RAPDs markers can be developed from DNA amplification with random primers.

AFLP markers are both dominant and codominant. They are highly abundant in plant genomes and exhibit a medium level of polymorphism. AFLP is resulted from single base changes, insertions, and deletions. The AFLP markers can be developed by PCR of a subset of restriction fragments from extended adapter primers.

SSR is resulted from repeat length changes. SSR markers are codominant and exhibit a medium degree of abundance in plant genomes and a high level of polymorphism. On average, 1 SSR is found every 21 and 65 kb in dicots and monocots. Fewer CG nucleotides are found in dicots than in monocots. There is no correlation between abundance of SSRs and nuclear DNA content. The abundance of all tri and tetranucleotide SSR combination jointly have been reported to be equivalent to that of the total di-nucleotide combinations. Mono- di- and tetra-nucleotide repeats are all located in noncoding regions of DNA while 57% of those trinucleotide SSRs containing CG were located within gene coding regions. All repeated trinucleotide SSRs composed entirely of AT are found in noncoding regions, (Brown et al., *Methods of Genome Analysis in Plants*, ed. Jauhar, CRC Press, Inc, Boca Raton, Fla., USA; London, England, UK, pp. 147–159, (1996)).

The development of SSRs requires DNA sequence information. SSRs can be identified in SEQ NOS: 1, 3, 5, 7, 8, 10, and 12 or complements thereof by using the BLASTN program to examine sequences for the presence/absence of SSRs.

SNP is resulted from single base changes. They are highly abundant and exhibit a myriad of polymorphism (Rafalski, et al., In: *Nonmammalian Genomic Analysis*, ed. Birren and Lai, Academic Press, San Diego, Calif., pp. 75–134 (1996), the entirety of which is herein incorporated by reference). Development of SNPs also requires DNA sequence information.

Isolation and identification of nucleic acid molecules encoding ANT-like polypeptides from soybean, corn, rice and cotton are described in detail in Examples. All or a substantial portion of the nucleic acid molecules of the present invention may be used to isolate cDNAs and nucleic acid molecules encoding homologous polypeptides from the same or other plant species.

A "substantial portion" of a nucleotide sequence comprises enough of the sequence to afford specific identification and/or isolation of a nucleic acid molecule comprising the sequence. Nucleotide sequences can be evaluated either manually by one skilled in the art, or by using computer based sequence comparison and identification tools that employ algorithms such as BLAST (Basic Local Alignment Search Tool; Altschul et al. *J Mol. Biol.* 215:403–410 (1993); see also www.ncbi.nlm.nih.gov/BLAST/). In general, a sequence of thirty or more contiguous nucleotides is necessary in order to putatively identify a nucleotide sequence as homologous to a gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid molecule comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Isolation of nucleic acid molecules encoding homologous polypeptides using sequence-dependent protocols is well known in the art. Examples of sequence-dependent protocols include, but are not limited to, methods of nucleic acid molecule hybridization, and methods of DNA and RNA amplification as exemplified by various uses of nucleic acid molecule amplification technologies (e.g., polymerase chain reaction, ligase chain reaction).

For example, structural nucleic acid molecules encoding other ANT-like polypeptide, either as cDNAs or genomic DNAs, could be isolated directly by using all or a substantial portion of the nucleic acid molecules of the present invention as DNA hybridization probes to screen cDNA or genomic libraries from any desired plant employing methodology well known to those skilled in the art. Methods for forming such libraries are well known in the art. Specific oligonucleotide probes based upon the nucleic acid molecules of the present invention can be designed and synthesized by methods known in the art. Moreover, the entire sequences of the nucleic acid molecules can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full length cDNA or genomic DNAs under conditions of appropriate stringency.

Alternatively, the nucleic acid molecules of interest can be amplified from nucleic acid samples using amplification techniques. For instance, the disclosed nucleic acid molecules may be used to define a pair of primers that can be used with the polymerase chain reaction (Mullis, et al., *Cold Spring Harbor Symp. Quant. Biol.* 51:263–273 (1986); Erlich et al., EP 50,424; EP 84,796; EP 258,017, EP 237,362; Mullis, EP 201,184; Mullis et al., U.S. Pat. No. 4,683,202; Erlich, U.S. Pat. No. 4,582,788; and Saki, R. et al., U.S. Pat. No. 4,683,194, all of which are herein incorporated by reference in their entireties) to amplify and obtain any desired nucleic acid molecule directly from mRNA, from cDNA, from genomic libraries or cDNA libraries. PCR and other in vitro amplification methods may also be useful, for example, to clone nucleotide sequences that encode for polypeptides to be expressed, to make nucleic acid molecules to use as probes for detecting the presence of the desired mRNA in samples, for nucleic acid sequencing, or for other purposes.

In addition, two short segments of the nucleic acid molecules of the present invention may be used in polymerase chain reaction protocols to amplify longer nucleic acid molecules encoding homologues of an ANT-like polypeptide from DNA or RNA. For example, the skilled artisan can follow the RACE protocol (Frohman et al., Proc. Natl. Acad. Sci. USA 85:8998 (1988), herein incorporated by reference in its entirety) to generate cDNAs by using PCR to amplify copies of the region between a single point in the transcript and the 3' or 5' end. Primers oriented in the 3' and 5' directions can be designed from the nucleic acid molecules of the present invention. Using commercially available 3'RACE or 5'RACE systems (Gibco BRL, Life Technologies, Gaithersburg, Md. U.S.A.), specific 3' or 5' cDNA fragments can be isolated (Ohara et al., Proc. Natl. Acad. Sci. USA 86:5673 (1989); Loh et al., Science 243:217 (1989), both of which are herein incorporated by reference in their entireties). Products generated by the 3' and 5' RACE procedures can be combined to generate full-length cDNAs (Frohman and Martin, Techniques 1: 165 (1989), herein incorporated by reference in its entirety).

Nucleic acid molecules of interest may also be synthesized, either completely or in part, especially where it is desirable to provide plant-preferred sequences, by well-known techniques as described in the technical literature. See, e.g., Carruthers et al., Cold Spring Harbor Symp. Quant. Biol. 47:411–418 (1982), and Adams et al., J. Am. Chem. Soc. 105:661 (1983), both of which are herein incorporated by reference in their entireties. Thus, all or a portion of the nucleic acid molecules of the present invention may be synthesized using codons preferred by a selected plant host. Plant-preferred codons may be determined, for example, from the codons used most frequently in the proteins expressed in a particular plant host species. Other modifications of the gene sequences may result in mutants having slightly altered activity.

Availability of the nucleotide sequences encoding ANT-like polypeptides facilitates immunological screening of cDNA expression libraries. Synthetic polypeptides representing portions of the amino acid sequences of ANT-like polypeptides may be synthesized. These polypeptides can be used to immunize animals to produce polyclonal or monoclonal antibodies with specificity for polypeptides comprising the amino acid sequences. These antibodies can be then be used to screen cDNA expression libraries to isolate full-length cDNA clones of interest (Lerner, Adv. lnmunol. 36: 1 (1984); Sambrook et al., Molecular Cloning: A Laboratory Manual; Cold Spring Harbor Laboratory Press: Cold Spring Harbor, (1989)). It is understood that people skilled in the art are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988)).

Another aspect of the present invention relates to methods for obtaining a nucleic acid molecule comprising a nucleotide sequence encoding an ANT-like polypeptide the amino acid sequence of which has at least 60% sequence identity to a member selected from the group consisting of SEQ ID Nos: 2, 4, 6, 9, 11, and 13. One method of the present invention for obtaining a nucleic acid molecule encoding all or a substantial portion of the amino acid sequence of an ANT-like polypeptide comprising: (a) probing a cDNA or genomic library with a hybridization probe comprising a nucleotide sequence encoding all or a substantial portion of a polypeptide having an amino acid sequence set forth in any of SEQ ID Nos: 2, 4, 6, 9, 11, and 13 or an amino acid sequence set forth in any of SEQ ID Nos: 2, 4, 6, 9, 11, and 13 with conservative amino acid substitutions; (b) identifying a DNA clone that hybridizes under stringent conditions to the hybridization probe; (c) isolating the DNA clone identified in step (b); and (d) sequencing the cDNA or genomic fragment that comprises the clone isolated in step (c) wherein the sequenced nucleic acid molecule encodes all or a substantial portion of the amino acid sequence of the ANT-like polypeptide.

Another method of the present invention for obtaining a nucleic acid molecule encoding all or a substantial portion of the amino acid sequence of an ANT-like polypeptide comprising: (a) synthesizing a first and a second oligonucleotide primers, wherein the sequences of the first and second oligonucleotide primers encode two different portions of a polypeptide having an amino acid sequence selected from the group consisting of SEQ ID Nos: 2, 4, 6, 9, 11, and 13; and (b) amplifying and obtaining the nucleic acid molecule directly from mRNA samples, from genomic libraries or from cDNA libraries using the first and second oligonucleotide primers of step (a) wherein the nucleic acid molecule encodes all or a substantial portion of the amino acid sequence of the ANT-like polypeptide.

The isolated nucleic acid molecules of the present invention can also be used in antisense technology to suppress endogenous ANT-like gene expression. To accomplish this, a nucleic acid molecule derived from a nucleotide sequence selected from the group consisting of SEQ ID NO: 1, 3, 5, 7, 8, 10, and 12 is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest (see, e.g., Sheehy et al., *Proc. Nat. Acad. Sci. USA* 85:8805–8809 (1988), and U.S. Pat. No. 4,801, 340; both of which are herein incorporated by reference in their entireties).

The nucleic acid segment to be introduced generally will be substantially identical to at least a portion of the endogenous ANT-like gene or genes to be repressed. The sequence, however, need not be perfectly identical to inhibit expression. The recombinant vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may he equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of ANT-like genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the recombinant DNA constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff et al. *Nature* 334:585–591 (1988), herein incorporated by reference in its entirety.

The isolated nucleic acid molecules of the present invention can also be used in sense cosuppression to modulate expression of endogenous ANT-like genes. The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed MRNA. This may be preferred to avoid concurrent production of some plants which are overexpressed. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Changes in plant phenotypes can be produced by specifically inhibiting expression of one or more genes by antisense inhibition or cosuppression (U.S. Pat. Nos. 5,190,931, 5,107,065 and 5,283,323, herein incorporated by reference in their entireties). An antisense or cosuppression construct would act as a dominant negative regulator of gene activity. While conventional mutations can yield negative regulation of gene activity, these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenic plants for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the polypeptide encoded by the gene being suppressed, or one could establish assays that specifically measure enzyme activity. A preferred method will be one which allows large numbers of samples to be processed rapidly, since it will be expected that a large number of transformants will be negative for the desired phenotype.

All or a substantial portion of the nucleic acid molecules of the present invention may also be used as probes for genetically and physically mapping the genes that they are a part of, and as markers for traits linked to those genes. Such information may be useful in plant breeding in order to develop lines with desired phenotypes. For example, the nucleic acid molecules of the present invention may be used as restriction fragment length polymorphism (RFLP) markers. Southern blots (Maniatis et al., Molecular Cloning: A Laboratory Manual, Second Edition (1989) Cold Spring Harbor Laboratory, Cold Spring Harbor, N.Y., herein incorporated by reference in its entirety) of restriction-digested plant genomic DNA may be probed with the nucleic acid fragments of the present invention. The resulting banding patterns may then be subjected to genetic analyses using computer programs such as MapMaker (Lander et al., *Genomics* 1:174–181 (1987), herein incorporated by reference in its entirety) in order to construct a genetic map. In addition, the nucleic acid fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the nucleotide sequence of the present invention in the genetic map previously obtained using this population (Botstein et al., *Am. J. Hum. Genet.* 32:314–331 (1980), herein incorporated by reference in its entirety).

The production and use of plant gene-derived probes for use in genetic mapping is described in Bernatzky and Tanksley, *Plant Mol. Biol. Reporter* 4:3741 (1986), herein incorporated by reference in its entirety. Numerous publications describe genetic mapping of specific cDNA clones using the methodology outlined above or variations thereof. For example, F2 intercross populations, backcross populations, randomly mated populations, near isogenic lines, exotic germplasms, and other sets of individuals may be used for mapping. Such methodologies are well known to those skilled in the art.

Nucleic acid probes derived from the nucleic acid molecules of the present invention may also be used for physical mapping (i.e., placement of sequences on physical maps; see Hoheisel et al., In: Nonmammalian Genomic Analysis: A Practical Guide, Academic press 1996, pp. 319–346, and references cited therein).

In another embodiment, nucleic acid probes derived from the nucleic acid molecules of the present invention may be used in direct fluorescence in situ hybridization (FISH) mapping (Trask, *Trends Genet.* 7:149–154 (1991), herein incorporated by reference in its entirety). Although current methods of FISH mapping favor use of large clones (several to several hundred KB; see Laan et al, *Genome Res.* 5:13–20 (1995), herein incorporated by reference in its entirety), improvements in sensitivity may allow performance of FISH mapping using shorter probes.

A variety of nucleic acid amplification-based methods of genetic and physical mapping may be carried out using the nucleotide molecules of the present invention. Examples include allele-specific amplification (Kazazian et al., *J. Lab. Clin. Med.* 11:95–96 (1989), herein incorporated by reference in its entirety), polymorphism of PCR-amplified fragments (CAPS; Sheffield et al., *Genomics* 16:325–332 (1993), herein incorporated by reference in its entirety), allele-specific ligation (Landegren et al., *Science* 241:1077–1080 (1988) herein incorporated by reference in its entirety), nucleotide extension reactions (Sokolov et al., *Nucleic Acid Res.* 18:3671 (1990) herein incorporated by reference in its entirety), Radiation Hybrid Mapping (Walter et al., *Nat. Genet.* 7:22–28 (1997) herein incorporated by reference in its entirety) and Happy Mapping (Dear and Cook, *Nucleic Acid Res.* 17:6795–6807 (1989) herein incorporated by reference in its entirety). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the nucleotide sequence. This, however, is generally not necessary for mapping methods.

Isolated nucleic acid molecules of the present invention may find use in the identification of loss of function mutant phenotypes of a plant, due to a mutation in one or more endogenous genes encoding the ANT-like polypeptides. This can be accomplished either by using targeted gene disruption protocols or by identifying specific mutants for these genes contained in a population of plants carrying mutations in all possible genes (Ballinger and Benzer, *Proc. Natl. Acad Sci USA* 86:9402–9406 (1989); Koes et al., *Proc. Natl. Acad. Sci. USA* 92:8149–8153 (1995); Bensen et al., *Plant Cell* 7:75–84 (1995) all of which are incorporated herein by reference in their entirety). The latter approach may be accomplished in two ways. First, short segments of the nucleic acid molecules of the present invention may be used in polymerase chain reaction protocols in conjunction with a mutation tag sequence primer on DNAs prepared from a population of plants in which mutator transposons or some other mutation-causing DNA element has been introduced. The amplification of a specific DNA fragment with these primers indicates the insertion of the mutation tag element in or near the plant gene encoding ANT-like polypeptides. Alternatively, the nucleic acid molecules of the present invention may be used as a hybridization probe against PCR amplification products generated from the mutation population using the mutation tag sequence primer in conjunction with an arbitrary genomic site primer, such as that for a restriction enzyme site-anchored synthetic adapter. With either method, a plant containing a mutation in the endogenous gene encoding the ANT-like polypeptides can be identified and obtained. This mutant plant can then be used to determine or confirm the natural function of the ANT-like polypeptides disclosed herein.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Methods for determining gene expression, even expression of a gene from an introduced transgene are common in the art, and include RT-PCR, Northern blots, and Taqman®. Taqman® (PE Applied Biosystems, Foster City, Calif.) is described as a method of detecting and quantifying the presence of a DNA or RNA/cDNA molecule and is fully described in the instructions provided by the manufacturer, and at their website. Briefly, in the case of a genomic sequence a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert DNA due to successful amplification and hybridization.

Substantially Purified Polypeptides

The present invention, in another aspect, provides a substantially purified polypeptide the amino acid sequence of which comprises in the N-terminal to C-terminal direction two AP2 DNA binding domains followed in the C-terminal by an amino acid subsequence selected from group consisting of Xaa-Ser-Ser-Ser-Arg-Glu (SEQ ID NO: 25), Xaa-Ser-Asn-Ser-Arg-Glu (SEQ ID NO: 26), and Asn-Ser-Ser-Ser-Arg-Asn (SEQ ID NO: 27), preferably selected from the group consisting of Ser-Ser-Leu-Xaa-Thr-Ser-Xaa-Ser-Ser-Ser-Arg-Glu (SEQ ID NO: 28), Ser-Ser-Leu-Xaa-Pro-Ser-Xaa-Ser-Asn-Ser-Arg-Glu (SEQ ID NO: 29), Ser-Ser-Leu-Xaa-Thr-Ser-Xaa-Ser-Asn-Ser-Arg-Glu (SEQ ID NO: 30), and Ser-Leu-Xaa-Asn-Ser-Ser-Ser-Arg-Asn (SEQ ID NO: 31) wherein Xaa is an amino acid residue having an aliphatic side chain and selected from the group consisting of Gly, Ala, Val, Leu, and Ile. In a particular preferred embodiment, the substantially purified polypeptide of the present invention further comprises a second amino acid subsequence selected from the group consisting of Leu-Gly-Phe-Ser-Leu-Ser (SEQ ID NO: 35), Leu-Gly-Phe-Ser-Leu-Thr (SEQ ID NO: 36), Met-Pro-Leu-Lys-Ser-Asp-Gly-Ser (SEQ ID NO: 37), Met-Pro-Leu-Arg-Ser-Asp-Gly-Ser (SEQ ID NO: 38), Met-Pro-Ile-Lys-Ser-Asp-Gly-Ser (SEQ ID NO: 39), Pro-Lys-Leu-Glu-Asp-Phe (SEQ ID NO: 40), and Pro-Lys-Val-Glu-Asp-Phe (SEQ ID NO: 41). In some groups of amino acids, the side chains are described as having aliphatic side chains. Aliphatic side chains are often designated as a side chain of organic chemical compounds in which the carbon atoms are linked in open chains, for example Gly, Ala, Val, Leu, and Ile.

The present invention, in another aspect, provides a substantially purified polypeptide the amino acid sequence of which is encoded by a first nucleotide sequence which specifically hybridizes under stringent conditions to the complement of a second nucleotide sequence selected from the groups consisting of SEQ ID NO: 1, 3, 5, 7, 8, 10, and 12.

The present invention, in another aspect, provides a substantially purified polypeptide the amino acid sequence of which is encoded by a nucleotide sequence that has at least 60% sequence identity, preferably at least 70% or 75% sequence identity, more preferably at least 80% or 85% sequence identity, even more preferably at least 90% or 95% sequence identity, most preferably at least 98% sequence identity to a member selected from the group consisting of SEQ ID NOs: 1, 3, 5, 7, 8, 10, and 12.

The present invention, in another aspect, provides a substantially purified polypeptide the amino acid sequence of which has at least 60% sequence identity, preferably at least 70% or 75% sequence identity, more preferably at least 80% or 85% sequence identity, even more preferably at least 90% or 95% sequence identity, and most preferably at least 98% sequence identity to a sequence selected from the group consisting of SEQ ID Nos: 2, 4, 6, 9, 11, and 13.

The polypeptides of the present invention may be produced via chemical synthesis, or more preferably, by expression in a suitable bacterial or eukaryotic host. Suitable methods for expression are described by Sambrook, et al., (In: *Molecular Cloning, A Laboratory Manual, 2nd Edition, Cold Spring Harbor Press*, Cold Spring Harbor, N.Y. (1989)), herein incorporated by reference in its entirety), or similar texts.

The polypeptides of the present invention may also include fusion polypeptides. A polypeptide that comprises one or more additional polypeptide regions not derived from that polypeptide is a "fusion" polypeptide. Such molecules may be derivatized to contain carbohydrate or other moieties (such as keyhole limpet hemocyanin, etc.). Fusion polypeptide of the present invention are preferably produced via recombinant means.

The polypeptide molecules of the present invention may also include polypeptides encoded by all or a substantial portion of polypeptide-encoding sequences set forth in SEQ ID NOs: 1, 3, 5, 7, 8, 10, and 12 or complements thereof or, fragments or fusions thereof in which conservative, non-essential, or not relevant, amino acid residues have been added, replaced, or deleted. An example of such a homologue is the homologue polypeptide (or protein) from different species. Such a homologue can be obtained by any of a variety of methods. For example, as indicated above, one or more of the disclosed sequences (all or a substantial portion of a polypeptide-encoding sequences selected from the group consisting of SEQ ID NOs: 1, 3, 5, 7, 8, 10, and 12 and complements thereof) will be used to define a pair of primers that may be used to isolate the homologue-encoding nucleic acid molecules from any desired species. Such molecules can be expressed to yield homologues by recombinant means.

Another aspect of the present invention provides antibodies, single-chain antigen binding molecules, or other proteins that specifically bind to the polypeptides of the present invention and their homologues, fusions or fragments thereof. Such antibodies may be used to quantitatively or qualitatively detect the polypeptides of the present invention. As used herein, an antibody is said to "specifically bind" to a polypeptide molecule of the present invention if such binding is not competitively inhibited by the presence of non-related molecules. The antibodies that specifically bind the polypeptides of the present invention may be polyclonal or monoclonal, and may comprise intact immunoglobulins, or antigen binding portions of immunoglobulins (such as (F(ab'), F(ab')$_2$) fragments, or single-chain immunoglobulins producible, for example, via recombinant means). It is understood that practitioners are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988), the entirety of which is herein incorporated by reference).

Nucleic acid molecules that encode all or part of the ANT-like polypeptides of the present invention can be expressed, via recombinant means, to yield polypeptides that can in turn be used to elicit antibodies that are capable of binding the expressed polypeptides. It may be desirable to derivatize the obtained antibodies, for example with a ligand group (such as biotin) or a detectable marker group (such as a fluorescent group, a radioisotope or an enzyme). Such antibodies may be used in immunoassays for that polypeptide. In a preferred embodiment, such antibodies can be used to screen cDNA expression libraries to isolate full-length cDNA clones of ANT-like genes (Lerner, Adv. Immunol. 36: 1 (1984); Sambrook et al., Molecular Cloning: A Laboratory Manual; Cold Spring Harbor Laboratory Press: Cold Spring Harbor, (1989)).

Plant Recombinant DNA Constructs and Transformed Plants

The isolated nucleic acid molecules of the present invention can find particular use in creating transgenic plants in which ANT or ANT-like polypeptides are overexpressed. Overexpression of ANT or ANT-like polypeptides in a plant can increase the size of plant organs, e.g., seeds, fruits, roots, tubers, stems, bulbs and leaves, and thereby lead to improvement in the yield of the plant. It would also be desirable to produce a plant by the overexpression of ANT or ANT-like polypeptides that is itself larger, for example increased height and/or size. It will be particularly desirable to increase seed size, seed proteins, seed oils, and seed carbohydrates in crop plants in which seed areu sed directly for animal or human consumption, or for industrial purposes. Examples of such crops include soybean, canola, rape, cotton (cottonseeds), sunflower, and grains such as corn, wheat, rice, rye, and the like.

The term "transgenic plant" means a plant that contains an exogenous nucleic acid, which can be derived from the same plant species or from a different species. By "exogenous" it is meant that a nucleic acid molecule originates from outside the plant which the nucleic acid molecule is introduced. An exogenous nucleic acid molecule can have a naturally occurring or non-naturally occurring nucleotide sequence. One skilled in the art understands that an exogenous nucleic acid molecule can be a heterologous nucleic acid molecule derived from a different plant species than the plant into which the nucleic acid molecule is introduced or can be a nucleic acid molecule derived from the same plant species as the plant into which it is introduced.

Plant cell, as used herein, includes without limitation, seeds suspension cultures, embryos, meristematic regions, callus tissue, leaves, roots, shoots, gametophytes, sporophytes, pollen and microspores.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

Exogenous nucleic acid molecules may be transferred into a plant cell by the use of a recombinant DNA construct (or vector) designed for such a purpose.

The present invention also provides a plant recombinant DNA construct (or vector) for producing transgenic plants, wherein the plant recombinant DNA construct (or vector) comprises a structural nucleotide sequence encoding an ANT-like polypeptide. Method which are well known to those skilled in the art may be used to prepare the plant recombinant DNA construct (or vector) of the present invention. These method include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1989).

A plant recombinant DNA construct (or vector) of the present invention contains a structural nucleotide sequence encoding an ANT-like polypeptide of the present invention and operably linked regulatory sequences or control elements. Exemplary regulatory sequences include but are not limited to promoters, translation leader sequences, introns, 3' non-translated sequences. The promoters can be constitutive, inducible, or tissue-specific promoters.

A plant recombinant DNA construct (vector) of the present invention will typically comprise a selectable marker which confers a selectable phenotype on plant cells. Selectable markers may also be used to select for plants or plant cells that contain the exogenous nucleic acid molecules encoding polypeptides of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183–188 (1985)) which codes for kanamycin resistance and can be selected for using kanamycin, G418, etc.; a bar gene which codes for bialaphos resistance; a mutant EPSP synthase gene (Hinchee et al., *Bio/Technology* 6:915–922 (1988)) which encodes glyphosate resistance; a nitrilase gene which confers resistance to bromoxynil (Stalker et al., *J. Biol. Chem.* 263: 6310–6314 (1988)); a mutant acetolactate synthase gene (ALS) which confers imidazolinone or sulphonylurea resistance (European Patent Application 154,204 (Sept. 11, 1985)); and a methotrexate resistant DHFR gene (Thillet et al., *J. Biol. Chem.* 263:12500–12508 (1988)).

A plant recombinant DNA construct (vector) of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387–405 (1987); Jefferson et al., *EMBO J.* 6:3901–3907 (1987)); an R-locus gene, which encodes a product that regulates the production of anthocyanin pigments (red color) in plant tissues (Dellaporta et al., Stadler Symposium 11:263–282 (1988)); a β-lactamase gene (Sutcliffe et al., *Proc. Natl. Acad. Sci.* (*U.S.A.*) 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)) a xylE gene (Zukowsky et al., *Proc. Natl. Acad. Sci.* (*U.S.A.*) 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17–19 (1987)) to identify transformed cells.

In preparing the recombinant DNA constructs (vectors) of the present invention, the various components of the construct or fragments thereof will normally be inserted into a convenient cloning vector, e.g., a plasmid that is capable of replication in a bacterial host, e.g., *E. coli*. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A plant recombinant DNA construct (vector) of the present invention may also include a chloroplast transit peptide, in order to target the polypeptide of the present invention to the plastid. The term "plastid" means the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized polypeptides are expressed from nuclear genes as precursors and are targeted to the plastid by a chloroplast transit peptide (CTP), which is removed during the import steps. Examples of such chloroplast polypeptides include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II and thioredoxin F. It has been demonstrated that non-plastid polypeptides may be targeted to the chloroplast by use of polypeptide fusions with a CTP and that a CTP sequence is sufficient to target a polypeptide to the plastid. Those skilled in the art will also recognize that various other recombinant DNA constructs can be made that utilize the functionality of a particular plastid transit peptide to import the enzyme into the plant cell plastid depending on the promoter tissue specificity.

The present invention also provide a transgenic plant comprising in its genome an isolated nucleic acid which comprises: (A) a 5' non-coding sequence which functions in the cell to cause the production of a mRNA molecule; which is operably linked to (B) a structural nucleotide sequence encoding an ANT-like polypeptide of this invention; which is operably linked to (C) a 3' non-translated sequence that functions in said cell to cause termination of transcription. Preferably, the amino acid sequence of the ANT-like polypeptide has at least 60% sequence identity, at least 65% sequence identity, at least 70% sequence identity, or at least 75% sequence identity to a member selected from the group consisting of SEQ ID NOs: 2, 4, 6, 9, 11, and 13. More preferably, the amino acid sequence of the ANT-like polypeptide has at least 80% sequence identity, at least 85% sequence identity, or at least 90% sequence identity to a member selected from the group consisting of SEQ ID NOs: 2, 4, 6, 9, 11, and 13. Even more preferably, the amino acid sequence of the the ANT-like polypeptide has at least 95% or 98% sequence identity to a member selected from the group consisting of SEQ ID NOs: 2, 4, 6, 9, 11, and 13. Most Preferably, the amino acid sequence of the ANT-like polypeptide is selected from the group consisting of SEQ ID NOs: 2, 4, 6, 9, 11, and 13. The above described polypeptide can also have one of the sequences set forth in SEQ ID NOs: 2, 4, 6, 9, 11, and 13 with conservative amino acid substitutions.

Transgenic plants of the present invention preferably have incorporated into their genome or transformed into their chloroplast or plastid genomes an exogenous nucleic acid molecule (or "transgene"), that comprises at least a structural nucleotide sequence that encodes an ANT-like polypeptide having an amino acid sequence selected from the group consisting of SEQ ID NOs: 2, 4, 6, 9, 11, and 13. Transgenic plants are also meant to comprise progeny (descendant, offspring, etc.) of any generation of such a transgenic plant. A seed of any generation of all such transgenic plants wherein said seed comprises a DNA sequence encoding the ANT-like polypeptide of the present invention is also an important aspect of the invention.

In one embodiment, the transgenic plants of present invention will have increased size of seeds, fruits, roots, tubers, stems, bulbs and leaves due to the overexpression of an exogenous nucleic acid molecule encoding an ANT-like polypeptide. In a preferred embodiment, the transgenic plants of present invention will have increased size of seeds, fruits, roots, and tubers. In a more preferred embodiment, the transgenic plants of present invention will have increased size of seeds and fruits. In a particularly preferred embodiment, the transgenic plants of present invention will have increased size of seeds and proportionally increased contents of seed proteins, seed oils or seed carbohydrates.

The term "increased size", as used herein in reference to an organ (e.g., seed, root, shoot, stem, etc.) of the transgenic plant of the present invention, means that the organ has a significantly greater volume or dry weight or both as compared to the volume or dry weight of same organ of a corresponding wild type plant. It is recognized that there can be natural variation in the size of an organ of a particular plant species. However, the organ of increased size of the trangenic plant of the present invention can be identified by sampling a population of that organs and determining that the normal distribution of the organ sizes is greater, on average, than the normal distribution of the organ sizes of a wild type plant. The volume or dry weight of an organ is, on average, usually at least 5% greater, 10% greater, 30% greater, 50% greater, 75% greater, more usually at least 100% greater, and most usually at least 200% greater than in the corresponding wild type plant species.

The DNA constructs of the present invention may be introduced into the genome of a desired plant host by a variety of conventional transformation techniques, which are well known to those skilled in the art. Preferred methods of transformation of plant cells or tissues are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al., Nature 303:209 (1983); Bevan, Nucleic Acids Res. 12: 8711–8721 (1984); Klee et al., Bio-Technology 3(7): 637–642 (1985); and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a nucleic acid encoding an ANT-like polypeptide in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., Proc. Natl. Acad. Sci. USA 80: 4803–4807(1983)). This expression cassette may be assembled on high copy replicons suitable for the production of large quantities of DNA.

An example of a useful Ti plasmid cassette vector for plant transformation is pMON17227. This vector is described in PCT Publication WO 92/04449, herein incorporated by reference in its entirety, and contains a gene encoding an enzyme conferring glyphosate resistance (denominated CP4), which is an excellent selection marker gene for many plants. The gene is fused to the *Arabidopsis* EPSPS chloroplast transit peptide (CTP2) and expressed from the FMV promoter as described therein. Certain portions of pMON vectors described herein (i.e. in the figures)

have elements described in said PCT publication. All transformation vectors include a left border (LB), right border (RB), orf-7, p-NOS, NOS 3', and a selectable marker, in addition to other element required for propagation in bacteria, insertion into plant genomic DNA, and propagation in callus and mature plants.

When adequate numbers of cells (or protoplasts) containing the exogenous nucleic acid molecule encoding an ANT-like polypeptide are obtained, the cells (or protoplasts) can be cultured to regenerated into whole plants. Such regeneration techniques rely on manipulation of certain phytohormones in a tissue culture growth medium, typically relying on a biocide and/or herbicide marker which has been introduced together with the desired nucleotide sequences. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimamoto et al., Nature 338:274–276 (1989); Fronun, UCLA Symposium on Molecular Strategies for Crop Improvement, Apr. 16–22, 1990. Keystone, Colo. (1990); Vasil et al., Bio/Technology 8:429–434 (1990); Vasil et al., Bio/Technology 10:667–674 (1992); Hayashimoto, Plant Physiol. 93:857–863 (1990); and Datta et al., Bio-technology 8:736–740 (1990). Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regenration techniques are described generally in Klee et al., Ann. Rev. Plant Phys. 38:467–486 (1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seed produced and analyzing the resulting plants produced for the exogenous gene of interest. A explanation of what *Agrobacterium* is, and how it has come to be used in the art can be seen in Box 21.1, p. 1108, in the text *Biochemistry and Molecular Biology of Plants*, editors Buchanan, Gruissem, and Jones, American Society of Plant Physiologists, Rockville, Md. (ISBN 0-943088-39-9).

The development or regeneration of transgenic plants containing the exogenous nucleic acid molecule that encodes a polypeptide of interest is well known in the art. Preferably, the regenerated plants are self-poflinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing a desired ANT-like polypeptide is cultivated using methods well known to one skilled in the art.

Plants that can be made to have increased size of plant organs by practice of the present invention include, but are not limited to, Acacia, alfalfa, aneth, apple, apricot, artichoke, arugula, asparagus, avocado, banana, barley, beans, beet, blackberry blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

Plant organs (e.g., seed) obtained from the transgenic plants of the present invention can be analyzed according to well known procedures to identify organs with desired trait. Increased size can be determined by weighing organs (e.g., seed) or by visual inspection. Protein content is conveniently measured by the method of Bradford et al., Anal. Biochem. 72: 248 (1976). Oil content can be determined using NIR spectroscopy or standard procedures such as gas chromatography.

The present invention also provides parts of the transgenic plants of the present invention. Plant parts, without limitation, include seed, endosperm, ovule and pollen. In a particularly preferred embodiment of the present invention, the plant part is a seed.

The present invention also further provides method for generating a transgenic plant having increased size of one or more plant organs, the method comprising the steps of: a) introducing into the genome of the plant an exogenous nucleic acid molecule comprising in the 5' to 3' direction i) a promoter that functions in the cells of said plant, said promoter operably linked to; ii) a structural nucleotide sequence encoding an ANT-like polypeptide the amino acid sequence of which is substantially identical to a member selected from the group consisting of SEQ ID Nos: 2, 4, 6, 9, 11, and 13, said structural nucleotide sequence operably linked to; iii) a 3' non-translated nucleotide sequence that functions in said cells of said plant to cause transcriptional termination; b) obtaining transformed plant cells containing the nucleotide sequence of step (a); and c) regenerating from said transformed plant cells a transformed plant in which said ANT-like polypeptide is overexpressed.

Larger seeds, or seeds with different characteristics than normal (i.e. increased or decreased starch, sugar, or oil) of plants can be used to improve the efficiency of many processes in industrial plants. For example, ethanol can be produced from corn or other starchy grain. The grain is first ground into meal and then is slurried with water to form a mash. Enzymes are added to the mash to convert the starch to the simple sugar, dextrose. Ammonia is also added for pH control and as a nutrient to the yeast. The mash is processed through a high temperature, cook step to reduce bacteria levels ahead of fermentation. The mash is cooled and transferred to the fermenters where yeast is added and the conversion of sugar to ethanol and carbon dioxide begins. After fermentation, the resulting "beer" is transferred to distillation where the ethanol is separated from the residual "stillage". The ethanol is concentrated to 190 proof using conventional distillation and then is dehydrated to approximately 200 proof in a molecular sieve system. After this anhydrous ethanol is blended with about 5% denaturant and it is ready for shipment to gasoline terminals or retailers. The above process is known as "dry milling", there is also a process called "wet milling". Larger seeds, or seeds with more starch, might be expected to create a greater per seed yield of ethanol that conventional seeds.

The United States and the rest of the world use corn primarily as livestock feed. 67% of the world corn production in 1997 was consumed as animal feed. In the United States, corn represents 86% of the grain used as feed. Dent corn is the most important commercial type of corn grown in the United States. Predominantly yellow or white, the dent corn kernel forms a dent on the crown of the kernel at maturity. Other major commercial types of corn include: flint corn, sweet corn, and popcorn. Specialty corns grown commercially in the United States include waxy corn, high-amylose corn, high-oil corn, and high-lysine corn. The corn or other seed produced as part of the present invention could be used as feed corn, and might be expected to carry more net value per seed than conventional, non-transgenic seed.

The following examples are provided to better elucidate the practice of the present invention and should not be interpreted in any was to limit the scope of the present invention. Those skilled in the art will recognize that various modifications, truncations, etc., can be made to the methods and genes described herein while not departing from the spirit and scope of the present invention. In the following examples references to proprietary database and proprietary libraries, e.g., of DNA clones, describe private databases and libraries available to the inventors from Monsanto Biotechnology LLC.

EXAMPLE 1

This example illustrates how cDNA clones encoding soybean ANT-like polypeptides were identified and isolated.

To identify soybean ANT-like genes in propriety databases, a similarity analysis using the BLAST software (Basic Local Alignment Search Tool, Altschul et al., J. Mol. Biol. 215:403–410 (1990), herein incorporated by reference in its entirety) was performed. The amino acid sequence of the *Arabidopsis* ANT (g1244708) polypeptide was used as a query to search and align soybean DNA databases that were translated in all six reading frames, using the TBLASTN algorithm provided by the NCBI. Such similarity analysis of the proprietary databases resulted in the identification of numerous ESTs and cDNA contigs which have E value as high as 8.00E-92, or a P score as high as 337, with the alignment predominantly limited to the AP2 DNA binding domain.

To determine whether the identified clones comprise coding sequences encoding the homologues of the *Arabidopsis* ANT, all the hits were subjected to contig assembly using the GCG Assembly algorithm provided by Incyte Genomics, Inc. (Palo Alto, Calif.), which resulted in the formation of 36 contigs for the top 100 hits. Seven clones, LIB3242-515-P1-J1-C1, LIB3242-362-Q1-J1-B1, LIB3242-345-Q1-J1-F1, LIB3209-010-Q1-B1-B7, LIB3242-690-P1-J1-E6, LIB3139-020-P1-N1-D12, AND 701124935H1, each containing a putative ATG start codon and each representing one of the top seven contigs with respect to similarity to the *Arabidopsis* ANT, were chosen for full-length insert sequencing. The subsequent alignment of the obtained full-length sequences with the *Arabidopsis* ANT polypeptide showed that they share little similarity to the *Arabidopsis* ANT outside the AP2 DNA binding domain, suggesting that those sequences are not likely ANT-like polypeptide coding sequences.

Considering the fact the AP2 DNA binding domain-containing genes represent a large family of plant genes with highly conserved AP2 DNA-binding domain, it would be unlikely that ANT-like polypeptide coding sequence could be faithfully identified by conventional BLAST search for top hits. This could explain why the top blast hits in the above standard sequence comparison might not be ANT-like polypeptide coding sequences. The inventors of the present invention predicted that the functional (transcriptional activating) domains are likely to reside in the flanking sequences and sequence similarity in such regions with the *Arabidopsis* ANT might be expected for genes performing similar functions.

Based on the assumption, all hits with a E value below 1E-7 were analyzed to look for sequence similarity to the N-terminal of the *Arabidopsis* ANT polypeptide before the two AP2 DNA binding domains. Three sequences (ESTs) were identified, which rank $45^{th}$, $61^{st}$, and $66^{th}$, respectively, in the BLAST list, all of three sequences showing modest similarity (E value ranging from 2.00E-15 to 4.00E-10) to the sequence of the N-terminal before the two AP2 DNA binding domains of the *Arabidopsis* ANT polypeptide. Two of these three sequences were subsequently linked together using sequence contig analysis. A second round of BLAST was performed using the identified ESTs as queries, which resulted in the identification of two potentially full-length cDNAs (containing a putative ATG translation start), namely LIB3242-100-Q1-J1-E2 (plasmid CPR67663) and LIB3242-078-P1-J1-F10 (plasmid CPR67626). When cDNA libraries are primed with poly-dT as a primer, the primer sits on the 3' end of the mRNA. Reverse transcriptase uses this poly-dT as a primer and extends a DNA polynucleotide (often called a cDNA or copy DNA) using the mRNA as a template. Often, the reverse transcriptase does not extend the new DNA polynucleotide the entire length of the mRNA, resulting in truncated transcripts. One way to find putative full length clones is to look for the putative ATG (AUG), the probable translation start site.

The entire inserts of CPR67663 and CPR67626 were sequenced, and the full-length sequences of these two cDNAs were named as GmANT1(SEQ ID NO: 1) and GmANT2 (SEQ ID NO: 3), respectively. GmANT1 and GmANT2 were translated into amino acid sequences (SEQ ID NO: 2 and SEQ ID NO: 4) using the standard genetic code, as shown in the Sequence Listing. Pfam protein domain search showed that both GmANT1 and GmANT2 polypeptides each contain two typical AP2 DNA-binding domains.

Three major observations were made when translated GmANT1, GmANT2 and the conventional top BLAST hits described above were aligned with *Arabidopsis* ANT. First, the two AP2 DNA binding domains of GmANT1 and GmANT2 polypeptides share even better homologies with the *Arabidopsis* ANT polypeptide than the top hits with *Arabidopsis* ANT polypeptide, suggesting that GmANT1 and GmANT2 may have ANT-like activity. Second, by sequence comparison of ANT, GmANT1 and GmANT2 polypeptides, four highly conserved segments were identified in the N-terminal before the AP2 DNA binding domains (FIG. 1), suggesting that these regions may play some functional roles. In addition, they may be used as a signature in identifying other ANT homologs from other plants. Third, the C-terminal sequences of GmANT1 and GmANT2 polypeptides after the AP2 DNA binding domains bear little, if any, homology to that of ANT but they share conserved segments (FIG. 1) with each other, suggesting that those portions of the sequences may not only perform additional or distinguishable function from the *Arabidopsis* ANT polypeptide, but may also be used to identify similar genes that would otherwise be missed if the C-terminal after AP2 DNA binding domains of the *Arabidopsis* ANT polypeptide was used as query sequence. This C-terminal region distinguishes the novel sequences claimed in the present invention from *Arabidopsis* ANT polypeptide and can be used by someone skilled in the art to further identify sequences related to this present invention. For an example of how the cDNA libraries used in this example were constructed, see Example 6.

EXAMPLE 2

This example illustrates how rice ANT-like genes were identified and how a cDNA clone encoding a rice ANT-like polypeptide was isolated.

The N-terminal of 297 amino acid residues of the GmANT1 polypeptide (N-terminal 297 amino acids of SEQ ID NO: 2), which corresponds to the region of amino acid sequence prior to the AP2 DNA binding domains (sometimes referred to herein as "GMANT with AP2 binding domains deleted"), was used as the query sequence to carry out similarity analysis of proprietary rice databases, using similar procedures as described in Example 1. Six rice BAC contigs were identified to contain potential open reading frames with E values ranging from 5e-17 to 9e-07. These six contigs were derived from two chromosomal loci. By comparing open reading frames that encode ANT-like polypeptides, it has been found that the identified six contigs could be represented by two contigs OJ000103__04.0303.C9 and OJ000315__30.0419.C7, respectively, since five of the six contigs all contain an open reading frame that encodes the same ANT-like polypeptide. When using the C-terminal of 200 amino acid residues of GmANT1 after the AP2 DNA binding domains as the query sequence in the similarity analysis of proprietary rice databases, the same six contigs were also identified. However, when the C-terminal of 200 amino acid residues of the *Arabidopsis* ANT polypeptide after the AP2 DNA binding domains was used as the query sequence, the six rice BAC contigs were not identified. A combination of GenScan (Burge and Karlin, J. Mol. Biol. 268: 78–94 (1997), herein incorporated by reference in its entirety) and GenMark (Lukashin and Borodovsky, Nucleic Acid Res. 26: 1107–1115 (1998), herein incorporated by reference in its entirety) algorithms predicted an open reading frame (ORF) from each of the two rice BAC contigs. The software GeneMark.hmm (version 2.2) was used to predict genes/exons. The predicted exons from OJ000103__04.0303.C9 encodes a polypeptide of 540 amino acid residues and the coding sequence was designated as OsANT1, and the predicted exons from OJ000315__30.0419.C7 (SEQ ID NO: 7) encodes a polypeptide of 669 amino acid residues and the coding sequence is designated as OsANT2 (SEQ ID NO: 8).

RT-PCR was performed to isolate the full-length cDNA that might have been transcribed from the above predicted gene OsANTI. Two primers, GAGCGTGTGCATGGTTG-GTG (pOsANT1-10) (SEQ ID NO: 23) and CTCGAG-GCATCTGTCCAGGCTGCAAAAAC (pOsANT1-2) (SEQ ID NO: 24) were designed for RT-PCR cloning, where pOsANTI-10 anneals at –8 upstream to the start of the predicted open reading frame and pOsANT1-2 anneals at the stop of the predicted open reading frame. Total rice RNAs were isolated from roots, leaves and panicles, and were subjected to first-strand cDNA synthesis using Superscript II reverse transcriptase (BRL/Life Technologies Inc., Gaithersburg, Md), using conditions recommended by the manufacturer. The synthesized rice cDNAs were then used as the template for PCR amplification using the gene-specific primers pOsANT1-10 and pOsANT1-2 and the Platinum High Fidelity Taq DNA Polymerase (BRL/Life Technologies Inc., Gaithersburg, Md.). PCR cycling conditions were as follows: 94° C., 40 seconds, followed 30 cycles of 94° C., 25 seconds; 55° C., 30 seconds and 68° C., 2 minutes 30 seconds. The amplification product was verified and purified by agarose gel eletrophoresis. The rice ANT cDNA, named as OsANT1, was amplified from the rice panicle RNAs, but not from that of roots and leaves, suggesting tissue-differential expression of the gene. The purified OsANTI cDNA was then cloned into TA vector (Invitrogen Corporation, San Diego, Calif.), and a PCR-error-free clone was identified by sequencing (sequencing techniques for this and other examples are described in example 23). The coding region (SEQ ID NO:5) of OsANT1 is 1926 bp, which encodes a polypeptide (SEQ ID NO: 6) of 641 amino acid residues. Sequence comparison showed multiple deviations in gene structure of the authentic OsANTI from the predicted one. Polypeptide sequence analysis show that the OsANT1 polypeptide shares high homology with ANT, GmANT1 and GmANT2 polypeptides at the AP2 DNA binding domains, shares conserved segments at the N-terminal, and shares conserved segments with GmANT1 and GmANT2 polypeptides, but not ANT polypeptide, at the C-terminal. For an example of how the cDNA libraries used in this example were constructed, see Example 6.

EXAMPLE 3

This example illustrates how cDNA clones encoding cotton ANT-like polypeptides were identified and isolated.

To identify cotton cDNA clones encoding ANT-like polypeptides, the N-terminal 297 amino acid sequence of GmANT1 was used as the query sequence to search proprietary cotton DNA databases employing a similarity analysis using the BLAST software (Basic Local Alignment Search Tool, Altschul et al., J. Mol. Biol. 215:403–410 (1990), herein incorporated by reference in its entirety) (similar techniques were employed as in Example 1). These databases included EST sequences from cotton. Three proprietary cDNA clones, LIB3582-058-P1-K1-E4, LIB3829-001-Q1-K6-E4 and LIB3582-030-P1-K1-D12, were identified as the only hits that showed appropriate homology, with scores of E=4e-12, 3e-11 and 1e-05, respectively. The first two clones were partial, while the third one, LIB3582-030-P1-K1-D12,appeared to be a full length clone. This determination was made by looking for the start codon, AUG, the putative start codon was only present in clone LIB3582-030-P1-K1-D12. Full length sequence was determined as in example 1. Sequencing confirmed that SEQ ID NO: 10 is a full-length cDNA that shares homology to the *Arabidopsis* ANT polypeptide (FIGS. 1 and 2) both in and outside the AP2 DNA binding domains. This gene was named GhANT1 (FIG. 2; SEQ ID NO: 10). GhANT1 (SEQ ID NO: 10) is 1758 bp in length, encoding a polypeptide (SEQ ID NO: 11) of 585 amino acid residues. For an example of how the cDNA libraries used in this example were constructed, see Example 6.

EXAMPLE 4

This example illustrates how nucleotide sequences encoding maize ANT-like polypeptides were identified.

It was believed by the inventors that using ANT-like genes from monocots instead of their dicot counterparts to search for ANT like sequences in other monocots might lead to better matches as evolutionary divergence would be expected to be less significant. The rice OsANT1 with its AP2 DNA-binding domain deleted (SEQ ID No. 6; OsANT1-AP2 is equivalent to amino acids 1–288 and 457–642 joined together) was used instead of the Gm ANT1 used in example 3. The search was done employing a similarity analysis using the BLAST software (Basic Local Alignment Search Tool, Altschul et al., J. Mol. Biol. 215: 403–410 (1990), herein incorporated by reference in its entirety) of proprietary databases (search was similar to that done in example 1). Such a search identified, in addition to a number of partial genomic DNA sequences, a cDNA clone, LIB3245486-P1-K1-D7, with an E value of 1e-05. The full length insert of this cDNA clone (plasmid CPR82516) was sequenced and designated as ZmANT1 (SEQ ID NO: 12). Sequence analysis indicates that it is a partial coding sequence that encodes the C-terminal of 255 amino acid residues of a corn ANT-like polypeptide (SEQ ID NO: 13), sharing close to 60% sequence identity to the OsANT1 polypeptide (see Table I) For an example of how the cDNA libraries used in this example were constructed, see Example 6.

EXAMPLE 5

Sequence Comparison of ANT and ANT-like Polypeptides

The data in Table 1 represents a calculation of the percentage sequence identity of the amino acid sequences set forth in SEQ ID Nos: 2, 4, 6, 9, 11, and 13 and Arabidopsis ANT polypeptide (gi1244708). Sequence alignments and calculations of percentage sequence identity were performed using Gap in the WISCONSIN PACKAGE version 10.0-UNIX from Genetics Computer Group, Inc. based on the method of Needleman and Wunsch (J. Mol. Biol. 48:443–453 (1970)) using the set of default parameters for pairwise comparison (Gap Creation Penalty=8; Gap Extension Penalty=2). Table 1 shows that the amino acid sequences of the ANT-like polypeptides of the present invention have less than 60% sequence identity to that of the Arabidopsis ANT polypeptide.

The data in Table 2 represents a calculation of the percentage sequence identity of the nucleotide sequences set forth in SEQ ID Nos: 1, 3, 5, 7, 8, 10, and 12 and Arabidopsis ANT (gi1244707). Sequence alignments and percent identity calculations were performed using Gap in the WISCONSIN PACKAGE version 10.0-UNIX from Genetics Computer Group, Inc. based on the method of Needleman and Wunsch (J. Mol. Biol. 48:443–453 (1970)) using the set of default parameters for pairwise comparison (Gap Creation Penalty=50; Gap Extension Penalty=3). Table 2 shows that the nucleotide sequences encoding the ANT-like polypeptides of the present invention have less than 60% sequence identity to the nucleotide sequence encoding the Arabidopsis ANT polypeptide.

The deduced amino acid sequence of the Arabidopsis ANT polypeptide (gi1244708, Klucher et al., Plant Cell 8:137–153 (1996)) is compared with those of the ANT-like polypeptides of the present invention, including GmANT1 and GmANT2 polypeptides from soybean, OsANT1 and OsANT2 polypeptides from rice, GhANT1 polypeptide from cotton, and ZmANT1 polypeptide (partial sequence) from corn (FIG. 2). The multiple alignment was performed using the software CLUSTALW version 1.74 from the public domain (Thompson et al., Nucleic Acids Res. 22:4673–4680 (1994), herein incorporated by reference in its entirety) using default parameters.

FIG. 2 shows that all the ANT-like polypeptides of the present invention and the Arabidopsis ANT polypeptide contain two highly conserved DNA-binding motifs (domains), one located at 281–354, the other at 383–448, with reference to the Arabidopsis ANT polypeptide. The extra 14 amino acid residues of the OsANT2 polypeptide within the second AP2 DNA binding domain is likely a result of inaccurate gene prediction from rice genomic sequences in that region. The comparison also identifies several conserved regions outside the AP2 DNA binding domains, both at the N- and the C-termini. There are at least three regions (shaded) in the N-terminus that are highly conserved across all the ANT-like polypeptides. There are also three conserved regions (shaded) in the C-terminus, with the Arabidopsis ANT polypeptide showing the least homology, especially for the first two regions. All these conserved sequences outside the AP2 DNA binding domain are unique to the ANT-like genes, suggesting that they may be important for ANT-like function, and may be used as the signature sequences in the identification of coding sequences encoding other ANT-like polypeptides.

The relative relatedness (phylogenic tree) of GhANT1, ANT, GmANT1, GmANT2, OsANT1 and ZmANT1 is examined. The multiple alignment was first performed according to the procedure described for FIG. 2 and then the phylogenic tree was constructed using the software PHYLIP (Phylogeny Inference Package) version 3.5c provided as: "Felsenstein, J. 1993. PHYLIP version 3.5c. Distributed by the author. Department of Genetics, University of Washington, Seattle." Subroutines and parameters used were: "seqboot" (parameter: -D 'Molecular sequences' -R 100 -J 'Bootstrap'), "protdist" (parameter: -P 'PAM', -M 'Yes 100'), "kitsch" (parameter: -U 'Yes', -P 2.00000, -L 'No' -R 'No' -S 'No' -J 'No' -M 'Yes, 100' - 'No'), and "consense" (parameter: -R 'Yes').

Genome-wide search suggests that Arabidopsis has only one ANT gene (g1244708), while unexpectedly rice apparently has two ANT-like genes (OsANT1 and OsANT2). The ANT-like genes appear diverged between monocots and dicots and that the cotton GhANT1 may not be the closest ANT-like gene from that species.

EXAMPLE 6

This example illustrates how cDNA libraries (Table 4), which contain cDNA clones identified in Example 1 through Example 4, were constructed.

TABLE 4 cDNA libraries from soybean, cotton, and corn

| Library | Tissue | Clone |
|---|---|---|
| LIB3209 | soybean (variety Asgrow A3244) partially to fully opened flowers | LIB3209-010-Q1-B1-B7 LIB3242-362-Q1-J1-B1 |
| LIB3139 | soybean (variety Asgrow A3244) roots | LIB3139-020-P1-N1-D12 |

TABLE 4-continued cDNA libraries from soybean, cotton, and corn

| Library | Tissue | Clone |
| --- | --- | --- |
| SOYMON019 | soybean (genotype FT108 and Cristilliana) roots | LIB3242-345-Q1-J1-F1<br>LIB3242-100-Q1-J1-E2<br>LIB3242-078-P1-J1-F10 |
| SOYMON032 | re-hydrated dry soybean (variety Asgrow A4922) seed meristem tissue | LIB3242-690-P1-J1-E6 |
| SOYMON038 | soybean (variety Asgrow A3237) | LIB3242-515-P1-J1-C1 |
| SOYMON037 | soybean (genotype A3244) etiolated axis and radical tissue | 701124935H1 |
| LIB3582 | cotton (variety Coker 312) axis from 24 days post anthesis (dpa) seeds | LIB3582-058-P1-K1-E4<br>LIB3582-030-P1-K1-D12 |
| LIB3829 | cotton (variety Nucotton33B) gynoecium from ⅓ grown squares (0.4 cm floral bud) | LIB3829-001-Q1-K6-E4 |
| SATMON012 | corn (genotype DK604) seedlings | LIB3245-486-P1-K1-D7 |

The cDNA library (LIB3209) is generated from soybean cultivar Asgrow 3244 (Asgrow Seed Company, Des Moines, Iowa U.S.A.) partially to fully opened flower tissue. Partially to fully opened flower tissue is harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. A total of 3 grams of flower tissue is harvested and immediately frozen in dry ice. The harvested tissue is then stored at −80° C. until RNA preparation. The RNA is purified from the stored tissue and the cDNA library is constructed as described in Example 21.

The normalized cDNA library (LIB3139) is prepared from soybean cultivar Asgrow 3244 roots harvested from plants grown in a field. Plants are uprooted and roots are quickly rinsed in a pail of water. Roots are then cut from the plants, placed immediately in 14 ml polystyrene tubes and immersed in dry-ice. The collected root samples are then transferred to a −80° C. freezer for storage. A first root sample is collected from 76 plants at the V4 stage; a second root sample (ca. 28 g), from 15 days after flowering (DAF) plants; a third root sample (ca. 61 g), from 25 DAF plants; a fourth root sample (ca. 38 g), from 35 DAF plants; a fifth root sample (ca. 28 g), from 45 DAF plants; a sixth root sample (ca. 22 g), from 55 DAF plants; a seventh root sample (ca. 27 g), from 65 DAF plants; and a eighth root sample (ca. 40 g), from 75 DAF plants. Total RNA (Soy6) is prepared from the first root sample; total RNA (Soy25), from the second root sample; total RNA (Soy29), from the combination of equal amounts of the third and fourth root sample; total RNA (Soy31), from the combination of equal amounts of the fifth and sixth root sample; and total RNA (Soy39), from the combination of equal amounts of the seventh and eighth root sample. The RNA is purified from the stored tissue and four cDNA library are constructed as described in Example 21. Equal amounts of DNA materials from the four cDNA libraries, in the form of double stranded DNA, are mixed and used as the starting material for normalization. Biotinylated genomic soybean DNA is used as the driver for the normalization reaction. Double stranded plasmid DNA representing approximately $1 \times 10^6$ colony forming units is used as the target. The double stranded plasmid DNA is isolated using standard protocols. Approximately 4 micrograms of biotinylated genomic DNA is mixed with approximately 6 micrograms of double stranded plasmid DNA and allowed to hybridize. Genomic DNA-plasmid DNA hybrids are captured on Dynabeads M280 Streptavidin (Dynal Biotech, Oslo, Norway). The dynabeads with captured hybrids are collected with a magnet. Captured hybrids are eluted in water. The resulting clones are subjected to a second round of hybridization identical to the first.

The SOYMON019 cDNA library is generated from soybean cultivars Cristalina (USDA Soybean Germplasm Collection, Urbana, Ill. U.S.A.) and FT108 (Monsoy, Brazil) (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation. The RNA is purified from the stored tissue and the cDNA library is constructed as described in Example 21.

The SOYMON032 cDNA library is prepared from the Asgrow cultivar A4922 (Asgrow Seed Company, Des Moines, Iowa U.S.A.) rehydrated dry soybean seed meristem tissue. Surface sterilized seeds are germinated in liquid media for 24 hours. The seed axis is then excised from the barely germinating seed, placed on tissue culture media and incubated overnight at 20° C. in the dark. The supportive tissue is removed from the explant prior to harvest. Approximately 570 mg of tissue is harvested and frozen in liquid nitrogen. The harvested tissue is then stored at −80° C. until RNA preparation. The RNA is purified from the stored tissue and the cDNA library is constructed as described in Example 21.

The SOYMON038 cDNA library is generated from soybean variety Asgrow A3237 (Asgrow Seed Company, Des Moines, Iowa U.S.A.) rehydrated dry seeds. Explants are prepared for transformation after germination of surface-sterilized seeds on solid tissue media. After 6days, at 28° C. and 18 hours of light per day, the germinated seeds are cold shocked at 4° C. for 24 hours. Meristemic tissue and part of the hypocotyl is remove and cotyledon excised. The prepared explant is then wounded for *Agrobacterium* infection. The 2 grams of harvested tissue is frozen in liquid nitrogen and stored at −80° C. until RNA preparation. The RNA is purified from the stored tissue and the cDNA library is constructed as described in Example 21.

The SOYMON037 cDNA library is generated from soybean cultivar A3244 (Asgrow Seed Company, Des Moines, Iowa U.S.A.) etiolated axis and radical tissue. Seeds are planted in moist vermiculite, wrapped and kept at room temperature in complete darkness until harvest. Etiolated axis and hypocotyl tissue is harvested at 2, 3 and 4 days post-planting. A total of 1 gram of each tissue type is harvested at 2, 3 and 4 days after planting and immediately frozen in liquid nitrogen. The harvested tissue is then stored at −80° C. until RNA preparation. The RNA is purified from the stored tissue and the cDNA library is constructed as described in Example 21.

The LIB3582 cDNA library is generated from 24 dpa (days post anthesis) seed axis harvested from cotton plants. The *Gossypium hirsutum* variety Coker 312 is used for collection. Seeds are planted in trays containing potting soil premixed with fertilizers. Plants are grown in a greenhouse in 16 hr day/8 hr night cycles with an average relative humidity of ca. 50%. Daytime and night time temperature are 90° F. and 74° F. respectively. Daytime light levels are measured at 600–1000 mEinsteins/m². Plants are watered daily in the morning and as needed in the afternoon. Plants receive 1 or 2 applications of Pix to control excessive growth. Bolls are removed from the plants 24 dpa and opened and tissues are divided to harvest seeds. The harvested seeds are dissected to remove axis from other tissues. The harvested axis tissue is immediately frozen in liquid nitrogen and stored at −80° C. until total RNA preparation. The RNA is prepared from the stored tissue and the cDNA library is constructed as described in Example 22.

The LIB3829 cDNA library is prepared from gynoecium tissue from 1/3 grown squares (ca. 0.4 cm floral bud) harvested from cotton plants. The *Gossypium hirsutum* variety Nucotton33B is used for collection. Seeds are planted in trays containing potting soil premixed with fertilizers. Plants are grown in a greenhouse in 16 hr day/8 hr night cycles with an average relative humidity of ca. 50%. Daytime and night time temperature are 90° F. and 74° F. respectively. Daytime light levels are measured at 600–1000 mEinsteins/m². Plants are watered daily in the morning and as needed in the afternoon. Plants receive 1 or 2 applications of Pix to control excessive growth. 1/3 grown squares (ca. 0.4 cm floral bud) are harvested from cotton plants. The harvested squares are dissected to remove gynoecium from other tissues. The harvested gynoecium tissue is immediately frozen in liquid nitrogen and stored at −80° C. until total RNA preparation. The RNA is prepared from the stored tissue and the cDNA library is constructed as described in Example 22.

The SATMON012 cDNA library is generated from 2 day post germination maize (DK604, Dekalb Genetics, Dekalb, Ill. U.S.A.) seedlings. Seeds are planted on a moist filter paper on a covered tray that is kept in the dark until germination (one day). Then the trays containing the seeds are moved to the greenhouse and grown at 15 hr daytime/9 hr nighttime cycles until 2 days post germination. The daytime temperature is approximately 80° F. and the nighttime temperature is approximately 70° F. Tissue is collected when the seedlings are 2 days old. At the two day stage, the coleorhiza is pushed through the seed coat and the primary root (the radicle) is pierced the coleorhiza but is barely visible. Also, at this two day stage, the coleoptile is just emerging from the seed coat. The 2 days post germination seedlings are then immersed in liquid nitrogen and crushed. The harvested tissue is stored at −80° C. until preparation of total RNA. The RNA is purified from the stored tissue and the cDNA library is constructed as described in Example 21.

EXAMPLE 7

Construction of pMON57913 pMON57913 is a binary vector for *Agrobacterium*-mediated transformation and constitutive expression of ANT in *Arabidopsis*. To clone the *Arabidopsis* ANT, two gene specific primers, ANT-1 and ANT-2, were designed based on the ANT sequence information (U41339) from the National Center for Biotechnology Information, which is part of the National Library of Medicine, in turn part of the National Institutes of Health (NCBI). The sequence for ANT-1 is CGCGGCGAATTCATGAAGTCTTTTTGTGATAATG (SEQ ID NO: 14), which anneals at the translational start site of ANT and introduces an EcoRI) site at the 5' end, while the sequence of ANT-2 is CGCGGCGTCGACGAAT-CAGCCCAAGCAGC (SEQ ID NO: 15), which anneals at the last codon of ANT and introduces a SalI site at the end of the primer. RT-PCR was performed to isolate *Arabidopsis* ANT. Specifically, cDNAs were prepared from young *Arabidopsis* seedling RNAs with SuperScript II reverse transcriptase using procedures recommended by the manufacturer (BRL/Life Technologies, Inc., Gainthersburg, Md.). PCR was then performed to amplify the ANT cDNA using the above prepared cDNA as the template, and ANT-1 and ANT-2 as the primers. The thermal cycling conditions were as follows: 94° C., 40 second, followed by 30 cycles of 94° C., 25 seconds; 55° C., 30 seconds and 68° C., 2 minutes 30 seconds. The amplified ANT cDNA was purified by gel-electrophoresis, and ligated to TA cloning vector using procedures recommended by the manufacturer (Invitrogen Corporation, San Diego, Calif.). The ligation mix was transformed into *E. coli* cells for plasmid propagation (Sambrook et al., *Molecular Cloning: A Laboratory Manual, 2ⁿᵈ Edition*, Cold Spring Harbor Press, 1989). The transformed cells were plated on appropiate selective media (Sambrook et al., *Molecular Cloning: A Laboratory Manual, 2ⁿᵈ Edition*, Cold Spring Harbor Press, 1989) and colonies were scored hours or days later. Plasmids were prepared from individual colonies and full-insert sequence was determined.

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y. (1999), the entirety of which is herein incorporated by reference).

To clone ANT into an expression vector, the ANT coding sequence from a clone was released from the TA vector by digesting with EcoRI and SalI. This linear DNA segment was then religated to the binary vector pMON23435, that had been linearized by EcoRI and XhoI, using T4 DNA ligase (BRL/Life Technologies, Inc., Gainthersburg, Md.). The ligation reaction was performed according to the manufacturer's instruction. The resulting plasmid was confirmed by restriction mapping (for example, see Griffiths, et al, *An Introduction to Genetic Analysis, 6ᵗʰ Edition* pp 449–451, ISBN 0-7167-2604-1, W.H. Freeman and Co., New York) and sequencing. As the chosen EcoRI-XhoI cloning site in the vector was flanked by a CaMV e35S promoter at the upstream (5') and an epitope tag (Flag, which encodes the oligo peptide DYKDDDK (SEQ ID NO: 42), SIGMA, St Louis) at the downstream (3'), the *Arabidopsis* ANT in this construct is thus tagged at the C-terminus by the Flag epitope tag and will be driven transcriptionally by the CaMV e35S promoter upon transformation in *Arabidopsis*.

EXAMPLE 8

Construction of pMON57914 pMON57914 was constructed in the same way as for pMON57913 (see Example 7) except that the vector pMON23435 was digested with EcoRI and SalI. It thus contains the ANT gene without the Flag, under the control of the e35S promoter for *Arabidopsis* transformation and constitutive expression.

EXAMPLE 9

Construction of pMON57955 pMON57955 is a binary vector with GmANT1 (SEQ ID NO 2) plus the Flag under the control of the e35S promoter. A pair of PCR primers, GmANT1-1 (SEQ ID NO: 16) and GmANT1-2 (SEQ ID NO: 17), were designed which anneal at the translational start and stop, respectively, with pGmANT1-2 introducing an XhoI site at the end of the coding sequence in order for an in-frame fusion with the Flag, as described in Example 7. These two primers were used to amplify the GmANT1 using the plasmid CPR67663 (see Example 1) as the template. The PCR reaction conditions were as described in Example 7. PCR-amplified GmANT1 was cloned into the TA vector, and from which an error-free clone was identified, using procedures essentially the same as described in Example 7. To clone the GmANT1 gene into a binary vector for plant transformation and expression, the GmANT1-containing TA plasmid was digested with EcoRI and XhoI, and the insert was purified by gel-electrophoresis, which was then ligated to pMON23450 linearized by the same enzymes.

EXAMPLE 10

Construction of pMON57925 pMON57925 is a binary vector with GmANT2 gene plus the Flag at the C-terminus under the control of the CaMV e35S promoter. A pair of PCR primers, GmANT2-1 (Seq ID NO: 18) and GmANT2-2 (SEQ ID NO: 19), were designed which anneal at the translational start and stop, respectively, with pGmANT2-2 introducing an XhoI site at the end of the coding sequence. After digestion with the restriction enzyme XhoI, and religation to the appropriate plasmid an in-frame fusion with the Flag can be created, as described in Example 7. These two primers were used to amplify the GmANT2 using the plasmid CPR67626 (see Example 1) as the template. The PCR reaction conditions, the TA cloning procedure and error-free clone screening were essentially the same as described in Example 9. Once an error-free clone was obtained, GmANT2 was released from the TA vector by digesting with EcoRV and XhoI, followed by purification from the gel. To prepare the binary vector for the cloning of GmANT2, pMON34450 was first digested with BglII, followed by Klenow treatment to blunt the ends and, after inactivation of the enzyme, further digesting the plasmid with XhoL The resulting vector was ligated to the GmANT2 fragment, which was then propagated in *E. coli.*, and a correct clone was identified by restriction mapping and sequencing.

EXAMPLE 11

Construction of pMON57926 pMON57926 is a binary vector with GmANT1 (FIG. 1; SEQ ID NO: 2) plus the Flag under the control of the *Arabidopsis* Napin promoter for seed specific expression (U.S. Pat. No. 6,281,410, for example, see Example 2). To prepare the GmANT1 fragment, the same GmANT1-containing TA vector as described in Example 9 was digested by EcoRV and XhoI. To prepare the expression vector for cloning, pMON57233, which has the Napin promoter and the Flag flanking the cloning site, was first digested with BglIL followed by Klenow treatment to blunt the ends; after inactivation of the Klenow enzyme, the linearized vector was further digested by XhoI, which was then purified and ligated to the prepared GmANT1 gene fragment as in Example 9.

EXAMPLE 12

Construction of pMON57927 pMON57927 is a binary vector in which GmANT2 gene with the Flag at the C-terminus is under the control of the Napin promoter for seed-specific expression. Essentially the same procedure was used in the construction as that in Example 11, except that the GmANT2-containing TA plasmid from Example 10 was used as the GmANT2 source.

EXAMPLE 13

Construction of pMON57928 pMON57928 is a binary vector with the *Arabidopsis* ANT gene plus the Flag under the control of the Napin promoter for seed-specific expression. To prepare the insert, the ANT cassette as described in Example 7 was released from pMON57913 by first digesting with EcoRI, followed by Klenow treatment to blunt the restriction ends. EcoRi creates DNA ends with 5' single stranded DNA overhangs. An enzyme with a DNA polymerization activity (such as the Klenow fragment of DNA polymerase I from *E. Coli*) can be used to add nucleotides to in order to fill in said overhang, creating a "blunt" end (Sambrook et al., *Molecular Cloning: A Laboratory Manual*, $2^{nd}$ Edition, Cold Spring Harbor Press, 1989). The linearized pMON57913 was further digested with SalI, and the released ANT plus Flag was purified by gel-electrophoresis. The binary expression vector containing the Napin promoter was prepared essentially the same way as that for Example 11. The prepared vector and insert were ligated by T4 DNA ligase, and the construction was confirmed by restriction mapping.

EXAMPLE 14

Construction of pMON57930 pMON57930 is a binary vector in which ANT gene plus the Flag is under the control of the RUBISCO small subunit promoter, SSU1A, for shoot-specific expression (U.S. Pat. No. 5,498,830). The ANT cassette was prepared essentially the same way as that of Example 13. The binary expression vector was pMON57231, which contains the promoter SSUIA, followed by cloning sites including NcoI and SalI. PMON57231 was first digested with NcoI, followed by Klenow treatment to generate a blunt end. After inactivation of the Klenow polymerase, the linearized pMON57231 was further digested with SalI, and the resulting vector was purified by gel-electrophoresis. The purified vector was then ligated to the prepared ANT cassette using standard procedures and manufacturer supplied directions as described in Example 7.

EXAMPLE 15

Construction of pMON57931 pMON57931 is a binary vector with ANT gene alone (without the epitope Flag, see example 14 for example with Flag) driven by the pSSU1A promoter for shoot-specific expression in plants. To prepare the ANT coding sequence, pMON57914 as described in Example 8 was first digested by EcoRL followed by treatment with Klenow to generate a blunt-end; after Klenow inactivation, the linearized plasmid was further digested with SalI. The resulting ANT fragment was purified by gel-electrophoresis, and ligated to pMON57231 that was linearized and prepared the same way as that in Example 14.

EXAMPLE 16

Construction of pMON57932 pMON57932 is a binary vector with ANT gene plus the Flag driven by a root-specific promoter, the tobacco RB7 promoter. The ANT cassette was prepared essentially the same as described in Example 13. The binary vector was prepared as follows: pMON57253, which carries the RB7 promoter, was first digested with BglII, followed by Klenow treatment to blunt the end; the linearized plasmid was further digested by SalI followed by gel purification. The prepared ANT gene and the pMON57253 were ligated and clones selected and verified using standard procedures as described in above examples.

EXAMPLE 17

Construction of pMON57933 pMON57933 is a binary vector with ANT gene alone driven by the RB7 promoter for root-specific expression. Identical procedures were used for the construction as that for Example 16, except that the ANT fragment was prepared as described in Example 15.

EXAMPLE 18

Construction of pMON47934 pMON57934 is a binary vector in which the rice OsANT1 polypeptide coding sequence was tagged at the 3' end with the Flag epitope sequence and is driven by the e35S promoter for constitutive plant expression. The OsANT1 full-length cDNA was first cloned to a TA vector by RT-PCR, as described in Example 3. The resulting plasmid was then cut with EcoRI to release the OsANT1 coding sequence, followed by the purification of the OsANT1 gene by gel-electrophoresis. The binary vector pMON23450 was cut with EcoRI and then dephosphorylated by CIAP treatment (New England Biolabs, MA), followed by ligation to the prepared OsANT1 gene and propagation in *E. coli* using standard procedures as described above. The petunia HSP 70 leader used in this construct is described in U.S. Pat. No. 5,659,122.

EXAMPLE 19

Construction of pMON57988

PMON57988 is a binary vector for the constitutive expression of the *Arabidopsis* ANT gene in corn. The promoter is the rice actin promoter, P-ract1, from pMON25455. The construction of pMON57988 took two steps: the first step involved the synthesis of the ANT expression cassette in an intermediate vector, the second the construction of the binary expression vector. To construct the expression cassette, pMON57914, which contains the ANT gene and was described in Example 8, was first digested with SmaI and EcoRI, followed by Klenow treatment to blunt the sticky end generated by EcoRI. The resulting 2330 bp fragment, which included the entire ANT coding sequence and the E9 3' terminator, was gel purified. To construct the ANT expression cassette in an intermediate vector, pMON25455, which contains the R-act1 promoter, was digested with SmaI and NcoI, followed by Klenow treatment to blunt the end generated by NcoI. The resulting vector fragment, now having the GUS gene removed, was gel purified and ligated to the ANT-containing fragment prepared above, followed by propagation in *E. coli*. As the ANT insertion could take place in both orientations, plasmids with the correct orientation where P-ract1 was in front of ANT was determined by restriction mapping. The identified plasmid was named pMON57989. To put the ANT expression cassette in a binary vector, the cassette was released from pMON57989 by digesting with NotI, followed by gel purification; the binary portion of pMON36176 was also generated by digesting the plasmid with NotI, followed by dephosphorylation with CIAP and gel purification. The prepared ANT cassette and the pMON36176 vector were then ligated and propagated in *E. coli*. Plasmids were prepared from individual colonies for restriction analysis, and a clone with head to head (P-ract1/ANT vs. P-35S/Kan) configuration was selected as pMON57988. This plasmid contains lox sites which can be used to excise the selectable marker using the cre/lox system.

EXAMPLE 20

Construction of pMON57991 pMON57991 was a binary vector in which the *Arabidopsis* ANT gene was driven by the wheat POX1 (also termed pox1) promoter for root-enhanced expression in plants. Similarly as in Example 19, the construction took two steps: the first step involved the synthesis of the ANT expression cassette with the POX1 promoter in an intermediate vector, the second the mobilization of the cassette into a binary vector. To construct the expression cassette, a 2330 bp fragment including the entire ANT coding sequence and the E9 3' terminator was prepared from pMON57914, as described in Example 19. The promoter POX1 was obtained by digesting pMON36304 with SmaI and NdeI, followed sequentially by Klenow filled-in, CIAP (Calf intestinal alkaline phosphatase) dephosphorylation and gel purification. Ligation of the above prepared fragments generated plasmid pMON57996, upon discrimination from those with a wrong orientation as described in Example 19. The ANT expression cassette from this intermediate plasmid was then mobilized to the binary vector pMON36176 using the same procedure as described in Example 19, resulting in the construction of pMON57991.

EXAMPLE 21

The stored RNA is purified using Trizol reagent from Life Technologies (Gibco BRL, Life Technologies, Gaithersburg, Md. U.S.A.), essentially as recommended by the manufacturer. Poly A+RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

EXAMPLE 22

For RNA preparation, the stored cotton tissue is grounded thoroughly in liquid nitrogen and then incubated with a high SDS solution (about 2.5% SDS by weight, 0.1 M Tris-HCl (pH7.5), 2.5 M sodium perchlorate, 0.1% b-mercaptoethanol by volume) and insoluble PVPP (about 8.5% by weight) for about 30 minutes at the room temperature. Nucleic acids are then precipitated after filtration. The total RNA is isolated from the precipitate using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

EXAMPLE 23

This example illustrates how rice BAC library is constructed and how BAC contigs are obtained.

The rice BAC library may be constructed in the pBeloBAC11 or similar vector. BAC vector, pBeloBAC 11, is derived from the endogenous *E. coli* F-factor plasmid, which contains genes for strict copy number control and unidirectional origin of DNA replication. Additionally, pBeloBAC11 has three unique restriction enzyme sites (Hind III, Bam HI and Sph I) located within the LacZ gene which can be used as cloning sites for megabase-size plant DNA. Indigo, another BAC vector contains Hind III and Eco RI cloning sites. This vector also contains a random mutation in the LacZ gene that allows for darker blue colonies.

Megabase-size DNA of high quality with minimal breakage can be prepared using protoplast method. The protoplast method involves preparing young leaves which are manually feathered with a razor-blade before being incubated for four to five hours with cell-wall-degrading enzymes and then isolating protoplasts. Megabase-size DNA may also be prepared using the universal nuclei method developed by Zhange et al. (*Plant J.* 7:175–184 (1995), herein incorporated by reference in its entirety). In the universal nuclei method, fresh or frozen tissue is homogenized with a blender or mortar and pestle and then nuclei are isolated. Once protoplasts or nuclei are produced, they are embedded in an agarose matrix as plugs or microbeads. The agarose provides a support matrix to prevent shearing of the DNA while allowing enzymes and buffers to diffuse into the DNA. The DNA is purified and manipulated in the agarose and is stable for more than one year at 4° C.

Once high molecular weight DNA has been prepared, it is fragmented to the desired size range by partial restriction enzyme (e.g., Eco RI or other enzymes) digestion. The advantage of partial restriction enzyme digestion is that no further enzymatic modification of the ends of the restriction fragments are necessary. Four common techniques that can be used to achieve reproducible partial digestion of megabase-size DNA are 1) varying the concentration of the restriction enzyme, 2) varying the time of incubation with the restriction enzyme 3) varying the concentration of an enzyme cofactor (e.g., $Mg^{2+}$) and 4) varying the ratio of endonuclease to methylase.

After partial digestion of megabase-size DNA, the DNA is run on a pulsed-field gel, and DNA in a size range of 100–500 kb is excised from the gel. This DNA is ligated to the BAC vector or subjected to a second size selection on a pulsed field gel under different running conditions. Studies have previously reported that two rounds of size selection can eliminate small DNA fragments co-migrating with the selected range in the first pulse-field fractionation. Such a strategy results in an increase in insert sizes and a more uniform insert size distribution. A practical approach to performing size selections is to first test for the number of clones/microliter of ligation and insert size from the first size selected material. If the numbers are good (500 to 2000 white colony/microliter of ligation) and the size range is also good (50 to 300 kb) then a second size selection is practical. When performing a second size selection one expects a 80 to 95% decrease in the number of recombinant clones per transformation.

Twenty to two hundred nanograms of the size-selected DNA is ligated to dephosphorylated BAC vector (molar ratio of 10 to 1 in BAC vector excess). Most BAC libraries use a molar ratio of 5 to 15:1 (size selected DNA:BAC vector).

Transformation is carried out by electroporation and the transformation efficiency for BACs is about 40 to 1,500 transformants from one microliter of ligation product or 20 to 1000 transformants/ng DNA.

The quality of a BAC library can be assessed by determining the genome coverage of a BAC library-average insert size, average number of clones hybridizing with single copy probes, and chloroplast DNA content.

The determination of the average insert size of the library is assessed in two ways. First, during library construction every ligation is tested to determine the average insert size by assaying 20–50 BAC clones per ligation. DNA is isolated from recombinant clones using a standard mini preparation protocol, digested with Not I to free the insert from the BAC vector and then sized using pulsed field gel electrophoresis (Maule, *Molecular Biotechnology* 9:107–126 (1998), herein incorporated by reference in its entirety).

To determine the genome coverage of the library, it is screened with single copy RFLP markers distributed randomly across the genome by hybridization. Microtiter plates containing BAC clones are spotted onto Hybond membranes. Bacteria from 48 or 72 plates are spotted twice onto one membrane resulting in 18,000 to 27,648 unique clones on each membrane in either a 4×4 or 5×5 orientation. Since each clone is present twice, false positives are easily eliminated and true positives are easily recognized and identified.

Finally, the chloroplast DNA content in the BAC library is estimated by hybridizing three chloroplast genes spaced evenly across the chloroplast genome to the library on high density hybridization filters.

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, New York (1999), the entirety of which is herein incorporated by reference).

PHRED is used to call the bases from the sequence trace files. Phred was developed at the Univerity of Washington and can be found by going to the university website, and searching for "phred". Quoting from their website, "Phred reads DNA sequencer trace data, calls bases, assigns quality values to the bases, and writes the base calls and quality values to output files. Phred can read trace data from SCF files and ABI model 373 and 377 sequencer chromat files, automatically detecting the file format. After calling bases, phred writes the sequences to files in either FASTA format, the format suitable for XBAP, PHD format, or the SCF format. Quality values for the bases are written to FASTA format files or PHD files, which can be used by the phrap sequence assembly program in order to increase the accuracy of the assembled sequence.". Phred uses Fourier methods to examine the four base traces in the region surrounding each point in the data set in order to predict a series of evenly spaced predicted locations. That is, it determines where the peaks would be centered if there were no compressions, dropouts, or other factors shifting the peaks from their "true" locations. Next, PHRED examines each trace to find the centers of the actual, or observed peaks and the areas of these peaks relative to their neighbors. The peaks are detected independently along each of the four traces so many peaks overlap. A dynamic programming algorithm is used to match the observed peaks detected in the second step with the predicted peak locations found in the first step.

After the base calling is completed, contaminating sequences (*E. coli*, BAC vector sequences >50 bases and sub-cloning vector are removed and constraints are made for the assembler. Contigs are assembled using CAP3 (Huang, et al., *Genomics* 46: 37–45 (1997) the entirety of which is herein incorporated by reference).

EXAMPLE 24

This example illustrates how *Agrobacterium* cells are transformed and how transformed cells are cultured.

Transformation
1. Electroporate 2 µl of DNA construct into 20 µl of ABI competent cells;
2. Pipette transformed cells directly onto LB plates containing Spectinomycin (75 µg/ml), Kanamycin (50 µg/ml), Chloramphenicol (25 µg/ml). Add 50 µl of SOC media to plate and spread;
3. Incubate plated transformation at 28° C. for 2 days (or can grow over weekend).

ABI Cell Culture:
1. Pick 3 colonies per ABI plate and grow each in 4 ml LB media containing Spectinomycin (75 µg/ml), Kanamycin (50 µg/ml), Chloramphenicol (25 µg/ml);
2. Incubate 4 ml cultures of at 28° C., shaking, for 2 days. (culture tubes should be at an angle).

Glycerol Stocks, & DNA Preps:
1. Make three 1 ml ABI glycerol stocks per 4 ml culture, using 500 µl of culture and 500 µl of 40% glycerol. Freeze and store at −80° C.
2. Miniprep remaining culture (about 2.5 ml), using a Qiagen miniprep kit and protocol (Qiagen Genomics, Inc., Seattle, Wash.), ensuring add PB buffer wash step and EB buffer (10 mM Tris-Cl, pH 8.5) to 70° C. before eluting DNA from column. The resulting volume per miniprep sample should be 50 µl.

Digest Confirmation
1. Using the Pollux and construct maps,determine whether the plasmids transformed into the bacteria are, in fact, the plasmids transformed. Restriction enzymes are selected that allow this by finding appropriate enzymes that cut in both the insert and the plasmid and allow the discrimination of this specific plasmid from some or all others.
2. Digest 17 µl miniprep DNA per digest, resulting in a final digest volume of 20 µl;
3. Run 20 µl of each digest on 1% agarose gel vs. 1 Kb DNA ladder; and
4. For 2 of 3 confirmed clones, streak LB plates containing Spectinomycin (75 µg/ml), Kanamycin (50 µg/ml), Chloramphenicol (25 µg/ml) from ABI glycerol stocks and allow to grow at 28° C. for 2 days (or can grow over weekend).

Sequencing for Insert Verification (as an Alternative to, or in Addition to, Digest Confirmation):
1. In addition to the above digest confirmation, it would be possible to confirm the insert integrity and type by DNA sequencing.
2. A DNA primer would be selected 50–500 base pairs from the junction between the plasmid (backbone) DNA and the insert DNA. Said primer's 3' end would face toward the insert.
3. An appropriate DNA sequencing reaction and read on a polyacrylamide gel or other column could be used to determine the sequence of the DNA.
4. One would specifically look for the DNA sequence at the junction to determine whether said sequence was appropriate and determine whether sequence of said insert was as the researcher expected.

EXAMPLE 25

*Arabidopsis* plants may be transformed by any one of many available methods. For example, *Arabidopsis* plants may be transformed using In planta transformation method by vacuum infiltration (see, Bechtold et al., *In planta Agrobacterium* mediated gene transfer by infiltration of adult *Arabidopsis thaliana* plants. CR Acad. Sci. Paris Sciences de la vie/life sciences 316: 1194–1199 (1993), herein incorporated by reference in its entirety). This example illustrates how *Arabidopsis* plants are transformed.

Stock Plant Material and Growth Conditions
Prepare 2.5 inch pots with soil and cover them with a mesh screen, making sure that the soil is not packed too tightly and the mesh is in contact with the soil surface (this ensures that the germinating seedlings will be able to grow through the mesh). Sow seeds and cover with a germination dome. Vernalize seeds for 3–4 days. Grow plants under conditions of 16 hours light/8 hours dark at 20–22° C., 70% humidity. Water twice weekly, and fertilize from below with ½×(half of the strength recommended by the manufacturer) Peters 20-20-20 fertilizer (from Hummert International, Earth City, Mo.). Add micronutrients (Hummert's Dynagrain Soluble Trace Elements) (in full strength recommended by the manufacturer) every other week. After about 1–2 weeks, remove the dome and thin the pots to one or two plants per pot. Clip the primary bolt, when it develops, to encourage more secondary bolt formation. In 5–7 days the plants will be ready for infiltration.

Agrobacterium Preparation (Small Scale and Large Scale Cultures):

Agrobacterium strain ABI is streaked onto an LB plate containing Spectinomycin 100 mg/L, Streptomycin 100 mg/L, Chloramphenicol 25 mg/L, and Kanamycin 50 mg/L (denoted SSCK). Two days prior to infiltration, a loop of Agrobacterium is placed into a tube containing 10 mls LB/SSCK and put on a shaker in the dark at 28° C. to grow overnight. The following day, the Agrobacterium is diluted 1:50 in 400 mls YEP/SSCK and put on a shaker at 28° C. to grow for 16–20 hours. (Note: we have found the transformation rate is significantly better when LB is used for the first overnight growth and YEP is used for the large scale overnight culture).

Infiltration

Harvest the Agrobacterium cells by pouring into a 500 ml centrifuge bottle and spinning at 3500 rpm for 20–25 minutes. Pour off the supernatant. Dry the pellet and then resuspend in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (BAP) (10 µl of a 1.0 mg/L stock in DMSO per liter) and 0.02% Vac-in-Stuff (Silwet L-77) from Lehle Seeds (Round Rock, Tx.). The BAP and Silwet L-77 are added fresh the day of infiltration. Add 200 µl of Silwet L-77, and 20 µl of BAP (0.5 mg/L stock). Using Infiltration Medium as your blank, take the $OD_{600}$ of a 1:10 dilution of the Agrobacterium suspensions. Calculate the volume needed for 400 ml of Agrobacterium suspension/infiltration medium, OD600=0.6, for the vacuum infiltration.

Equation: (final volume)*(final OD600)=Volume needed for final OD600 of 0.6OD600

Place resuspended culture in a Rubbermaid container inside a vacuum dessicator. Invert pots containing plants to be infiltrated into the solution so that the entire plant is covered, including the rosette, but not too much of the soil is submerged. Soak the plants with water for at least 30 min. prior to infiltration. (This keeps the soil from soaking up the Agrobacterium suspension).

Draw a vacuum of ~23–27 in. Hg for 10 min. Quickly release the vacuum. Briefly drain the pots, place them on their sides in a diaper-lined tray, cover the tray with a dome to maintain humidity, and return to growth chamber. The following day, uncover the pots, set them upright, and remove the diaper. Do not water plants for ~5 days. After the 5 days are up, allow the plants to be watered and to continue to grow under the same conditions as before. (The leaves that were infiltrated may degenerate but the plant should survive until it is finished flowering).

Harvesting and Sterilizing Seed

Cone the plants, individually, by using the Lehle Aracons (Lehle Seeds, Round Rock, Tex.) approximately 2 weeks after infiltration. After all of the seed is matured and has set (~4 weeks post-infiltration), remove the plants from water to dry down the seeds. Approximately 2 weeks later harvest the seeds by cutting the branches below the cone. Clean the seed by using a sieve to catch the silique and branch material and allow the seed to go through. Place the seed in an envelope or in 15 ml conical tubes.

Transfer desired amount of seeds to 15 ml conical tubes prior to sterilization. Loosen the lid to the conicals and place them on their side in a vacuum dessicator with a beaker containing 400 ml of bleach Clorox (Clorox Company, Oakland, Calif.) and 4 ml of Hydrochloric Acid. (Add the HCl to the Clorox in a fume hood). Pull a vacuum just to seal the dessicator, and close the suction (i.e. so that the dessicator is still under a vacuum but the vacuum is not still being directly pulled) for ~16 hrs. After sterilization, release the vacuum and place tubes containing seed in a sterile hood (keep caps loose so gas can still be released).

Plate ("sprinkle") the seed on selection plates containing MS Basal Salts 4.3 g/L, Gamborg' a B-5 (500×) 2.0 g/L, Sucrose 10 g/L, MES 0.5 g/L, and 8 g/L Phytagar (Life Technologies, Inc., Rockville, Md.) with Carbenicillin 250 mg/L, Cefotaxime 100 mg/L. Selection levels will either be kanamycin 60 mg/L, Glyphosate 60 µM, or Bialaphos 10 mg/L.

A very small amount of seed can be first plated out to check for contamination. If there is contamination, re-sterilized seeds for ~4 more hours and check for contamination again. The second sterilization is usually not necessary, but sometimes the seed harbors a fungal contaminant and repeat sterilizations are needed. (The sterilization duration generally is shorter than 16 hours because of significantly decreased germination rates starting at 24 hr. sterilization duration). Seal plates with parafilm and place in a cold room to vernalize for ~2–4 days. After seeds are vernalized, place in percival with cool white bulbs.

Transfer to Soil

After 5–10 days at ~26° C. and a 16/8 light cycle, the transformants will be visible as green plants. After another 1–2 weeks, plants will have at least one set of true leaves. Transfer plants to soil, cover with a germination dome, and move to a growth chamber with normal Arabidopsis growth conditions. Keep covered until new growth is apparent (usually 5–7 days).

EXAMPLE 26

This example illustrates how the shoot biomass of Arabidopsis plants can be increased by ectopically expressing the crop ANT-like genes in transgenic Arabidopsis plants.

The soybean ANT-like genes, GmANT1 and GmANT2, which were identified and cloned according to the procedure described in Example 1, were constructed into a binary vector for stransgenic expression under the control of the CaMV e35S promoter, as described in Examples 9 and 10, respectively. The rice ANT-like gene, OsANT1, which was identified and cloned according to the procedure described in Example 2, was constructed into a binary vector for transgenic expression under the control of the CaMV e35S promoter, as decribed in Example 18. The Arabidopsis ANT gene was cloned and constructed into a binary vector for the Agrobacterium-mediated transformation and constitutive expression of ANT in Arabidopsis plants under the control of the CaMV e35S promoter, as described in Examples 7 and 8. Agrobacterium transformation with the above constructed vectors were carried out according to the protocol described in Example 24. Arabidopsis transformation and subsequent generation of transgenic plants were performed as described in Example 25.

T1 seeds of the transgenic plants were sowed in potted soil along with wild-type plants (controls), and were vernalized for three days before moving to a growth chamber. The plants were grown under the following conditions: at 22° C., 24 hours constant light with light intensity of 170–200 µm Einstein $m^{-2}s^{-1}$, and a humidity of 70%. Plants were also grown under short day conditions, with 10 hours of light period. Plants were fertilized twice a week using Peters 20-20-20 fertilizer (in half strength) from Hummert International, Earth City, Mo.). Plants were monitored for both vegetative and reproductive growth. Under both long day and short day conditions, the transgenic plants expressing the *Arabidopsis* ANT had similar above ground vegetative vigor as the wild-type control plants. However, the transgenic plants expressing the crop ANT-like genes had more vigorous shoot growth. For example, under short day growth conditions, the leaf area of transgenic plants expressing the rice OsANT1 was increased by 40% at day 42.

EXAMPLE 27

This example illustrates that the ectopic expression of *Arabidopsis* ANT and the crop ANT-like genes in *Arabidopsis* transgenic plants resulted in increase in the growth and biomass of roots.

Previous studies have suggested that the ectopic expression of the *Arabidopsis* ANT had no effect on root development of transgenic plants (Krizek, Developmental Genetics 25: 224–236 (1999); Y Mizukami and R L Fischer, Proc. Natl. Acad. Sci. 97: 942–947 (2000); both of which are herein incorporated by reference in their entirety). The data included herein suggests that the ectopic expression of the *Arabidopsis* ANT as well as other crop ANT-like genes can cause increase in root growth.

Transgenic plants expressing the *Arabidopsis* ANT and those expressing the rice OsANT1, both driven by the e35S promoter, were produced as described in Example 26. In addition, transgenic plants expressing the ANT driven by the root-specific promoter, Rb7, were also produced as described in Examples 16, 24 and 25. The seeds were harvested for further planting and transgenic analysis. To prepare the plates for germination, 3.54 gram of the MS plant tissue culture medium (Sigma, St Louis, Mo.) and 0.5 gram sucrose was dissolved in one liter of deionized water, pH adjusted to 5.8 with KOH, 8 gram Phytagar (GIBCO) added before autoclaving for 21 min, followed by distributing to 9×9 cm square petri dish plates, with 35 ml per plate. To sow the seeds onto the plate, seeds were sterilized in 70% ethanol for 2 min and then in 30% commercial bleach, 0.01% Triton X-100 for 3 minutes, followed by 4 washes in sterile water. The sterilized seeds were laid onto the plate, which were vernalized at 4° C. for 3 days before moving to the growth chamber as described in Example 26. The plates were set up in vertical position, and the root and shoot growth rate were monitored daily upon germination. Comparison of the transgenic seedlings with the wild-type demonstrates that the roots of transgenic plants were longer and bigger, and the leaves apparently more green. For example, at the fourth day after germination, the roots of the transgenic lines were about 20–40% longer than the wild-type control on the same plate.

TABLE 5

Root length of transgenic and normal plants.

| root length at day 4: | mm | % increase |
|---|---|---|
| WT | 13.8 +/− 0.17 | 0 |
| OsANT1 | 19.3 +/− 0.88 | 40 |

EXAMPLE 28

This example illustrates that the ectopic expression of ANT and ANT-like genes in transgenic *Arabidopsis* plants can result in increased floral organ size.

Transgenic plants expressing the *Arabidopsis* ANT, as well as those expressing the soy GmANT1 and GmANT2, all driven by the CaMV e35S promoter, were produced according to the procedures as described in Example 26. In addition, transgenic plants expressing ANT driven by the SSU1A promoter were also produced as described in Examples 14, 24 and 25. The seeds were harvested for line advancement and further transgenic analysis. The floral organ size was measured and compared to that of wild-type plants. The results showed that transgenic plants had larger floral organs than wild-type plants. For example, the petal size of transgenic plants expressing the soy GmANT1 driven by the CaMV e35S promoter was increased by up to 100% compared to that of wild-type plants, while the petal size of transgenic plants expressing ANT driven by the SSU1A promoter was increased by 75%.

Increased floral organ size can be useful in the flower industry, to produce larger flowers in roses and other commercially important flowers. Increased floral organ size can also be important as larger flowers in some plants lead to larger seeds and/or fruits.

TABLE 6

Petal size in transgenic and normal plants.

| | Petal size (U) | % increases |
|---|---|---|
| WT | 13328 +/− 730 | 0 |
| GmANT1 | 27429 +/− 889 | 106 |

EXAMPLE 29

This example illustrates that the conditional expression of ANT and the ectopic expression of the crop ANT-like genes can result in increased seed size.

Transgenic plants expressing ANT under the control of the e35S promoter and the SSU1A promoter were produced as described in Example 28; transgenic plants expressing the soy GmANT1 and GmANT2 were produced as described in Example 28; transgenic plants expressing the rice OsANT1 were produced as described in Example 26. In all cases, transgenic plants with seeds larger than the wild-type were obtained. Furthermore, the big seed phenotype was transmitted to the next generation, at least for the transgenic plants expressing ANT from the SSU1A promoter that we have tested. For example, the size of V3 seeds of transgenic plants expressing ANT from SSULA were increased by 27%.

Increased seed size leads to greater yield in many economically important crop plants. Increased seed size is thus one goal of genetically engineering and selection.

TABLE 7

Seed size in transgenic and normal plants.

| Transgene | Promoter | Line | Generation | % increase |
|---|---|---|---|---|
| WT | | | | 0 |
| ANT | 35S | 7884-3 | V3 | 18 |
| ANT | 35S | 7884-7 | V3 | 16 |
| ANT | SSU1A | 1H1 | V2 | 19 |
| ANT | SSU1A | 2A1 | V2 | 27 |
| OsANT1 | 35S | 10582 | V2 | 32 |
| OsANT1 | 35S | 10593 | V2 | 26 |

EXAMPLE 30

This example illustrates that the conditional expression of ANT and the crop ANT-like genes can increase the seed oil content.

Transgenic plants expressing the ANT from the seed-specific Napin promoter were produced as described in Examples 13, 24 and 25. Biochemical analysis of the seeds from the transgenic plants showed that the seed oil content was increased compared to the wild-type control. For example, the oil content of V3 seeds tested was increased by 16% when compared to the wild-type control.

Increased oil content is also a measure of yield in many economically important plants. Soybean, corn, canola and other plant oils are economically important thus increasing amount of oil per seed is advantageous.

TABLE 8

Percentage of oil in seed of transgenic and normal plants.

| | % Oil |
|---|---|
| WT | 27.8 +/− 0.83 |
| ANT/Napin_1A2 | 30.4 +/− 0.68 |
| ANT/Napin_1A3 | 32.1 +/− 0.6 |
| ANT/Napin_1D8 | 31.7 +/− 1.18 |

EXAMPLE 31

This example illustrates that the conditional expression of ANT and the crop ANT-like genes can increase the seed yield.

Transgenic plants expressing the ANT gene from the seed-specific Napin promoter were produced as described in Examples 13, 24 and 25. Transgenic plants were grown in controlled conditions along with wild-type plants, as described in Example 26. Seeds were harvested from individual plants at maturity. Analysis shows that the seed weight per plant was increased compared to the wild-type control. For example, the seed weight of the 1A2_V4 line was increased by 35% when compared to the wild-type control.

Weight of seeds is an important characteristic of seed in crop plants, as plants that produce more seed are more desirable that those that those that produce less seed.

TABLE 9

Seed yield increase by transgene ANT driven by the Napin promoter

| Line | Seed weight (mg)/plant | % increase |
|---|---|---|
| WT | 170.4 +/− 12.5 | 0 |
| 1A2_V4 | 230.8 +/− 20.5 | 35 |
| 1A3_V4 | 225 +/− 12.5 | 32 |
| 1D8_V4 | 188.1 +/− 24.5 | 10 |

EXAMPLE 32

In order to determine how the expression of ANT genes can affect characteristics of corn, corn was transformed with the ANT gene containing constructs driven by the rice actin and pox-1 promoters. The construct containing the rice actin promoter was rACT1-ANT is pMON57988 (see Example 19). The construct containing pox1-ANT was pMON57991 (see Example 20). Transgenic corn plants were produced by an *Agrobacterium* mediated transformation method. Disarmed *Agrobacterium* strain C58 (ABI) harboring vectors of the present invention was used for all the experiments. The DNA construct is transferred into *Agrobacterium* by a tri-parental mating method (Ditta et al., Proc. Natl. Acad. Sci. 77:7347–7351).

*Agrobacterium* ABI in glycerol stock is streaked out on solid LB medium supplemented with the antibiotics kanamycin (50 mg/L), spectinomycin (100 mg/L), streptomycin (100 mg/L) and chloramphenicol (25 mg/L) and incubated at 28 ° C. for 2 days. Two days before *Agrobacterium* inoculation, one colony from the *Agrobacterium* plate is picked up and inoculated into 25 mL of liquid LB medium supplemented with 100 mg/L each of spectinomycin and kanamycin in a 250-mL flask. The flask is placed on a shaker at approximately 150 rpm and 27° C. overnight. The *Agrobacterium* culture is then diluted (1 to 5) in the same liquid medium and put back to the shaker. Several hours later in the late afternoon one day before inoculation, the *Agrobacterium* cells are spun down at 3500 rpm for 15 min. The bacterium cell pellet is re-suspended in induction broth with 200 µM of acetosyringone and 50 mg/L spectinomycin and 25 mg/L kanamycin and the cell density is adjusted to 0.2 at O.D.$_{660}$. The bacterium cell culture (50 mL in each 250-mL flask) is then put back to the shaker and grown overnight. In the morning of inoculation day, the bacterium cells are spun down and washed with liquid ½MS VI medium (Table 1) supplemented with 200 µM of acetosyringone. After one more spinning, the bacterium cell pellet is re-suspended in ½MS PL medium (Table 1) with 200 µM of acetosyringone (Table 1), and the cell density is adjusted to 1.0 at O.D$_{660}$ for inoculation. After resuspension, the *Agrobacterium* can be stored at 4□C. for up to 27 days and used as desired.

Reagents are commercially available and can be purchased from a number of suppliers (see, for example Sigma Chemical Co., St. Louis, Mo.).

TABLE 10

| Component | ½ MS VI | ½ MS PL | Co-culture medium | LH172 MS | MS/BAP | MSOD |
|---|---|---|---|---|---|---|
| MS salts | 2.2 g/l | 2.2 g/l | 2.2 g/l | 4.4 g/l | 4.4 g/l | 4.4 g/l |
| Sucrose | 20 g/l | 68.5 g/l | 20 g/l | 30 g/l | 30 g/l | — |
| Maltose | — | — | — | — | — | 40 g/l |
| Glucose | 10 g/l | 36 g/l | 10 g/l | — | — | 20 g/l |
| 1-Proline | 0.115 g/l | 0.115 g/l | 0.115 g/l | 1.36 g/l | 1.36 g/l | — |
| Casamino Acids | — | — | — | 0.05 g/l | 0.05 g/l | — |
| Glycine | 2 mg/l | 2 mg/l | 2 mg/l | — | — | — |
| 1-Asparagine | — | — | — | — | — | 150 mg/l |
| myo-Inositol | 100 mg/l | 100 mg/l | 100 mg/l | — | — | 100 mg/l |
| Nicotinic Acid | 0.5 mg/l | 0.5 mg/l | 0.5 mg/l | 0.65 mg/l | 0.65 mg/l | 0.65 mg/l |
| Pyridoxine·HCl | 0.5 mg/l | 0.5 mg/l | 0.5 mg/l | 0.125 mg/l | 0.125 mg/l | 0.125 mg/l |
| Thiamine·HCl | 0.1 mg/l | 0.1 mg/l | 0.6 mg/l | 0.125 mg/l | 0.125 mg/l | 0.125 mg/l |
| Ca Pantothenate | — | — | — | 0.125 mg/l | 0.125 mg/l | 0.125 mg/l |
| 2,4-D | — | — | 3 mg/l | 0.5 mg/l | 0.5 mg/l | — |
| Picloram | — | — | — | 2.2 mg/l | 2.2 mg/l | — |
| Silver Nitrate | — | — | — | 3.4 mg/l | — | — |
| Na-Thiosulfate | — | — | — | — | — | — |
| Phytagar | — | — | — | 7.0 g/l | 7.0 g/l | 7.0 g/l |
| Low EEO agarose | — | — | 5.5 g/l | — | — | — |

Immature embryos (1.5–2.0 mm) from LH172 are isolated from sterilized ears and dipped into *Agrobacterium* cell suspension in 1.5-ml microcentrifuge tubes continuously for 15 minutes. The tube is then set aside for 5 min. After the *Agrobacterium* suspension is removed using a transfer pipet with fine tip, the embryos are transferred to standard co-culture medium (Table 1). The embryos are placed with the scutellum side facing up. The embryos are cultured in a Percival incubator set at 23° C. and dark for approximately 24 h.

Selection and Regeneration and Growth

After the co-cultivation, the embryos are transferred from the co-culture plates onto callus induction medium, LH172 MS (Table 1) with 500 mg/L carbenicillin and 100 or 200 mg/L paromomycin. The plates are kept in a dark culture room at 27° C. for approximately 2 weeks. Two weeks later, almost all the callus pieces developed individually are transferred onto MS6BAP (Table 1) with 250 mg/L carbenicillin and 100 or 200 mg/L paromomycin. The plates are kept in a culture room with 16-h light and at 27° C. for 5–7 days. Then, the callus pieces are transferred onto MSOD (Table 1) with 250 mg/L carbenicillin and 100 or 200 mg/L paromomycin. In another 2 weeks, all the pieces with shoots or living tissue are transferred onto the same media in phytatrays for further growth.

When the plantlets reach the lid and have a few roots, they are moved to soil in peat pots in a growth chamber. In 7 to 10 days, they are transplanted into 12-in pots and moved to the greenhouse with conditions for normal corn plant growth.

EXAMPLE 33

The expression of an exogenous *Arabidopsis* ANT gene in corn plants.

For expression of ANT in corn, two promoters were used. One was the largely constitutive rice actin promoter (U.S. Pat. No. 5,641,876), and the other the root-enhanced pox1 promoter (Hertig, et al., Plant Molecular Biology 16:171). Both constructs included the 3' termination sequence from the E9 gene.

The construct containing rACT1-ANT is pMON57988 (see Example 19). The construct containing pox1-ANT is pMON57991 (see Example 20). DNA of each plasmid was introduced into an *Agrobacterium* strain (ABI) by electroporation. Plants containing rACTI-ANT (pMON57988) were named Abby, and plants with the pox1-ANT construct were named Anny (pMON57991).

Expression of the ANT gene in leaves of RO plants (V6-V8 stage) was analyzed using Taqman to determine levels of MRNA. Taqman is a real time sequence detection system supplied by Applied Biosystems. Taqman allows the real time quantitative determination of levels of PCR product present. In this specific case we used primers to detect the E9 termination region in order to determine expression levels. The specific primers used were:

forward primer=CAACGTTCGTCAAGTTCAATGC (SEQ ID NO: 20)

reverse primer=TGCCATAATACTCGAACTCAGTAGGA (SEQ ID NO: 21)

probe=6FAM-TCAGTTTCATTGCGCACACACCA-GAA-TAMRA. (SEQ ID NO: 22)

The FAM and TAMRA are fluorescent based dyes. The FAM is the reporter dye and the TAMRA is the quencher. Further details of the Taqman assay are available from the manufacturer (Applied Biosystems, Foster City, Calif.).

Expression levels in transgenic plants were compared to those in a wild type control. The average relative expression compared to wild type for Abby events selected for further study ranged from 1558 to 42,027, and for Anny ranged from 739 to 6002. The lower expression in Anny was expected as in these events the ANT gene is driven by the root-enhanced promoter (and leaf tissue was analyzed). For Abby, 26 transgenic lines were selected from 37 lines. For Anny, 19 transgenic were selected from 33 R0 lines. The RO plants were selfed to generated R1 seed, and also crossed to a wild type LH172 (a specific inbred line of corn available from Holden) to generate F1 seed.

R1 seed of these events was planted in a field near Jerseryville, Ill. in May 2001. However, the plants were lost in a windstorm Therefore, seed was planted in a field the Kihei, HI in August 2001 for observation and advancement to the next generation. Seed availability reduced the number of events planted to 19 for Abby, and 11 for Anny. The seed used was from a cross wherein the transgene was segregating to some offspring, but not all, thus 24 plants per row were labeled, and leaf tissue was harvested, DNA produced, and PCR was done to determine presence or absence of the gene by PCR of the E9 3' end (in a manner similar to the Taqman protocol above, using the same primers).

Height of plants at the time of silking was measured (distance from soil to the collar of the flag leaf) (see example 34).

Further observations are planned. Seed and ear specific traits include row number, 100-kernel weight (kernels taken from the middle of the cob), and cob length. All measurements will be correlated with presence or absence of the ANT gene. Events that demonstrate a 1:1 segregation of the transgene will be advanced to the next generation.

The next steps for these events are to determine effects of the ANT gene on plant growth and development. For the pox1-ANT events, F1 seed will be germinated in the dark on rolled blotter paper at 25° C. for 5 to 7 days. Root length will be measured, and samples will be taken for PCR analysis of the transgene. We expect that plants that express the *Arabidopsis* ANT under a root specific promoter will have longer roots.

For the constitutive rACT1 promoter, we plan to generate homozygous lines before conducting further phenotype analysis. PCR-positive F2 ears (2 per event) will be selected for advancement, and seed will be planted in Hawaii in December 2001. DNA Taqman (Applied Biosystems, Foster City, Calif.) will be used to determine zygosity of plants in the row (24 plants per event). All plants will be selfed. Homozygous positive and homozygous negative lines will be selected for further study.

The constitutive promoter will be used to determine the effect of ANT on size of vegetative and reproductive organs. Production of larger seeds may increase yield. Alternatively, production of larger leaves may increase yield by providing more source capacity, and stimulation of root growth could provide more mineral nutrients or water to increase kernel production. The root-enhanced promoter was used to determine whether the ANT gene can promote production of bigger roots that would enable the plant to more readily obtain mineral nutrients and water. When homozygous lines are available, 12 plants per selection will be planted in a greenhouse, and the following measures will be taken:

Height will be measured each week until tasseling (see example 34 and 26).
Length of selected leaves will be measured (see example 26).
Flowering time will be recorded (see example 28).
Female and male reproductive structures of plants will be examined (see example 28). Comparisons will be made between plants that contain the said transgene(s) and the negative isolines.
Root length of these selections will be measured by growing plants on the rolled blotter paper, as described for the pox1-ANT plants (see example 27 of RB7-ANT plants).

We expect all of the above traits could be affected in a positive, yield enhancing direction by the expression of the ANT gene(s), as were the *Arabidopsis* plants in prior examples.

EXAMPLE 34

Aintegumenta Expression in Corn.

Names of specific transgenic lines may be defined elsewhere (i.e. Abby and Anny are defined in Example 33.).

F1 corn plants containing ANT constructs were analyzed for final plant height, and seed return. It was not possible to measure other kernel and ear traits because of the highly variable rate of seed set on all the inbred ears from the nursery. No effect of the ANT gene on final plant height was observed (data not shown). However, an effect on fertility was seen with constitutive expression of ANT (Abby). Plants that contained the constitutive ANT construct did not produce seed as frequently as negative segregants. As a result, the proportion of plants with this construct (Abby) that contained the transgene was reduced in the population that produced seed, compared to the original plants in the row (Table 11). In contrast, the proportion of plants with the transgene was the same in these two populations for plants transformed with other constructs, including root-enhanced expression of ANT (Anny), and constructs containing other transegenes.

These data suggest that expression of the ANT gene in reproductive organs has a negative effect on fertility. This result is consistent with the report that most *Arabidopsis* plants with a 35S::ANT transgene were sterile (Mizukami and Fischer, 2000), and suggests that the *Arabidopsis* ANT gene is having a similar effect in corn as in *Arabidopsis*. This gene may be useful to enhance sink potential in corn, using promoters that target dividing endosperm cells, but that avoid expression in certain reproductive tissues. The Anny plants will be useful to determine the effect of ANT on root growth in corn. An example of root growth in *Arabidopsis* is seen in Example 27.

TABLE 11

Proportion of plants that contained the transgene is reduced in Abby population which produced seed, compared to all Abby plants in the row. Abby, ract1-ANT; Anny, pox1-ANT.

| | ratio: % PCR-POS plants with seed/ % PCR-POS plants in row | standard error |
|---|---|---|
| Abby | 0.62 | 0.09 |
| Anny | 1.04 | 0.07 |

EXAMPLE 35

In addition to the methods mentioned above and below, recombinant DNA constructs designed for the expression of ANT could be transformed into corn or other crops. A number of methods that would allow this exist. A DNA construct is transformed into a target crop of interest via an appropriate delivery system such as an *Agrobacterium*-mediated transformation method (see for example U.S. Pat. No. 5,569,834 herein incorporated by reference in its entirety, U.S. Pat. No. 5,416,011 herein incorporated by reference in its entirety, U.S. Pat. No. 5,631,152 herein incorporated by reference in its entirety, U.S. Pat. No. 5,159,135 herein incorporated by reference in its entirety, U.S. Pat. No. 5,004,863 herein incorporated by reference in its entirety, and U. S. Provisional Appln. No. 60/111795 herein incorporated by reference in its entirety. Alternatively, a particle bombardment method may be used (see for example Patent Applns. WO 92/15675. WO 97/48814 and European Patent Appln. 586,355, and U.S. Pat. Nos. 5,120,657, 5,503,998, 5,830,728 and 5,015,580, all of which are herein incorporated by reference in their entirety).

A large number of transformation and regeneration systems and methods are available and well-known to those of skill in the art. The stably transformed plants and progeny are subsequently analyzed for expression of the gene in tissues of interest by any number of molecular, immunodiagnostic, biochemical, and/or field evaluation methods known to those of skill in the art, including, but not limited to looking at any of a large number of phenotypic and physiologic traits (as in above examples; also transcriptional profiling; metabolic profiling, and others) in transformed plants and comparing them to plants transformed with different genes or non-transformed plants.

For example, a rice (or other monocot) ANT gene under a plant promoter could be transformed into corn, or another crop plant, to look at effects of monocot ANT genes in other monocots, or dicot ANT gene in other dicots, or monocot genes in dicots, or vice versa. The plasmids containing these ANT coding sequences, 5' of a promoter and 3' of a terminator would be constructed in a manner similar to those described for construction of other plasmids herein. Any number of promoters might be looked at, from tissue specific promoters, to constitutive promoters, to tissue-enhanced promoters, to myriad others within or without one of these groups.

EXAMPLE 36

Construction of pMON71250.

pMON71250 (FIG. 19) is a bombardment construct with the rice ANT1 (OsANT1) gene under the control of the Zea mays L3 (oleosin) promoter (Lee WS. et al., Proceedings of the National Academy of Science (USA) 88:6181, 1991; Lee K. et al., Plant Molecular Biology, 26:1981, 1994; Qu et al., Plant Science 72:223, 1990) for tissue-specific expression in corn germ and aleurone. The OsANT1 gene was PCR amplified using primers OsANTF (GGCGCGCCACAATG-GCCAGCGGCGGCGGCAG SEQ ID NO: 32) and OsANTR (CCTGCAGGTCAGGCATCTGTCCAGGCTG-CAA SEQ ID NO: 33) that contain AscI and Sse8387I, respectively. The PCR amplification included an initial denaturation step of 94° C. for 2 min followed by 30 cycles at 94° C. for 30 sec, 58° C. for 15 sec, 72° C. for 1 min. The PCR product was cloned, sequencing confirmed, and subcloned into the AscI and Sse83871 sites of L3 expression vector pMON71050 (see attached Pollux map). The resulting construct pMON71250 was confirmed by restriction mapping and junction sequencing. The MluI fragment containing the OsANT1 cassette was purified for corn transformation via bombardment into the LH59 corn line.

EXAMPLE 37

Methods of Microprojectile Bombardment

Approximately four hours prior to microprojectile bombardment, LH59 immature embryos were transferred to medium 211SV (N6 salts with 12% sucrose at pH 5.8, 1 mg 2,4-D, 17 mg AgNO$_3$, 1 mg thiamine HCl, 690 mg proline, 900 mg asparagine, 100 mg casamino acids, 500 mg MES). Twenty-five immature embryos were preferably placed in a 60×15 mm petri dish, arranged in a 5×5 grid with the coleoptilar end of the scutellum pressed slightly into the culture medium at a 20 degree angle. Tissue was maintained in the dark prior to bombardment.

Prior to microprojectile bombardment, a suspension of gold particles was prepared onto which the desired DNA was precipitated. Ten milligrams of 0.6 μm gold particles (BioRad) were suspended in 50 μL buffer (150 mM NaCl, 10 mM Tris-HCl, pH 8.0). Twenty five μL of a 2.4 nM solution of the desired DNA was added to the suspension of gold particles and gently vortexed for about five seconds. Seventy five μL of 0.1M spermidine was added and the solution vortexed gently for about 5 seconds. Seventy five μL of a 25% solution of polyethylene glycol (30004000 molecular weight, American Type Culture Collection) was added and the solution was gently vortexed for five seconds. Seventy five μL of 2.5 M CaCl$_2$ was added and the solution vortexed for five seconds. Following the addition of CaCl$_2$, the solution was incubated at room temperature for 10 to 15 minutes. The suspension was subsequently centrifuged for 20 seconds at 12,000 rpm (Sorval MC-12V centrifuge) and the supernatant discarded. The gold particle/DNA pellet was washed twice with 100% ethanol and resuspended in 10 mL 100% ethanol. The gold particle/DNA preparation was stored at −20° C. for up to two weeks.

DNA was introduced into maize cells using the electric discharge particle acceleration gene delivery device (U.S. Pat. No. 5,015,580). The gold particle/DNA suspension was coated on Mylar sheets (Du Pont Mylar polyester film type SMMC2, aluminum coated on one side, over coated with PVDC co-polymer on both sides, cut to 18 mm square) by dispersion of 310 to 320 μL of the gold particle/DNA suspension on a sheet. After the gold particle suspension settled for one to three minutes, excess ethanol was removed and the sheets were air dried. Microprojectile bombardment of maize tissue was conducted as described in U.S. Pat. No. 5,015,580. AC voltage may be varied in the electric discharge particle delivery device. For microprojectile bombardment of LH59 precultured immature embryos, 35% to 45% of maximum voltage was preferably used. Following microprojectile bombardment, tissue was cultured in the dark at 27° C.

Selection of Transformed Cells

Transformants were selected on culture medium comprising paromomycin, based on expression of a transgenic neomycin phosphotransferase II (nptII) gene. Twenty four hours after DNA delivery, tissue was transferred to 211V medium containing 25 mg/L paromomycin (medium 211 HV). After three weeks incubation in the dark at 27° C., tissue was transferred to medium 211 containing 50 mg/L paromomycin (medium 211G). Tissue was transferred to medium 211 containing 75 mg/L paromomycin (medium 211XX) after three weeks. Transformants were isolated following 9 weeks of selection.

Regeneration of Fertile Transgenic Plants

Fertile transgenic plants were produced from transformed maize cells. Transformed callus was transferred to medium 217 (N6 salts, 1 mg/L thiamine-HCl, 0.5 mg/L niacin, 3.52 mg/L benzylaminopurine, 0.91 mg/L L-asparagine monohydrate, 100 mg/L myo-inositol, 0.5 g/L MES, 1.6 g/L MgCl$_2$-6H$_2$O, 100 mg/L casein hydrolysate, 0.69 g/L L-proline, 20 g/L sucrose, 2 g/L GELGRO™, pH 5.8) for five to seven days in the dark at 27° C. Somatic embryos mature and shoot regeneration began on medium 217. Tissue was transferred to medium 127T (MS salts, 0.65 mg/L niacin, 0.125 mg/L pyridoxine-HCl, 0.125 mg/L thiamine-HCl, 0.125 mg/L Ca pantothenate, 150 mg/L L-asparagine, 100 mg/L myo-inositol, 10 g/L glucose, 20 g/L L-maltose, 100 mg/L paromomycin, 5.5 g PHYTAGAR™, pH 5.8) for shoot development. Tissue on medium 127T was cultured in the light at 400–600 lux at 26° C. Plantlets are transferred to soil, preferable 3 inch pots, about four to 6 weeks after transfer to 127T medium when the plantlets are about 3 inches tall and have roots. Plants were maintained for two weeks in a growth chamber at 26° C., followed by two weeks on a mist bench in a greenhouse before transplanting to 5 gallon pots for greenhouse growth. Plants were grown in the greenhouse to maturity and reciprocal pollinations were made with the inbred LH59. Seed was collected from plants and used for further breeding activities and future testing.

Planned Future Experiments

Transgenic corn data from first generation seed for pMON71250 is expected by the second quarter of 2002 and second generation data is expected by the end of 2002. First generation seed and dissected parts (germ and endosperm) will be analyzed by bench-top NMR and kernels harboring the transgene will be identified by PCR. Germ mass will be determined as part of this analysis. Differences in whole kernel % oil, germ % oil, endosperm % oil, germ and endosperm mass will be determined in a comparison between kernels harboring the transgene (identified by PCR) and null segregants (lacking the transgene). Analysis for protein and starch content may also be undertaken. Transgenic kernels will be analyzed for gross morphological differences, and kernels from different developmental stages may be sectioned (manually or optically) to detect morphological changes.

We claim:

1. An isolated nucleic acid molecule comprising a nucleotide sequence, or its complete complement, which encodes a polypeptide having at least 60% amino acid identity to the sequence of SEQ ID NO: 2 and having two AP2 DNA binding domains.

2. An isolated nucleic acid molecule comprising a nucleotide sequence, or its complete complement, which can hybridize under conditions of 6.0× sodium chloride/sodium citrate (SSC) at about 45° C. followed by a wash of 0.2×SSC at 50° C. for about 20 minutes to a second nucleic acid sequence which encodes a polypeptide having the amino acid sequence of SEQ ID NO:2 and wherein the nucleotide sequence encodes a protein having two AP2 domains.

3. An isolated nucleic acid sequence which encodes an amino acid sequence comprising SEQ ID NO: 2.

* * * * *

SEQUENCE LISTING

```
<160> NUMBER OF SEQ ID NOS: 33

<210> SEQ ID NO 1
<211> LENGTH: 2344
<212> TYPE: DNA
<213> ORGANISM: Glycine max
<220> FEATURE:
<221> NAME/KEY: CDS
<222> LOCATION: (242)..(2233)
<223> OTHER INFORMATION:

<400> SEQUENCE: 1
tgtgtgttga gcacatagaa cgatgagttt ggttggtaga ggagcaagtt ttgcattgta      60
gttgtagcaa tagcaacaca acacaacaaa acaaaaacca agtcttcatc atcttcatat     120
gcagagatta acatgatgat tagtttattt gccaagcaat gccttccttc gtgagatata     180
aactgctagc aatttcaaat cttttcgagt aaccaaaaag aaaaaaacaa aaagcaagaa     240 g atg aag cgc ata aat gag agt aac aac acc gat gat gga aac aat cat     289
  Met Lys Arg Ile Asn Glu Ser Asn Asn Thr Asp Asp Gly Asn Asn His
    1               5                  10                  15 aac tgg ttg ggg ttc tct ctc tca ccc cac atg aaa atg gag gct act     337
Asn Trp Leu Gly Phe Ser Leu Ser Pro His Met Lys Met Glu Ala Thr
             20                  25                  30 tca gca gcc act gtt ccg aca acc ttc tac atg tcc cct tct caa tct     385
Ser Ala Ala Thr Val Pro Thr Thr Phe Tyr Met Ser Pro Ser Gln Ser
         35                  40                  45 cac ttg tcc aac ttc gga atg tgt tac ggt gtc gga gaa aat ggt aac     433
His Leu Ser Asn Phe Gly Met Cys Tyr Gly Val Gly Glu Asn Gly Asn
     50                  55                  60 ttc cat tct cca ctt acg gtt atg cct ctc aag tct gat ggg tca ctt     481
Phe His Ser Pro Leu Thr Val Met Pro Leu Lys Ser Asp Gly Ser Leu
 65                  70                  75                  80 tgt atc ttg gaa gct ctc aaa aga tca caa acg caa gtg atg gtg cca     529
Cys Ile Leu Glu Ala Leu Lys Arg Ser Gln Thr Gln Val Met Val Pro
                 85                  90                  95 act tcg tct ccg aaa ttg gag gac ttt cta ggt ggt gca act atg gga     577
Thr Ser Ser Pro Lys Leu Glu Asp Phe Leu Gly Gly Ala Thr Met Gly
            100                 105                 110 act cac gaa tat gga agc cac gag aga ggt ttg agc cta gac agc atc     625
Thr His Glu Tyr Gly Ser His Glu Arg Gly Leu Ser Leu Asp Ser Ile
        115                 120                 125 tat tat aac tcc caa aac gca gag gct caa ccc aac aga gac ctt ctt     673
Tyr Tyr Asn Ser Gln Asn Ala Glu Ala Gln Pro Asn Arg Asp Leu Leu
    130                 135                 140
```

-continued

| | | |
|---|---|---|
| tca caa ccc ttc agg caa caa ggt cat atg agt gtc caa aca cac cct<br>Ser Gln Pro Phe Arg Gln Gln Gly His Met Ser Val Gln Thr His Pro<br>145                      150                      155                  160 | 721 |
| tat tac tca ggc ctt gct tgc cat ggt tta tat caa gca ccg ttg gag<br>Tyr Tyr Ser Gly Leu Ala Cys His Gly Leu Tyr Gln Ala Pro Leu Glu<br>                  165                     170                   175 | 769 |
| gaa gaa aca aca aag gaa acg cac gtg tcg gat tgc agc tcc cta atg<br>Glu Glu Thr Thr Lys Glu Thr His Val Ser Asp Cys Ser Ser Leu Met<br>          180                     185                   190 | 817 |
| cct caa atg aca gaa ggc ttg aaa aac tgg gtg gct cca aca agg gag<br>Pro Gln Met Thr Glu Gly Leu Lys Asn Trp Val Ala Pro Thr Arg Glu<br>         195                   200                  205 | 865 |
| ttt tca act cac cag cag gtt ttg gag cag caa atg aat tgt ggc atg<br>Phe Ser Thr His Gln Gln Val Leu Glu Gln Gln Met Asn Cys Gly Met<br>210                      215                     220 | 913 |
| ggg aat gag aga aat ggt gtg tct tta gga tct gtg ggg tgt gga gag<br>Gly Asn Glu Arg Asn Gly Val Ser Leu Gly Ser Val Gly Cys Gly Glu<br>225                      230                     235                   240 | 961 |
| tta cag tct cta agc tta tct atg agt cct ggt tct cag tct agt tgt<br>Leu Gln Ser Leu Ser Leu Ser Met Ser Pro Gly Ser Gln Ser Ser Cys<br>                  245                   250                   255 | 1009 |
| gtc act gct cct tct gga aca gat tct gtt gct gtg gat gca aag aag<br>Val Thr Ala Pro Ser Gly Thr Asp Ser Val Ala Val Asp Ala Lys Lys<br>          260                     265                   270 | 1057 |
| aga ggg cat gct aaa ctt ggt cag aag cag cct gtg cat aga aaa tct<br>Arg Gly His Ala Lys Leu Gly Gln Lys Gln Pro Val His Arg Lys Ser<br>                  275                   280                   285 | 1105 |
| atc gac aca ttt ggg caa aga acc tcg cag tat aga ggt gtc aca agg<br>Ile Asp Thr Phe Gly Gln Arg Thr Ser Gln Tyr Arg Gly Val Thr Arg<br>         290                   295                  300 | 1153 |
| cat aga tgg act ggt agg tat gaa gcg cat ttg tgg gat aat agt tgc<br>His Arg Trp Thr Gly Arg Tyr Glu Ala His Leu Trp Asp Asn Ser Cys<br>305                      310                     315                   320 | 1201 |
| aag aag gaa ggg caa act agg aaa gga cga caa gtg tat ttg ggg ggt<br>Lys Lys Glu Gly Gln Thr Arg Lys Gly Arg Gln Val Tyr Leu Gly Gly<br>                  325                   330                   335 | 1249 |
| tat gat atg gag gag aaa gct gca aga gcc tat gat ctc gcg gcc ctt<br>Tyr Asp Met Glu Glu Lys Ala Ala Arg Ala Tyr Asp Leu Ala Ala Leu<br>         340                     345                   350 | 1297 |
| aag tac tgg gga cct tca acg cat ata aac ttt tcg ata gag aat tac<br>Lys Tyr Trp Gly Pro Ser Thr His Ile Asn Phe Ser Ile Glu Asn Tyr<br>                  355                   360                   365 | 1345 |
| caa gtt caa ctt gag gaa atg aag aac atg agc aga cag gaa tac gtt<br>Gln Val Gln Leu Glu Glu Met Lys Asn Met Ser Arg Gln Glu Tyr Val<br>         370                     375                   380 | 1393 |
| gca cac ttg aga aga aaa agc agc ggg ttt tct aga ggt gct tca ata<br>Ala His Leu Arg Arg Lys Ser Ser Gly Phe Ser Arg Gly Ala Ser Ile<br>385                      390                     395                   400 | 1441 |
| tac aga ggg gtc aca agg cat cac caa cat gga aga tgg caa gcg agg<br>Tyr Arg Gly Val Thr Arg His His Gln His Gly Arg Trp Gln Ala Arg<br>                  405                   410                   415 | 1489 |
| ata ggc aga gtt gct ggg aac aaa gac ctt tac ctt ggg acg ttc agc<br>Ile Gly Arg Val Ala Gly Asn Lys Asp Leu Tyr Leu Gly Thr Phe Ser<br>         420                     425                   430 | 1537 |
| acc caa gag gaa gca gca gaa gca tac gat gta gcg gcg atc aaa ttt<br>Thr Gln Glu Glu Ala Ala Glu Ala Tyr Asp Val Ala Ala Ile Lys Phe<br>                  435                   440                   445 | 1585 |
| cgc ggc gca aat gca gtc aca aac ttt gac att tca aga tac gat gtg<br>Arg Gly Ala Asn Ala Val Thr Asn Phe Asp Ile Ser Arg Tyr Asp Val<br>         450                     455                   460 | 1633 |

| | | |
|---|---|---|
| gag aga atc atg gcc agt agc aat ctc ctc gct ggg gag ctt gca agg<br>Glu Arg Ile Met Ala Ser Ser Asn Leu Leu Ala Gly Glu Leu Ala Arg<br>465                          470                      475                     480 | | 1681 |
| cgt aag aaa gat aac gat cct aga aac aag gac ata gac tac aac aag<br>Arg Lys Lys Asp Asn Asp Pro Arg Asn Lys Asp Ile Asp Tyr Asn Lys<br>                      485                      490                      495 | | 1729 |
| agt gta gta aca agt gtg aac aat gag gaa acg gtt caa gtt caa gca<br>Ser Val Val Thr Ser Val Asn Asn Glu Glu Thr Val Gln Val Gln Ala<br>500                          505                      510 | | 1777 |
| gga aac aac aat aat gaa aac gac tca gag tgg aag atg gtt tta ttt<br>Gly Asn Asn Asn Asn Glu Asn Asp Ser Glu Trp Lys Met Val Leu Phe<br>              515                      520                      525 | | 1825 |
| aac cac cct tca cag cag caa cag gca aat ggc aat ggc agt gac caa<br>Asn His Pro Ser Gln Gln Gln Gln Ala Asn Gly Asn Gly Ser Asp Gln<br>530                          535                      540 | | 1873 |
| aaa ata atg aac tgt gga aat tac aga aac agt gca ttt tct atg gcc<br>Lys Ile Met Asn Cys Gly Asn Tyr Arg Asn Ser Ala Phe Ser Met Ala<br>545                          550                      555                     560 | | 1921 |
| cta caa gat ctt att ggg att gat tcg gtg ggt tct ggg cag cat aat<br>Leu Gln Asp Leu Ile Gly Ile Asp Ser Val Gly Ser Gly Gln His Asn<br>                      565                      570                      575 | | 1969 |
| atg ctg gac gag tct agc aaa att ggg act cat ttt tca aac acg tca<br>Met Leu Asp Glu Ser Ser Lys Ile Gly Thr His Phe Ser Asn Thr Ser<br>                580                      585                      590 | | 2017 |
| tcg ctg gtg aca agt tta agc agc tca aga gag gct agt cct gag aaa<br>Ser Leu Val Thr Ser Leu Ser Ser Ser Arg Glu Ala Ser Pro Glu Lys<br>              595                      600                     605 | | 2065 |
| agg ggt ccc tcg ctt ctg ttc cca atg cct cca atg gaa aca aag att<br>Arg Gly Pro Ser Leu Leu Phe Pro Met Pro Pro Met Glu Thr Lys Ile<br>610                          615                      620 | | 2113 |
| gtg aac ccc att ggt acc agt gtt acc tct tgg cta ccc tca cca acg<br>Val Asn Pro Ile Gly Thr Ser Val Thr Ser Trp Leu Pro Ser Pro Thr<br>625                          630                      635                     640 | | 2161 |
| gtt caa atg agg cct tct cct gct atc tct ttg tct cac ttg cca gtt<br>Val Gln Met Arg Pro Ser Pro Ala Ile Ser Leu Ser His Leu Pro Val<br>                      645                      650                     655 | | 2209 |
| ttt gct tct tgg act gat act taa atggagatag gcacggtcca tttttcatgt<br>Phe Ala Ser Trp Thr Asp Thr<br>              660 | | 2263 |
| tatgttatgt aactaaaatt tactttttc cttcatcttt tatttctaat ttgatttcct | | 2323 |
| aagtttaaaa aaaaaaaaaa a | | 2344 |

<210> SEQ ID NO 2
<211> LENGTH: 663
<212> TYPE: PRT
<213> ORGANISM: Glycine max

<400> SEQUENCE: 2

Met Lys Arg Ile Asn Glu Ser Asn Asn Thr Asp Asp Gly Asn Asn His
1                 5                    10                  15

Asn Trp Leu Gly Phe Ser Leu Ser Pro His Met Lys Met Glu Ala Thr
                20                    25                    30

Ser Ala Ala Thr Val Pro Thr Thr Phe Tyr Met Ser Pro Ser Gln Ser
                  35                    40                    45

His Leu Ser Asn Phe Gly Met Cys Tyr Gly Val Gly Glu Asn Gly Asn
            50                    55                    60

Phe His Ser Pro Leu Thr Val Met Pro Leu Lys Ser Asp Gly Ser Leu
65                 70                    75                    80

```
Cys Ile Leu Glu Ala Leu Lys Arg Ser Gln Thr Gln Val Met Val Pro
                85                  90                  95
Thr Ser Ser Pro Lys Leu Glu Asp Phe Leu Gly Gly Ala Thr Met Gly
            100                 105                 110
Thr His Glu Tyr Gly Ser His Glu Arg Gly Leu Ser Leu Asp Ser Ile
        115                 120                 125
Tyr Tyr Asn Ser Gln Asn Ala Glu Ala Gln Pro Asn Arg Asp Leu Leu
    130                 135                 140
Ser Gln Pro Phe Arg Gln Gln Gly His Met Ser Val Gln Thr His Pro
145                 150                 155                 160
Tyr Tyr Ser Gly Leu Ala Cys His Gly Leu Tyr Gln Ala Pro Leu Glu
                165                 170                 175
Glu Glu Thr Thr Lys Glu Thr His Val Ser Asp Cys Ser Ser Leu Met
            180                 185                 190
Pro Gln Met Thr Glu Gly Leu Lys Asn Trp Val Ala Pro Thr Arg Glu
        195                 200                 205
Phe Ser Thr His Gln Gln Val Leu Glu Gln Gln Met Asn Cys Gly Met
    210                 215                 220
Gly Asn Glu Arg Asn Gly Val Ser Leu Gly Ser Val Gly Cys Gly Glu
225                 230                 235                 240
Leu Gln Ser Leu Ser Leu Ser Met Ser Pro Gly Ser Gln Ser Ser Cys
                245                 250                 255
Val Thr Ala Pro Ser Gly Thr Asp Ser Val Ala Val Asp Ala Lys Lys
            260                 265                 270
Arg Gly His Ala Lys Leu Gly Gln Lys Gln Pro Val His Arg Lys Ser
        275                 280                 285
Ile Asp Thr Phe Gly Gln Arg Thr Ser Gln Tyr Arg Gly Val Thr Arg
    290                 295                 300
His Arg Trp Thr Gly Arg Tyr Glu Ala His Leu Trp Asp Asn Ser Cys
305                 310                 315                 320
Lys Lys Glu Gly Gln Thr Arg Lys Gly Arg Gln Val Tyr Leu Gly Gly
                325                 330                 335
Tyr Asp Met Glu Glu Lys Ala Ala Arg Ala Tyr Asp Leu Ala Ala Leu
            340                 345                 350
Lys Tyr Trp Gly Pro Ser Thr His Ile Asn Phe Ser Ile Glu Asn Tyr
        355                 360                 365
Gln Val Gln Leu Glu Glu Met Lys Asn Met Ser Arg Gln Glu Tyr Val
    370                 375                 380
Ala His Leu Arg Arg Lys Ser Ser Gly Phe Ser Arg Gly Ala Ser Ile
385                 390                 395                 400
Tyr Arg Gly Val Thr Arg His His Gln His Gly Arg Trp Gln Ala Arg
                405                 410                 415
Ile Gly Arg Val Ala Gly Asn Lys Asp Leu Tyr Leu Gly Thr Phe Ser
            420                 425                 430
Thr Gln Glu Glu Ala Ala Glu Ala Tyr Asp Val Ala Ala Ile Lys Phe
        435                 440                 445
Arg Gly Ala Asn Ala Val Thr Asn Phe Asp Ile Ser Arg Tyr Asp Val
    450                 455                 460
Glu Arg Ile Met Ala Ser Ser Asn Leu Leu Ala Gly Glu Leu Ala Arg
465                 470                 475                 480
Arg Lys Lys Asp Asn Asp Pro Arg Asn Lys Asp Ile Asp Tyr Asn Lys
                485                 490                 495
```

```
                                         -continued

Ser Val Val Thr Ser Val Asn Asn Glu Glu Thr Val Gln Val Gln Ala
            500                 505                 510

Gly Asn Asn Asn Glu Asn Asp Ser Glu Trp Lys Met Val Leu Phe
        515                 520                 525

Asn His Pro Ser Gln Gln Gln Ala Asn Gly Asn Gly Ser Asp Gln
    530                 535                 540

Lys Ile Met Asn Cys Gly Asn Tyr Arg Asn Ser Ala Phe Ser Met Ala
545                 550                 555                 560

Leu Gln Asp Leu Ile Gly Ile Asp Ser Val Gly Ser Gly Gln His Asn
                565                 570                 575

Met Leu Asp Glu Ser Ser Lys Ile Gly Thr His Phe Ser Asn Thr Ser
            580                 585                 590

Ser Leu Val Thr Ser Leu Ser Ser Arg Glu Ala Ser Pro Glu Lys
        595                 600                 605

Arg Gly Pro Ser Leu Leu Phe Pro Met Pro Met Glu Thr Lys Ile
    610                 615                 620

Val Asn Pro Ile Gly Thr Ser Val Thr Ser Trp Leu Pro Ser Pro Thr
625                 630                 635                 640

Val Gln Met Arg Pro Ser Pro Ala Ile Ser Leu Ser His Leu Pro Val
                645                 650                 655

Phe Ala Ser Trp Thr Asp Thr
                660

<210> SEQ ID NO 3
<211> LENGTH: 2323
<212> TYPE: DNA
<213> ORGANISM: Glycine max
<220> FEATURE:
<221> NAME/KEY: CDS
<222> LOCATION: (25)..(2022)
<223> OTHER INFORMATION:

<400> SEQUENCE: 3
gagtgttttg ttaagagaga aaaa atg aag agt atg gaa aat gat gac aat        51
                         Met Lys Ser Met Glu Asn Asp Asp Asn
                           1               5 gct gac ctt aat aat caa aac aat tgg ttg ggt ttc tca ctc tct cct      99
Ala Asp Leu Asn Asn Gln Asn Asn Trp Leu Gly Phe Ser Leu Ser Pro
 10                  15                  20                  25 caa atg cat aat ata gga gtt tct tca cac tca caa cct tcc tct gct    147
Gln Met His Asn Ile Gly Val Ser Ser His Ser Gln Pro Ser Ser Ala
                 30                  35                  40 gct gaa gtg gtt cct aca agc ttt tac cac cac act gct cca ctt agt    195
Ala Glu Val Val Pro Thr Ser Phe Tyr His His Thr Ala Pro Leu Ser
             45                  50                  55 agc tat ggt ttc tac tat gga ctt gaa gct gaa aat gtt gga ttg tat    243
Ser Tyr Gly Phe Tyr Tyr Gly Leu Glu Ala Glu Asn Val Gly Leu Tyr
         60                  65                  70 tca gct ttg cca atc atg ccc ctc aaa tct gat ggc tct ctc tat gga    291
Ser Ala Leu Pro Ile Met Pro Leu Lys Ser Asp Gly Ser Leu Tyr Gly
     75                  80                  85 ttg gaa act tta agc agg tca caa gca caa gca atg gct act act tca    339
Leu Glu Thr Leu Ser Arg Ser Gln Ala Gln Ala Met Ala Thr Thr Ser
 90                  95                 100                 105 aca cca aaa ctg gag aac ttc tta ggt ggg gaa gcc atg ggg acc cct    387
Thr Pro Lys Leu Glu Asn Phe Leu Gly Gly Glu Ala Met Gly Thr Pro
                110                 115                 120
```

```
cat cac tac gaa tgt agt gcc aca gaa aca atg cct ctg agc tta gac      435
His His Tyr Glu Cys Ser Ala Thr Glu Thr Met Pro Leu Ser Leu Asp
            125                 130                 135 agt gtt ttt tac atc caa ccc tca cgc cgt gac cca aat aat aac caa      483
Ser Val Phe Tyr Ile Gln Pro Ser Arg Arg Asp Pro Asn Asn Asn Gln
        140                 145                 150 acc tac caa aac cat gtt caa cac att agc acc aac caa caa caa caa      531
Thr Tyr Gln Asn His Val Gln His Ile Ser Thr Asn Gln Gln Gln Gln
        155                 160                 165 cag caa gag ctt caa gca tat tac tct acc ttg aga aac cat gat atg      579
Gln Gln Glu Leu Gln Ala Tyr Tyr Ser Thr Leu Arg Asn His Asp Met
170                 175                 180                 185 ata tta gaa ggg tca aag caa agc caa act tct gac aac aac aat ctt      627
Ile Leu Glu Gly Ser Lys Gln Ser Gln Thr Ser Asp Asn Asn Asn Leu
                190                 195                 200 cat gtt caa aac atg ggt ggt gat gat gcc gtt cct gtt cct ggc ctc      675
His Val Gln Asn Met Gly Gly Asp Asp Ala Val Pro Val Pro Gly Leu
            205                 210                 215 aag agt tgg gaa gtg agg aac ttc caa gct agc cat gca cat gag tca      723
Lys Ser Trp Glu Val Arg Asn Phe Gln Ala Ser His Ala His Glu Ser
        220                 225                 230 aag atg att gtt cct cat gtg gag gaa aat gct ggt gaa tca ggg tcc      771
Lys Met Ile Val Pro His Val Glu Glu Asn Ala Gly Glu Ser Gly Ser
        235                 240                 245 att gga tca atg gct tat ggt gac ttg caa tcg ttg agc ttg tcc atg      819
Ile Gly Ser Met Ala Tyr Gly Asp Leu Gln Ser Leu Ser Leu Ser Met
250                 255                 260                 265 agt cct agc tct cag tct agc agt gtc aca agt tct cac cgt gct tca      867
Ser Pro Ser Ser Gln Ser Ser Ser Val Thr Ser Ser His Arg Ala Ser
                270                 275                 280 cct gct gtc gtt gat tct gtt gcc atg gat act aag aaa agg ggg cct      915
Pro Ala Val Val Asp Ser Val Ala Met Asp Thr Lys Lys Arg Gly Pro
            285                 290                 295 gaa aag gtt gac cag aag caa att gtt cat agg aag tcc att gac acc      963
Glu Lys Val Asp Gln Lys Gln Ile Val His Arg Lys Ser Ile Asp Thr
        300                 305                 310 ttt gga caa aga acc tcc cag tat aga gga gta aca agg cat agg tgg     1011
Phe Gly Gln Arg Thr Ser Gln Tyr Arg Gly Val Thr Arg His Arg Trp
        315                 320                 325 act ggg aga tat gaa gct cat ctt tgg gac aac agc tgc aag aaa gag     1059
Thr Gly Arg Tyr Glu Ala His Leu Trp Asp Asn Ser Cys Lys Lys Glu
330                 335                 340                 345 ggg caa agc agg aaa gga aga caa gtt tat cta ggg ggt tat gat atg     1107
Gly Gln Ser Arg Lys Gly Arg Gln Val Tyr Leu Gly Gly Tyr Asp Met
                350                 355                 360 gaa gaa aaa gct gcg aga gct tat gat cta gcg gca ctc aag tat tgg     1155
Glu Glu Lys Ala Ala Arg Ala Tyr Asp Leu Ala Ala Leu Lys Tyr Trp
            365                 370                 375 gga ccc tcc act cac ata aac ttt cct ttg gaa aat tat caa aat gaa     1203
Gly Pro Ser Thr His Ile Asn Phe Pro Leu Glu Asn Tyr Gln Asn Glu
        380                 385                 390 ctt gag gaa atg aag aac atg act aga caa gag tat gtt gct cat ttg     1251
Leu Glu Glu Met Lys Asn Met Thr Arg Gln Glu Tyr Val Ala His Leu
        395                 400                 405 aga aga aaa agc agc gga ttc tca aga ggg gct tcc atg tac aga gga     1299
Arg Arg Lys Ser Ser Gly Phe Ser Arg Gly Ala Ser Met Tyr Arg Gly
410                 415                 420                 425 gta aca aga cac cac caa cat gga agg tgg caa gct cga att ggt aga     1347
Val Thr Arg His His Gln His Gly Arg Trp Gln Ala Arg Ile Gly Arg
                430                 435                 440
```

```
gtg gct gga aac aaa gat cta tat ctt gga acc ttt agt aca caa gag    1395
Val Ala Gly Asn Lys Asp Leu Tyr Leu Gly Thr Phe Ser Thr Gln Glu
            445                 450                 455 gaa gca gct gaa gcc tat gat att gct gct ata aaa ttc cga gga gcg    1443
Glu Ala Ala Glu Ala Tyr Asp Ile Ala Ala Ile Lys Phe Arg Gly Ala
            460                 465                 470 aat gct gta acc aac ttt gac atc aca aga tat gat gtg gag aaa atc    1491
Asn Ala Val Thr Asn Phe Asp Ile Thr Arg Tyr Asp Val Glu Lys Ile
        475                 480                 485 atg gca agc agc aac ctc ctt agc agt gag cta gct agg cgc aac cga    1539
Met Ala Ser Ser Asn Leu Leu Ser Ser Glu Leu Ala Arg Arg Asn Arg
490                 495                 500                 505 gag acg gac aat gaa act cag tgc att gat caa aat cac aat aag cct    1587
Glu Thr Asp Asn Glu Thr Gln Cys Ile Asp Gln Asn His Asn Lys Pro
                510                 515                 520 tct gca tat gag gac act caa gaa gct att cta atg cac cag aag agc    1635
Ser Ala Tyr Glu Asp Thr Gln Glu Ala Ile Leu Met His Gln Lys Ser
            525                 530                 535 tgt gag agc gaa aat gat cag tgg aag atg gtt ctc tac caa tcc tct    1683
Cys Glu Ser Glu Asn Asp Gln Trp Lys Met Val Leu Tyr Gln Ser Ser
            540                 545                 550 cag caa ctt gag cag aat cca cca aca att gag agt gac aga act aac    1731
Gln Gln Leu Glu Gln Asn Pro Pro Thr Ile Glu Ser Asp Arg Thr Asn
        555                 560                 565 cag tcc ttc gca gtg gct ttg gac aac atg ttt cat cag gaa gta gag    1779
Gln Ser Phe Ala Val Ala Leu Asp Asn Met Phe His Gln Glu Val Glu
570                 575                 580                 585 gaa tca agt aag gcg agg acg cat gtg tca aat cct tct tca ttg gcc    1827
Glu Ser Ser Lys Ala Arg Thr His Val Ser Asn Pro Ser Ser Leu Ala
                590                 595                 600 aca agt ttg agc agc tca aga gaa ggt agc cct gat agg aca agc ttg    1875
Thr Ser Leu Ser Ser Ser Arg Glu Gly Ser Pro Asp Arg Thr Ser Leu
            605                 610                 615 cca atg ctc tct gga atg cct tca act gca tca aaa cta ttg gct act    1923
Pro Met Leu Ser Gly Met Pro Ser Thr Ala Ser Lys Leu Leu Ala Thr
            620                 625                 630 aat cca aat aac gtg aat tct tgg gac cct tca ccc cat ttg agg cca    1971
Asn Pro Asn Asn Val Asn Ser Trp Asp Pro Ser Pro His Leu Arg Pro
        635                 640                 645 gca ctt act ttg cct caa atg cca gtt ttt gca gct tgg aca gat gca    2019
Ala Leu Thr Leu Pro Gln Met Pro Val Phe Ala Ala Trp Thr Asp Ala
650                 655                 660                 665 tag ttcatagctc aatagtcctt ttaatttttt gttctctcaa gtgaaatttc         2072
aatccttttt attgtctttt tttgcatgca tgaacaacac aagaggaagg ggttgtagct  2132
agtcaaatgg agggtctaaa tattatatca tcacatcact gtcagcaagt ttaatttaaa  2192 cttttcaaatc attacatttt agcattttac tagttaagaa ttcctgaatt ttcattttca 2252 ttttcaatat atccttgtgg ccagattttg tcaattcatt cattgataga aacggaaaaa  2312
aaaaaaaaaa a                                                       2323

<210> SEQ ID NO 4
<211> LENGTH: 665
<212> TYPE: PRT
<213> ORGANISM: Glycine max
```

<400> SEQUENCE: 4

```
Met Lys Ser Met Glu Asn Asp Asn Ala Asp Leu Asn Asn Gln Asn
1               5                   10                  15

Asn Trp Leu Gly Phe Ser Leu Ser Pro Gln Met His Asn Ile Gly Val
            20                  25                  30

Ser Ser His Ser Gln Pro Ser Ser Ala Ala Glu Val Val Pro Thr Ser
        35                  40                  45

Phe Tyr His His Thr Ala Pro Leu Ser Ser Tyr Gly Phe Tyr Tyr Gly
    50                  55                  60

Leu Glu Ala Glu Asn Val Gly Leu Tyr Ser Ala Leu Pro Ile Met Pro
65                  70                  75                  80

Leu Lys Ser Asp Gly Ser Leu Tyr Gly Leu Glu Thr Leu Ser Arg Ser
                85                  90                  95

Gln Ala Gln Ala Met Ala Thr Thr Ser Thr Pro Lys Leu Glu Asn Phe
                100                 105                 110

Leu Gly Gly Glu Ala Met Gly Thr Pro His His Tyr Glu Cys Ser Ala
            115                 120                 125

Thr Glu Thr Met Pro Leu Ser Leu Asp Ser Val Phe Tyr Ile Gln Pro
    130                 135                 140

Ser Arg Arg Asp Pro Asn Asn Asn Gln Thr Tyr Gln Asn His Val Gln
145                 150                 155                 160

His Ile Ser Thr Asn Gln Gln Gln Gln Gln Glu Leu Gln Ala Tyr
                165                 170                 175

Tyr Ser Thr Leu Arg Asn His Asp Met Ile Leu Glu Gly Ser Lys Gln
            180                 185                 190

Ser Gln Thr Ser Asp Asn Asn Asn Leu His Val Gln Asn Met Gly Gly
            195                 200                 205

Asp Asp Ala Val Pro Val Pro Gly Leu Lys Ser Trp Glu Val Arg Asn
210                 215                 220

Phe Gln Ala Ser His Ala His Glu Ser Lys Met Ile Val Pro His Val
225                 230                 235                 240

Glu Glu Asn Ala Gly Glu Ser Gly Ser Ile Gly Ser Met Ala Tyr Gly
                245                 250                 255

Asp Leu Gln Ser Leu Ser Leu Ser Met Ser Pro Ser Ser Gln Ser Ser
            260                 265                 270

Ser Val Thr Ser Ser His Arg Ala Ser Pro Ala Val Val Asp Ser Val
    275                 280                 285

Ala Met Asp Thr Lys Lys Arg Gly Pro Glu Lys Val Asp Gln Lys Gln
    290                 295                 300

Ile Val His Arg Lys Ser Ile Asp Thr Phe Gly Gln Arg Thr Ser Gln
305                 310                 315                 320

Tyr Arg Gly Val Thr Arg His Arg Trp Thr Gly Arg Tyr Glu Ala His
                325                 330                 335

Leu Trp Asp Asn Ser Cys Lys Lys Glu Gly Gln Ser Arg Lys Gly Arg
            340                 345                 350

Gln Val Tyr Leu Gly Gly Tyr Asp Met Glu Lys Ala Ala Arg Ala
            355                 360                 365

Tyr Asp Leu Ala Ala Leu Lys Tyr Trp Gly Pro Ser Thr His Ile Asn
    370                 375                 380

Phe Pro Leu Glu Asn Tyr Gln Asn Glu Leu Glu Glu Met Lys Asn Met
385                 390                 395                 400

Thr Arg Gln Glu Tyr Val Ala His Leu Arg Arg Lys Ser Ser Gly Phe
                405                 410                 415
```

```
Ser Arg Gly Ala Ser Met Tyr Arg Gly Val Thr Arg His His Gln His
            420                 425                 430

Gly Arg Trp Gln Ala Arg Ile Gly Arg Val Ala Gly Asn Lys Asp Leu
            435                 440                 445

Tyr Leu Gly Thr Phe Ser Thr Gln Glu Glu Ala Ala Glu Ala Tyr Asp
        450                 455                 460

Ile Ala Ala Ile Lys Phe Arg Gly Ala Asn Ala Val Thr Asn Phe Asp
465                 470                 475                 480

Ile Thr Arg Tyr Asp Val Glu Lys Ile Met Ala Ser Ser Asn Leu Leu
                485                 490                 495

Ser Ser Glu Leu Ala Arg Arg Asn Arg Glu Thr Asp Asn Glu Thr Gln
            500                 505                 510

Cys Ile Asp Gln Asn His Asn Lys Pro Ser Ala Tyr Glu Asp Thr Gln
        515                 520                 525

Glu Ala Ile Leu Met His Gln Lys Ser Cys Glu Ser Glu Asn Asp Gln
    530                 535                 540

Trp Lys Met Val Leu Tyr Gln Ser Ser Gln Gln Leu Glu Gln Asn Pro
545                 550                 555                 560

Pro Thr Ile Glu Ser Asp Arg Thr Asn Gln Ser Phe Ala Val Ala Leu
                565                 570                 575

Asp Asn Met Phe His Gln Glu Val Glu Glu Ser Ser Lys Ala Arg Thr
            580                 585                 590

His Val Ser Asn Pro Ser Ser Leu Ala Thr Ser Leu Ser Ser Ser Arg
        595                 600                 605

Glu Gly Ser Pro Asp Arg Thr Ser Leu Pro Met Leu Ser Gly Met Pro
    610                 615                 620

Ser Thr Ala Ser Lys Leu Leu Ala Thr Asn Pro Asn Asn Val Asn Ser
625                 630                 635                 640

Trp Asp Pro Ser Pro His Leu Arg Pro Ala Leu Thr Leu Pro Gln Met
                645                 650                 655

Pro Val Phe Ala Ala Trp Thr Asp Ala
            660                 665

<210> SEQ ID NO 5
<211> LENGTH: 1926
<212> TYPE: DNA
<213> ORGANISM: Oryza sativa
<220> FEATURE:
<221> NAME/KEY: CDS
<222> LOCATION: (1)..(1926)
<223> OTHER INFORMATION:

<400> SEQUENCE: 5 atg gcc agc ggc ggc ggc agc agc aac tgg tta ggc ttc tcg ctc tcc      48
Met Ala Ser Gly Gly Gly Ser Ser Asn Trp Leu Gly Phe Ser Leu Ser
1               5                   10                  15 ccg cac atg ccg gcc atg gag gtg ccg tcc tcc tct gag cca tcg act      96
Pro His Met Pro Ala Met Glu Val Pro Ser Ser Ser Glu Pro Ser Thr
            20                  25                  30 gct gct cat cat cat cat cat cat cca cct gct gct gct gct gct           144
Ala Ala His His His His His His Pro Pro Ala Ala Ala Ala Ala
        35                  40                  45 gcc gga gcc atg tcg tct cct ccc gac agc gcc acg acc tgc aac ttc      192
Ala Gly Ala Met Ser Ser Pro Pro Asp Ser Ala Thr Thr Cys Asn Phe
    50                  55                  60 ctc ttc tcc cct cct gca gca cag atg gtc gct cct tca cct ggc tac      240
Leu Phe Ser Pro Pro Ala Ala Gln Met Val Ala Pro Ser Pro Gly Tyr
65                  70                  75                  80
```

| | | |
|---|---|---|
| tac tac gtc ggc ggc gcc tac gga gac ggg acc agc acc gcc ggc gtc<br>Tyr Tyr Val Gly Gly Ala Tyr Gly Asp Gly Thr Ser Thr Ala Gly Val<br>                    85                         90                       95 | 288 |
| tac tac tcg cac ctc cct gtc atg cct atc aag tcc gat ggc tcc ctc<br>Tyr Tyr Ser His Leu Pro Val Met Pro Ile Lys Ser Asp Gly Ser Leu<br>                    100                        105                    110 | 336 |
| tgc atc atg gaa ggc atg atg ccg tcg tca tcg cca aag ctc gag gac<br>Cys Ile Met Glu Gly Met Met Pro Ser Ser Ser Pro Lys Leu Glu Asp<br>                  115                        120                    125 | 384 |
| ttc ttg ggg tgt ggc aat ggc agt ggc cat gac ccg gcc acc tac tat<br>Phe Leu Gly Cys Gly Asn Gly Ser Gly His Asp Pro Ala Thr Tyr Tyr<br>      130                        135                        140 | 432 |
| agc cag ggc caa gaa gca gag gat gca agc agg gcg gcc tac cag cac<br>Ser Gln Gly Gln Glu Ala Glu Asp Ala Ser Arg Ala Ala Tyr Gln His<br>145                    150                        155                    160 | 480 |
| cac cag cta gtc ccc tac aac tac cag cca ttg acg gaa gca gag atg<br>His Gln Leu Val Pro Tyr Asn Tyr Gln Pro Leu Thr Glu Ala Glu Met<br>                    165                        170                    175 | 528 |
| ctg caa gag gcc gca gcg gcg cca atg gag gac gca atg gcg gcg gcc<br>Leu Gln Glu Ala Ala Ala Ala Pro Met Glu Asp Ala Met Ala Ala Ala<br>            180                        185                        190 | 576 |
| aag aac ttc ctc gtc acc agc tac ggc gcc tgc tac ggc aac cag gag<br>Lys Asn Phe Leu Val Thr Ser Tyr Gly Ala Cys Tyr Gly Asn Gln Glu<br>                    195                        200                    205 | 624 |
| atg ccg cag ccg ctc agc ctc tcc atg agc cca ggg tcc cag tcc agc<br>Met Pro Gln Pro Leu Ser Leu Ser Met Ser Pro Gly Ser Gln Ser Ser<br>      210                        215                        220 | 672 |
| agc tgc gtc agt gca gct ccc cag cag cat cag cag atg gcg gtg gtc<br>Ser Cys Val Ser Ala Ala Pro Gln Gln His Gln Gln Met Ala Val Val<br>225                    230                        235                    240 | 720 |
| gct gca gct gct gct gct ggt gat ggc cag gga agc aac agt aat gac<br>Ala Ala Ala Ala Ala Ala Gly Asp Gly Gln Gly Ser Asn Ser Asn Asp<br>                        245                        250                    255 | 768 |
| ggt ggc gag cag cgt gtc ggg aag aag agg ggc acc ggg aaa ggg ggc<br>Gly Gly Glu Gln Arg Val Gly Lys Lys Arg Gly Thr Gly Lys Gly Gly<br>            260                        265                        270 | 816 |
| caa aag cag cct gtt cac cgg aag tcc att gac acg ttt ggg cag agg<br>Gln Lys Gln Pro Val His Arg Lys Ser Ile Asp Thr Phe Gly Gln Arg<br>                275                        280                    285 | 864 |
| aca tcg cag tat agg ggc gtc acc agg cac agg tgg act gga aga tat<br>Thr Ser Gln Tyr Arg Gly Val Thr Arg His Arg Trp Thr Gly Arg Tyr<br>      290                        295                        300 | 912 |
| gaa gcc cac ctc tgg gat aac agt tgc aaa aag gat gga cag aca agg<br>Glu Ala His Leu Trp Asp Asn Ser Cys Lys Lys Asp Gly Gln Thr Arg<br>305                    310                        315                    320 | 960 |
| aag gga agg caa gta tat cta ggt ggt tat gac act gaa gat aaa gct<br>Lys Gly Arg Gln Val Tyr Leu Gly Gly Tyr Asp Thr Glu Asp Lys Ala<br>                        325                        330                    335 | 1008 |
| gcg agg gct tat gat ctg gct gcg ctg aaa tac tgg ggg cta tct acg<br>Ala Arg Ala Tyr Asp Leu Ala Ala Leu Lys Tyr Trp Gly Leu Ser Thr<br>                340                        345                    350 | 1056 |
| cat ata aat ttc ccg tta gaa aac tac cga gat gag atc gag gag atg<br>His Ile Asn Phe Pro Leu Glu Asn Tyr Arg Asp Glu Ile Glu Glu Met<br>                        355                        360                    365 | 1104 |
| gaa agg atg aca agg caa gaa tat gtt gcg cac ttg aga agg aga agc<br>Glu Arg Met Thr Arg Gln Glu Tyr Val Ala His Leu Arg Arg Arg Ser<br>      370                        375                        380 | 1152 |
| agc ggg ttc tct cgc ggt gct tcc atc tac cgg gga gta aca agg cat<br>Ser Gly Phe Ser Arg Gly Ala Ser Ile Tyr Arg Gly Val Thr Arg His<br>385                    390                        395                    400 | 1200 |

| | | |
|---|---|---|
| cac cag cat gga aga tgg caa gct cgg att ggc agg gtt gct ggc aac<br>His Gln His Gly Arg Trp Gln Ala Arg Ile Gly Arg Val Ala Gly Asn<br>405 410 415 | 1248 |
| aag gac ttg tat ctc ggc act ttc agc act caa gaa gaa gca gca gag<br>Lys Asp Leu Tyr Leu Gly Thr Phe Ser Thr Gln Glu Glu Ala Ala Glu<br>420 425 430 | 1296 |
| gca tac gac att gct gcc atc aag ttc cgt ggc ctg aac gcg gtg acg<br>Ala Tyr Asp Ile Ala Ala Ile Lys Phe Arg Gly Leu Asn Ala Val Thr<br>435 440 445 | 1344 |
| aac ttt gac atc aca agg tac gac gtg gac aag atc atg gag agc agc<br>Asn Phe Asp Ile Thr Arg Tyr Asp Val Asp Lys Ile Met Glu Ser Ser<br>450 455 460 | 1392 |
| tcg ctg ctg cct ggt gag gca gcg cgt aag gtg aag gcg atc gag gca<br>Ser Leu Leu Pro Gly Glu Ala Ala Arg Lys Val Lys Ala Ile Glu Ala<br>465 470 475 480 | 1440 |
| gcg ccg gac cat gtg cca ata ggc cgc gag ctc ggt gcg acc gag gaa<br>Ala Pro Asp His Val Pro Ile Gly Arg Glu Leu Gly Ala Thr Glu Glu<br>485 490 495 | 1488 |
| gcg agc gct gct act gtc acg ggc acc gac tgg aga atg gtg ctc cat<br>Ala Ser Ala Ala Thr Val Thr Gly Thr Asp Trp Arg Met Val Leu His<br>500 505 510 | 1536 |
| gga tca cag cag cag caa gct gca gcg tgc acc gaa gca acg gca gat<br>Gly Ser Gln Gln Gln Gln Ala Ala Ala Cys Thr Glu Ala Thr Ala Asp<br>515 520 525 | 1584 |
| ctt cag aag ggc ttc atg ggt gac gcg cac tcg gct ctc cac ggc att<br>Leu Gln Lys Gly Phe Met Gly Asp Ala His Ser Ala Leu His Gly Ile<br>530 535 540 | 1632 |
| gtc ggg ttc gac gtc gag tcg gcg gca gct gac gag atc gat gtc ccg<br>Val Gly Phe Asp Val Glu Ser Ala Ala Ala Asp Glu Ile Asp Val Pro<br>545 550 555 560 | 1680 |
| gga ggg aag atc agt ggc atc aac ttc tcg aac tcg tct tcg ctg gtg<br>Gly Gly Lys Ile Ser Gly Ile Asn Phe Ser Asn Ser Ser Ser Leu Val<br>565 570 575 | 1728 |
| act agc ctg agc aac tcg agg gag ggg agc cct gag agg ctt ggc ctc<br>Thr Ser Leu Ser Asn Ser Arg Glu Gly Ser Pro Glu Arg Leu Gly Leu<br>580 585 590 | 1776 |
| gcc atg ctc tac gcc aag cat cat ccc acc gcc gtc agc ctc gcc gcc<br>Ala Met Leu Tyr Ala Lys His His Pro Thr Ala Val Ser Leu Ala Ala<br>595 600 605 | 1824 |
| atg aac ccc tgg atg ccg atg ccg gcg ccg gcc gca gct cac gtg atg<br>Met Asn Pro Trp Met Pro Met Pro Ala Pro Ala Ala His Val Met<br>610 615 620 | 1872 |
| agg ccg ccg agt gcc att gct cat ctc cct gtt ttt gca gcc tgg aca<br>Arg Pro Pro Ser Ala Ile Ala His Leu Pro Val Phe Ala Ala Trp Thr<br>625 630 635 640 | 1920 |
| gat gcc<br>Asp Ala | 1926 |

<210> SEQ ID NO 6
<211> LENGTH: 642
<212> TYPE: PRT
<213> ORGANISM: Oryza sativa

<400> SEQUENCE: 6

Met Ala Ser Gly Gly Gly Ser Ser Asn Trp Leu Gly Phe Ser Leu Ser
1               5                   10                  15

Pro His Met Pro Ala Met Glu Val Pro Ser Ser Glu Pro Ser Thr
            20                  25                  30

Ala Ala His His His His His His Pro Pro Ala Ala Ala Ala
        35                  40                  45

-continued

```
Ala Gly Ala Met Ser Ser Pro Pro Asp Ser Ala Thr Thr Cys Asn Phe
 50              55                  60

Leu Phe Ser Pro Pro Ala Ala Gln Met Val Ala Pro Ser Pro Gly Tyr
 65                  70                  75                  80

Tyr Tyr Val Gly Gly Ala Tyr Gly Asp Gly Thr Ser Thr Ala Gly Val
                 85                  90                  95

Tyr Tyr Ser His Leu Pro Val Met Pro Ile Lys Ser Asp Gly Ser Leu
                100                 105                 110

Cys Ile Met Glu Gly Met Met Pro Ser Ser Ser Pro Lys Leu Glu Asp
                115                 120                 125

Phe Leu Gly Cys Gly Asn Gly Ser Gly His Asp Pro Ala Thr Tyr Tyr
130                 135                 140

Ser Gln Gly Gln Glu Ala Glu Asp Ala Ser Arg Ala Ala Tyr Gln His
145                 150                 155                 160

His Gln Leu Val Pro Tyr Asn Tyr Gln Pro Leu Thr Glu Ala Glu Met
                165                 170                 175

Leu Gln Glu Ala Ala Ala Ala Pro Met Glu Asp Ala Met Ala Ala Ala
                180                 185                 190

Lys Asn Phe Leu Val Thr Ser Tyr Gly Ala Cys Tyr Gly Asn Gln Glu
                195                 200                 205

Met Pro Gln Pro Leu Ser Leu Ser Met Ser Pro Gly Ser Gln Ser Ser
210                 215                 220

Ser Cys Val Ser Ala Ala Pro Gln Gln His Gln Gln Met Ala Val Val
225                 230                 235                 240

Ala Ala Ala Ala Ala Gly Asp Gly Gln Gly Ser Asn Ser Asn Asp
                245                 250                 255

Gly Gly Glu Gln Arg Val Gly Lys Lys Arg Gly Thr Gly Lys Gly Gly
                260                 265                 270

Gln Lys Gln Pro Val His Arg Lys Ser Ile Asp Thr Phe Gly Gln Arg
                275                 280                 285

Thr Ser Gln Tyr Arg Gly Val Thr Arg His Arg Trp Thr Gly Arg Tyr
290                 295                 300

Glu Ala His Leu Trp Asp Asn Ser Cys Lys Lys Asp Gly Gln Thr Arg
305                 310                 315                 320

Lys Gly Arg Gln Val Tyr Leu Gly Gly Tyr Asp Thr Glu Asp Lys Ala
                325                 330                 335

Ala Arg Ala Tyr Asp Leu Ala Ala Leu Lys Tyr Trp Gly Leu Ser Thr
                340                 345                 350

His Ile Asn Phe Pro Leu Glu Asn Tyr Arg Asp Glu Ile Glu Glu Met
                355                 360                 365

Glu Arg Met Thr Arg Gln Glu Tyr Val Ala His Leu Arg Arg Arg Ser
                370                 375                 380

Ser Gly Phe Ser Arg Gly Ala Ser Ile Tyr Arg Gly Val Thr Arg His
385                 390                 395                 400

His Gln His Gly Arg Trp Gln Ala Arg Ile Gly Arg Val Ala Gly Asn
                405                 410                 415

Lys Asp Leu Tyr Leu Gly Thr Phe Ser Thr Gln Glu Glu Ala Ala Glu
                420                 425                 430

Ala Tyr Asp Ile Ala Ala Ile Lys Phe Arg Gly Leu Asn Ala Val Thr
                435                 440                 445

Asn Phe Asp Ile Thr Arg Tyr Asp Val Asp Lys Ile Met Glu Ser Ser
450                 455                 460
```

-continued

| | | | | | | | | | | | | |
|---|---|---|---|---|---|---|---|---|---|---|---|---|
| Ser | Leu | Leu | Pro | Gly | Glu | Ala | Ala | Arg | Lys | Val | Lys | Ala | Ile | Glu | Ala |
| 465 | | | | 470 | | | | 475 | | | | 480 | | | |

Ser Leu Leu Pro Gly Glu Ala Ala Arg Lys Val Lys Ala Ile Glu Ala
465                 470                 475                 480

Ala Pro Asp His Val Pro Ile Gly Arg Glu Leu Gly Ala Thr Glu Glu
                485                 490                 495

Ala Ser Ala Ala Thr Val Thr Gly Thr Asp Trp Arg Met Val Leu His
            500                 505                 510

Gly Ser Gln Gln Gln Ala Ala Ala Cys Thr Glu Ala Thr Ala Asp
        515                 520                 525

Leu Gln Lys Gly Phe Met Gly Asp Ala His Ser Ala Leu His Gly Ile
    530                 535                 540

Val Gly Phe Asp Val Glu Ser Ala Ala Ala Asp Glu Ile Asp Val Pro
545                 550                 555                 560

Gly Gly Lys Ile Ser Gly Ile Asn Phe Ser Asn Ser Ser Ser Leu Val
                565                 570                 575

Thr Ser Leu Ser Asn Ser Arg Glu Gly Ser Pro Glu Arg Leu Gly Leu
            580                 585                 590

Ala Met Leu Tyr Ala Lys His His Pro Thr Ala Val Ser Leu Ala Ala
        595                 600                 605

Met Asn Pro Trp Met Pro Met Pro Ala Pro Ala Ala His Val Met
    610                 615                 620

Arg Pro Pro Ser Ala Ile Ala His Leu Pro Val Phe Ala Ala Trp Thr
625                 630                 635                 640

Asp Ala

<210> SEQ ID NO 7
<211> LENGTH: 7367
<212> TYPE: DNA
<213> ORGANISM: Oryza sativa

<400> SEQUENCE: 7

```
ataattagcg actgattact gtagcatcac tgtagcaaat catggattaa tatacctcgt      60
tagattcgtc tcgcaaaata gcctagggt taaggaatgc gttttgtcag taatctacgt     120
ttaatactcc taaatagcaa gattctggag ggctatttaa tagccctccg gatccaaaca    180
gggccatgtt tagatttaaa cttttttct tcaaatttcc aacttttctg tcacatcgaa    240
ctttcctgca tacacaaact tccaactttt ccgtcacatc gttccaattt acttaaactt    300
ttaattttag cgtggaacta acaaagcgc tagtgtgtat ttctagctat acacaacata    360
aattgaggat gccatttaaa ggttggttaa ctttatagac ttgcaaatga atctctttac    420
tctcgtcgta ctactccact catcgtctaa aaatataatt ttgggttggt taagagagt     480
tgagaccggc tttatcccat tttattataa aaatcaaac tcggatcatt tcaaaaacag    540
aagctgagat ttggtgttgt aagagtacat atcattggac aatatcgcca atatcaaacc    600
ctgggttttc acttaccggt tttaagggtc cctttaaatt ataggatta aaaaaataaa    660
gaaacaagaa aaaacacatg attttgaagc cgtaacaaaa aattgcaaaa catagaaaaa    720
aaaacataga aatgactgtt tgatttctta ggaaaaacac ctgaatcgaa tgagagagat    780
aactcaaaga aattttccaa gagctttgag ctcttgctaa ttttcctttc aaaatctcta    840
tatgattgtc cattctatag taattttaaa ggattggata ggattaatc ctttgattca    900
aagccatcca taagaacttt tcttacaaga ttaaaattct ccaaaattcc tatattttt    960
cctccaaatc aaaagacct taatagaggt tagctactat agttgatatc acgaaggttt   1020
tctcctgcca atttagtata agagttagtt accgattctt atcacggtta tcacgataac   1080
```

```
cacgcgggtt actcgaagaa aatcataata agactactaa gaaaaatcaa gatatattac    1140
ccacgagatt accaccgcaa tatgggcaat atggaaaata ttttctacct ctacgaacac    1200
agatccccat gcaaaacata gaggtaaaga agacagaatg ttgtagtagt actactcttt    1260
cccctttctt ttttgaaaaa aaaaagagaa cgggtcaagc tcaagaccaa tatcagcaac    1320
ttattccttt tgcacacttt caaagccccc actccactct cctctccttc ttccccttaa    1380
taacaacacc ggccattcct cctcctcgcc tcatccgcca ccacgtttg cttcgccaca     1440 cgcgcacaga aacacacaca cacagaaacc gaacgcgcgt cgatagaaat ggaggatgtg    1500
gcggcatcat tgcgccatgt actcgccaat gattgatcgc ctcattccct cctcctcctc    1560
ctcctcctcc tgaatccctc ctcatcgata accgaagcaa tggccagtgg caacagcagc    1620
agcagcagcg gcagcatggc tgccaccgcc ggaggtgtcg gcggctggct gggattctcg    1680
ctgtcgccgc acatggcgac gtactgcgcc ggcggcgtcg acgatgtcgg ccaccaccac    1740
caccaccacg tgcaccagca tcagcagcag catggaggtg ggctgttcta caaccctgcc    1800
gccgtcgcct cctccttcta ctacggcggc gggcatgacg ccgtcgtcac ctccgcggcc    1860
ggcggcggat cgtactatgg cgccgggttc tcctccatgc cgctcaagtc cgacggctcg    1920
ctctgcatca tggaggcact ccggggaggc gaccaagaac agcaaggtga gctagctagc    1980
ttaagtagta gctggataga gagatggcta gctcgtgctg gtgttcgtct agacagcgcg    2040
ggttcttctt acttgggctg tggctacagt tgcgttcatg gtcgctttgg cttgtagcaa    2100
atgcgtctct ttatgtcgct tggttggctt tgactcgtga ccaggggtgg tggtgtcggc    2160
gtcgcccaag ctggaggatt tcctaggcgc gggccccgcc atggcgctga gcctggacaa    2220
ctccgccttc tactacggcg gccacggtca ccaccaggga cacgcccagg acggcggcgc    2280
cgtcggtggc gacccgcacc acggcggcgg cggcttcctg cagtgcgctg tcatccccgg    2340
cgccggcgcc ggccacgacg cggcgctggt gcacgaccag tccgccgcgg cagtggcggc    2400
cggctgggcg gcgatgcacg gcggcggcta cgacatcgcc aacgccgccg ccgacgacgt    2460
ctgcgccgcc ggccccatca tccccaccgg cggccacctg cacccctctca ccctgtccat    2520 gagctcggcc gggtcccagt ccagctgcgt caccgtgcag gccgccgccg ccggcgagcc    2580
gtacatggcc atggacgccg tgagcaagaa gcgcggcggc gcggaccgcg ccgggcagaa    2640
gcagccggtg caccgcaagt ccattgacac gttcggccag aggacgtcgc agtacagagg    2700
cgtcaccagg tagtagctag cagcgccata gtgacagaca cctctcgcca ccatgccgcc    2760
atggcttcca ccttcacagc ttcacttaac ctcaagtaaa aaaaccttgt aaaaagcagg    2820
cataggtgga ctgggagata tgaggcacac ctctgggaca acagctgcaa gaaggaaggc    2880
cagaccagaa aaggacgcca aggttagaga aacttgacat tgtgattaat cacactttct    2940
tatgttttaa atgctgatga aatgtatatg tatgttcttg catgatcatc ctgctgaatc    3000
ttttggcatg ggctgcagtg tatcttggtg agtaccagta cacaagtact gggatgaat    3060 tgattagttt ttggaaacaa agatttgatt gtgagattgc aatgtaacct ttgctaggtg    3120
ggtatgacat ggaggagaag gctgccaggg cgtatgatct tgctgcgctc aagtactggg    3180
gcccttccac gcacatcaac ttcccggtga ttaaattacc aactctgatt agttcatttg    3240
ttgcttttct tgcaagcaaa cagtacacat tttagtttag atttagagt gctagctcaa     3300 gggcactgtg aatgactgta gttatgatgt tacggctatc attgacgttt gttttcacca    3360
ttttctgggc agttggagga ctaccaggag gagctggagg agatgaagaa catgagcagg    3420
caggagtatg tggctcacct cagaaggtac actgcgtagc tacctatgaa atcgccaagt    3480
```

-continued

```
cactgaacga acaagattgt gacactgaca tctgtaaacc tccatgtctg tttgctgcag     3540
gaaaagcagt ggcttctcgc gtggcgcttc gatctaccgt ggagtcacca ggtcgttgtt     3600
aatcacatgg ttgcagcaaa aatacggcaa atggatcttg aagcatgtt aactgagtga      3660 ttaacttggt gtgttttctg tcaatgtttg caggcatcat cagcacggga gatggcaggc     3720
gcgaatcggc cgcgtctcgg gcaacaagga cctttacttg gggacattca gtgagtgttc     3780
ttcctcccca atctctgcaa ctgcactatg atctactagt agttattctt gtccggattc     3840
ttctcatcat gtgatcgatc agcgatgagc agcaaagtgt gtatgaggtt ggctttgcag     3900
aggctgtcac ggtttaagga cgcagggtgt gtcctgtcac aatgatcata agaccttcag     3960
tcagctatgg ctagattcaa tgatgccaat tctgctgctt ctgcacggcc atggccacca     4020
ccatggccca gctcgaaaga atgtttcgcc ctgccgtttc ttgcatgctt ttgattgctg     4080
cagcagcggt gcttttgcgc atgcatgcat gcgcatgcat gcgcggttgg tttggtttgc     4140
cttttgttcg cttcctttcc aaaggctgtg cccctcgccg cagtcgcgtc ggcttttgcc     4200
gcggcgcggc gcgcgcgcca tgccggtttg acctgtgacc tgaccgcgcg cggcggcggc     4260
ggcgaaaact cggattttac ttttgattga tggtgagtga gttcgtcgtc gtgtgtgatt     4320
ggttgtattt gtggatgcag gcacgcagga ggaggcggcg gaggcgtacg acgtggcggc     4380
gatcaagttc cggggctca acgccgtcac caacttcgac atcacgaggt acgacgtgga     4440
caagatcctg gagagcagca cgctcctccc ggggagctg gcgcggcgca agggtaaggt     4500
cggcgacggc ggcggcgcgg cggcggtcgc cgacgccgcg gccgccttgg tgcaggccgg     4560
gaacgtggcg gagtggaaga tggccaccgc cgccgcgctg ccagcggcgg cgagaacgga     4620
gcagcagcag cagcatgggc acggcggcca ccaacaccat gacctcctgc cgagcgacgc     4680
cttctcggtg ctgcaggaca tcgtgtcgac cgtggacgcg gcgggcgcgc cgccgcgcgc     4740
gccgcacatg tcgatggcgg cgacgagcct gggcaactcc cgggagcaga gccctgacag     4800
gggcgtcggc ggcggcggcg gcggcggcgt cctcgccacg ctgttcgcca gcccgcggc     4860 ggcgtcgaag ctgtacagcc cggtgccgct gaacacctgg gcctcgccct cgccggcggt     4920
gagctcggtg ccggcgaggg ccggcgtgtc catcgcgcac ctgccaatgt tcgccgcgtg     4980
gaccgacgca tgagcagcaa agcatccttg tcgttaggcg aggtccatag ccactttagc     5040
ttaggaagct ggttagttag tggtagatga gcaagaatta gggtgaaatt cgcgatatgc     5100
atatgcgtgc gtttgcctcg ttcatcacct tctccagtag tagaagggtt tttgtaatat     5160
tggggcaatg caacagcagc agcatactag tagatcagca gatcctctat cacaggctca     5220
cagccacact tattggagtt ggttggtttt agtgttctca cttaacttca acaggaacaa     5280
cgtgttggtt ttgcaaagcc gaactcactg tggtggtgtt tatcatctca aagtaaattg     5340
aaagcacatt ctcgatcgaa cggcggccgt aaaccctcca gaggttcgga gaaaaatcct     5400
ccgaacccct gcatgacctt tcagcttct ctcgatcgga cggtacgtat gaaaccaagg      5460
gggttcggag aatgtcccgc tgcggctacg aacgaggatg ccccggtttt gccgaggcgg     5520
atcacgcatt cacgcgtgcc gtgaacgatc cgtccgcagc agcggcgcgc gttgtttccg     5580
ctggtctggt cggcgggcgt cgcggccgcc ggctggttag gccgagtggt cggagtggac     5640
ggggccgtga atcaggatt ggttaacggg ctaggcctct tggtgtcatg gcttgttca      5700 acaggtctag cgacggggct ccttgaacct tctgccttcg tttcgtcgcg ggcgtgtatg     5760
gtttttttgt gcgttttgaa actacacgaa gcatgccacg tcgtgccctg tgcagtcagt     5820
ctgtgctaac tgcttgtgca tcctccccta tcttataaaa aactaatata tgattagata     5880
```

-continued

```
tacaaattcg ttatattaga ttatatcaaa ttctatcata ggttagtttt ttttgacggg      5940
gagtacatta ctactcagtt gtaagtaccc ctattttgat tttgttctct atttatatag      6000
tctacttagg gttcgaaact tggcaacata tcctatgcac acaggccctc acgtgtacac      6060
acgtgcatac caactaaaaa atgtcaccaa aaaatctaga aaaaatcata cacatacttt      6120
cagttgtatt acacctaggg ttaaaatctt aacgtcaaat tcattatatt ttagccgtaa      6180
caaaaaaaac tgacagtttt aaggttacaa ttttgtcaga attttatctt ttttgttatt      6240
ctctatgtag aatgaatttg aagatgcgac tttgcatgta gatgtaatac tattgaaagt      6300
gcatgtatga attttctaa aatttttgt gataatttt agttggtgta cacggtgtgt         6360
acacgcgagg gcctatgtgc ataggatacg ctccctcgaa acttatatta agtactcaga      6420
cgtgtggtct tattgatcag ttaggtgtgt catcggtcgc cgcctcgccg cgcgtcacag      6480
aggacgtcgc cctctcatgt gttttcctac actactctct gacttgggaa ctcattccct      6540
ccgcacagcc atcctttgtg agatacgtcc agccatcttc tgagtgcaaa ttgacggatt      6600
agaatatgta aagtgtaaaa tgcttgccgg attcatgtgg attgaatgtt actgacttat      6660
ggacttcagt aaaccatgtc tttatgtggt tcttttctca tttacttagc aagaacagct      6720
gtgaccgtgc acattatcat gtatgttcat attatgaatt ggtggagtga aacttaaaaa      6780
agcttccttc tacctaaggt gattacgaga ttggcacatt ttgttgcctc cttgcatgca      6840
aattgtggta gaatgttttg attcatcagc ttagctaaca gaaccaattt tcttctcaaa      6900
catcttaatt gtgtttatcg tctcaacggt gagatgcata tatgggcatt acatgtgtta      6960
tacaggctgt gtttagttcc tgaaattggg gagaagttta gagaaagttg gtagtttgga      7020 aaaaagtta ggagccaact aaccatcgga tgtccgataa tattctaaag atcggatagc        7080
cctcctactg tgcttagctt acatattgac cgtgcatcat gcctaggttc taggttgtta      7140 acttatttg catacgtttta actattttat gttttaaact gtttatctga tccgcgatcc      7200
gattatatct ttttattcat tataattaaa tttttataaa aagatctcac atgatttttt      7260
tataatttaa tcacatgatg ttaactattg aaacatcgta taatatttac tgaaacatat      7320
gaataatact atgtgcaaca ttttaatta actagtaaat acttgtt                     7367
```

<210> SEQ ID NO 8
<211> LENGTH: 2010
<212> TYPE: DNA
<213> ORGANISM: Oryza sativa
<220> FEATURE:
<221> NAME/KEY: CDS
<222> LOCATION: (1)..(2010)
<223> OTHER INFORMATION:

<400> SEQUENCE: 8

```
atg gcc agt ggc aac agc agc agc agc ggc agc atg gct gcc acc           48
Met Ala Ser Gly Asn Ser Ser Ser Ser Gly Ser Met Ala Ala Thr
1               5                   10                  15 gcc gga ggt gtc ggc ggc tgg ctg gga ttc tcg ctg tcg ccg cac atg       96
Ala Gly Gly Val Gly Gly Trp Leu Gly Phe Ser Leu Ser Pro His Met
                20                  25                  30 gcg acg tac tgc gcc ggc ggc gtc gac gat gtc ggc cac cac cac cac       144
Ala Thr Tyr Cys Ala Gly Gly Val Asp Asp Val Gly His His His His
            35                  40                  45 cac cac gtg cac cag cat cag cag cag cat gga ggt ggg ctg ttc tac      192
His His Val His Gln His Gln Gln Gln His Gly Gly Gly Leu Phe Tyr
        50                  55                  60
```

```
aac cct gcc gcc gtc gcc tcc tcc ttc tac tac ggc ggc ggg cat gac    240
Asn Pro Ala Ala Val Ala Ser Ser Phe Tyr Tyr Gly Gly Gly His Asp
 65          70                  75                  80 gcc gtc gtc acc tcc gcg gcc ggc gga tcg tac tat ggc gcc ggg        288
Ala Val Val Thr Ser Ala Ala Gly Gly Gly Ser Tyr Tyr Gly Ala Gly
                 85                  90                  95 ttc tcc tcc atg ccg ctc aag tcc gac ggc tcg ctc tgc atc atg gag    336
Phe Ser Ser Met Pro Leu Lys Ser Asp Gly Ser Leu Cys Ile Met Glu
            100                 105                 110 gca ctc cgg gga ggc gac caa gaa cag caa ggg gtg gtg gtg tcg gcg    384
Ala Leu Arg Gly Gly Asp Gln Glu Gln Gln Gly Val Val Val Ser Ala
        115                 120                 125 tcg ccc aag ctg gag gat ttc cta ggc gcg ggc ccc gcc atg gcg ctg    432
Ser Pro Lys Leu Glu Asp Phe Leu Gly Ala Gly Pro Ala Met Ala Leu
130                 135                 140 agc ctg gac aac tcc gcc ttc tac tac ggc ggc cac ggt cac cac cag    480
Ser Leu Asp Asn Ser Ala Phe Tyr Tyr Gly Gly His Gly His His Gln
145                 150                 155                 160 gga cac gcc cag gac ggc ggc gcc gtc ggt ggc gac ccg cac cac ggc    528
Gly His Ala Gln Asp Gly Gly Ala Val Gly Gly Asp Pro His His Gly
                165                 170                 175 ggc ggc ggc ttc ctg cag tgc gct gtc atc ccc ggc gcc ggc gcc ggc    576
Gly Gly Gly Phe Leu Gln Cys Ala Val Ile Pro Gly Ala Gly Ala Gly
            180                 185                 190 cac gac gcg gcg ctg gtg cac gac cag tcc gcg gcg gca gtg gcg gcc    624
His Asp Ala Ala Leu Val His Asp Gln Ser Ala Ala Ala Val Ala Ala
        195                 200                 205 ggc tgg gcg gcg atg cac ggc ggc ggc tac gac atc gcc aac gcc gcc    672
Gly Trp Ala Ala Met His Gly Gly Gly Tyr Asp Ile Ala Asn Ala Ala
210                 215                 220 gcc gac gac gtc tgc gcc gcc ggc ccc atc atc ccc acc ggc ggc cac    720
Ala Asp Asp Val Cys Ala Ala Gly Pro Ile Ile Pro Thr Gly Gly His
225                 230                 235                 240 ctg cac cct ctc acc ctg tcc atg agc tcg gcc ggg tcc cag tcc agc    768
Leu His Pro Leu Thr Leu Ser Met Ser Ser Ala Gly Ser Gln Ser Ser
                245                 250                 255 tgc gtc acc gtg cag gcc gcc gcc gcc ggc gag ccg tac atg gcc atg    816
Cys Val Thr Val Gln Ala Ala Ala Ala Gly Glu Pro Tyr Met Ala Met
            260                 265                 270 gac gcc gtg agc aag aag cgc ggc ggc gcg gac cgc gcc ggg cag aag    864
Asp Ala Val Ser Lys Lys Arg Gly Gly Ala Asp Arg Ala Gly Gln Lys
        275                 280                 285 cag ccg gtg cac cgc aag tcc att gac acg ttc ggc cag agg acg tcg    912
Gln Pro Val His Arg Lys Ser Ile Asp Thr Phe Gly Gln Arg Thr Ser
290                 295                 300 cag tac aga ggc gtc acc agg cat agg tgg act ggg aga tat gag gca    960
Gln Tyr Arg Gly Val Thr Arg His Arg Trp Thr Gly Arg Tyr Glu Ala
305                 310                 315                 320 cac ctc tgg gac aac agc tgc aag aag gaa ggc cag acc aga aaa gga    1008
His Leu Trp Asp Asn Ser Cys Lys Lys Glu Gly Gln Thr Arg Lys Gly
                325                 330                 335 cgc caa gtg tat ctt ggt ggg tat gac atg gag gag aag gct gcc agg    1056
Arg Gln Val Tyr Leu Gly Gly Tyr Asp Met Glu Glu Lys Ala Ala Arg
            340                 345                 350 gcg tat gat ctt gct gcg ctc aag tac tgg ggc cct tcc acg cac atc    1104
Ala Tyr Asp Leu Ala Ala Leu Lys Tyr Trp Gly Pro Ser Thr His Ile
        355                 360                 365 aac ttc ccg ttg gag gac tac cag gag gag ctg gag gag atg aag aac    1152
Asn Phe Pro Leu Glu Asp Tyr Gln Glu Glu Leu Glu Glu Met Lys Asn
370                 375                 380
```

-continued

| | | |
|---|---|---|
| atg agc agg cag gag tat gtg gct cac ctc aga agg aaa agc agt ggc<br>Met Ser Arg Gln Glu Tyr Val Ala His Leu Arg Arg Lys Ser Ser Gly<br>385                     390                    395                    400 | | 1200 |
| ttc tcg cgt ggc gct tcg atc tac cgt gga gtc acc agg cat cat cag<br>Phe Ser Arg Gly Ala Ser Ile Tyr Arg Gly Val Thr Arg His His Gln<br>                    405                    410                    415 | | 1248 |
| cac ggg aga tgg cag gcg cga atc ggc cgc gtc tcg ggc aac aag gac<br>His Gly Arg Trp Gln Ala Arg Ile Gly Arg Val Ser Gly Asn Lys Asp<br>420                     425                    430 | | 1296 |
| ctt tac ttg ggg aca ttc atc gcg tcg gct ttt gcc gcg gcg cgg cgc<br>Leu Tyr Leu Gly Thr Phe Ile Ala Ser Ala Phe Ala Ala Ala Arg Arg<br>               435                    440                    445 | | 1344 |
| gcg cgc cat gcc ggc acg cag gag gag gcg gcg gag gcg tac gac gtg<br>Ala Arg His Ala Gly Thr Gln Glu Glu Ala Ala Glu Ala Tyr Asp Val<br>450                     455                    460 | | 1392 |
| gcg gcg atc aag ttc cgg ggg ctc aac gcc gtc acc aac ttc gac atc<br>Ala Ala Ile Lys Phe Arg Gly Leu Asn Ala Val Thr Asn Phe Asp Ile<br>465                     470                    475                    480 | | 1440 |
| acg agg tac gac gtg gac aag atc ctg gag agc agc acg ctc ctc ccg<br>Thr Arg Tyr Asp Val Asp Lys Ile Leu Glu Ser Ser Thr Leu Leu Pro<br>                    485                    490                    495 | | 1488 |
| ggg gag ctg gcg cgg cgc aag ggt aag gtc ggc gac ggc ggc ggc gcg<br>Gly Glu Leu Ala Arg Arg Lys Gly Lys Val Gly Asp Gly Gly Gly Ala<br>500                     505                    510 | | 1536 |
| gcg gcg gtc gcc gac gcc gcg gcc gcc ttg gtg cag gcc ggg aac gtg<br>Ala Ala Val Ala Asp Ala Ala Ala Ala Leu Val Gln Ala Gly Asn Val<br>515                     520                    525 | | 1584 |
| gcg gag tgg aag atg gcc acc gcc gcc gcg ctg cca gcg gcg gcg aga<br>Ala Glu Trp Lys Met Ala Thr Ala Ala Ala Leu Pro Ala Ala Ala Arg<br>530                     535                    540 | | 1632 |
| acg gag cag cag cag cag cat ggg cac ggc ggc cac caa cac cat gac<br>Thr Glu Gln Gln Gln Gln His Gly His Gly Gly His Gln His His Asp<br>545                     550                    555                    560 | | 1680 |
| ctc ctg ccg agc gac gcc ttc tcg gtg ctg cag gac atc gtg tcg acc<br>Leu Leu Pro Ser Asp Ala Phe Ser Val Leu Gln Asp Ile Val Ser Thr<br>               565                    570                    575 | | 1728 |
| gtg gac gcg gcg ggc gcg ccg ccg cgc gcg ccg cac atg tcg atg gcg<br>Val Asp Ala Ala Gly Ala Pro Pro Arg Ala Pro His Met Ser Met Ala<br>580                     585                    590 | | 1776 |
| gcg acg agc ctg ggc aac tcc cgg gag cag agc cct gac agg ggc gtc<br>Ala Thr Ser Leu Gly Asn Ser Arg Glu Gln Ser Pro Asp Arg Gly Val<br>595                     600                    605 | | 1824 |
| ggc ggc ggc ggc ggc ggc ggc gtc ctc gcc acg ctg ttc gcc aag ccc<br>Gly Gly Gly Gly Gly Gly Gly Val Leu Ala Thr Leu Phe Ala Lys Pro<br>610                     615                    620 | | 1872 |
| gcg gcg gcg tcg aag ctg tac agc ccg gtg ccg ctg aac acc tgg gcc<br>Ala Ala Ala Ser Lys Leu Tyr Ser Pro Val Pro Leu Asn Thr Trp Ala<br>625                     630                    635                    640 | | 1920 |
| tcg ccc tcg ccg gcg gtg agc tcg gtg ccg gcg agg gcc ggc gtg tcc<br>Ser Pro Ser Pro Ala Val Ser Ser Val Pro Ala Arg Ala Gly Val Ser<br>               645                    650                    655 | | 1968 |
| atc gcg cac ctg cca atg ttc gcc gcg tgg acc gac gca tga<br>Ile Ala His Leu Pro Met Phe Ala Ala Trp Thr Asp Ala<br>660                     665 | | 2010 |

<210> SEQ ID NO 9
<211> LENGTH: 669
<212> TYPE: PRT
<213> ORGANISM: Oryza sativa

<400> SEQUENCE: 9

```
Met Ala Ser Gly Asn Ser Ser Ser Gly Ser Met Ala Ala Thr
1               5                   10                  15

Ala Gly Gly Val Gly Gly Trp Leu Gly Phe Ser Leu Ser Pro His Met
                20                  25                  30

Ala Thr Tyr Cys Ala Gly Gly Val Asp Asp Val Gly His His His
            35                  40                  45

His His Val His Gln His Gln Gln His Gly Gly Leu Phe Tyr
        50                  55              60

Asn Pro Ala Ala Val Ala Ser Ser Phe Tyr Tyr Gly Gly Gly His Asp
65                  70                  75                  80

Ala Val Val Thr Ser Ala Ala Gly Gly Gly Ser Tyr Tyr Gly Ala Gly
                85                  90                  95

Phe Ser Ser Met Pro Leu Lys Ser Asp Gly Ser Leu Cys Ile Met Glu
                100                 105                 110

Ala Leu Arg Gly Gly Asp Gln Glu Gln Gln Gly Val Val Val Ser Ala
            115                 120                 125

Ser Pro Lys Leu Glu Asp Phe Leu Gly Ala Gly Pro Ala Met Ala Leu
130                 135                 140

Ser Leu Asp Asn Ser Ala Phe Tyr Tyr Gly Gly His Gly His His Gln
145                 150                 155                 160

Gly His Ala Gln Asp Gly Gly Ala Val Gly Gly Asp Pro His His Gly
                165                 170                 175

Gly Gly Gly Phe Leu Gln Cys Ala Val Ile Pro Gly Ala Gly Ala Gly
                180                 185                 190

His Asp Ala Ala Leu Val His Asp Gln Ser Ala Ala Val Ala Ala
            195                 200                 205

Gly Trp Ala Ala Met His Gly Gly Gly Tyr Asp Ile Ala Asn Ala Ala
            210                 215                 220

Ala Asp Asp Val Cys Ala Ala Gly Pro Ile Ile Pro Thr Gly Gly His
225                 230                 235                 240

Leu His Pro Leu Thr Leu Ser Met Ser Ser Ala Gly Ser Gln Ser Ser
                245                 250                 255

Cys Val Thr Val Gln Ala Ala Ala Gly Glu Pro Tyr Met Ala Met
            260                 265                 270

Asp Ala Val Ser Lys Lys Arg Gly Gly Ala Asp Arg Ala Gly Gln Lys
                275                 280                 285

Gln Pro Val His Arg Lys Ser Ile Asp Thr Phe Gly Gln Arg Thr Ser
            290                 295                 300

Gln Tyr Arg Gly Val Thr Arg His Arg Trp Thr Gly Arg Tyr Glu Ala
305                 310                 315                 320

His Leu Trp Asp Asn Ser Cys Lys Lys Glu Gly Gln Thr Arg Lys Gly
                325                 330                 335

Arg Gln Val Tyr Leu Gly Gly Tyr Asp Met Glu Lys Ala Ala Arg
            340                 345                 350

Ala Tyr Asp Leu Ala Ala Leu Lys Tyr Trp Gly Pro Ser Thr His Ile
            355                 360                 365

Asn Phe Pro Leu Glu Asp Tyr Gln Glu Glu Leu Glu Glu Met Lys Asn
370                 375                 380

Met Ser Arg Gln Glu Tyr Val Ala His Leu Arg Arg Lys Ser Ser Gly
385                 390                 395                 400

Phe Ser Arg Gly Ala Ser Ile Tyr Arg Gly Val Thr Arg His His Gln
                405                 410                 415
```

```
His Gly Arg Trp Gln Ala Arg Ile Gly Arg Val Ser Gly Asn Lys Asp
            420                 425                 430

Leu Tyr Leu Gly Thr Phe Ile Ala Ser Ala Phe Ala Ala Ala Arg Arg
            435                 440                 445

Ala Arg His Ala Gly Thr Gln Glu Glu Ala Ala Glu Ala Tyr Asp Val
            450                 455                 460

Ala Ala Ile Lys Phe Arg Gly Leu Asn Ala Val Thr Asn Phe Asp Ile
465                 470                 475                 480

Thr Arg Tyr Asp Val Asp Lys Ile Leu Glu Ser Ser Thr Leu Leu Pro
                485                 490                 495

Gly Glu Leu Ala Arg Arg Lys Gly Lys Val Gly Asp Gly Gly Gly Ala
            500                 505                 510

Ala Ala Val Ala Asp Ala Ala Ala Leu Val Gln Ala Gly Asn Val
            515                 520                 525

Ala Glu Trp Lys Met Ala Thr Ala Ala Leu Pro Ala Ala Ala Arg
            530                 535                 540

Thr Glu Gln Gln Gln Gln His Gly His Gly Gly His Gln His His Asp
545                 550                 555                 560

Leu Leu Pro Ser Asp Ala Phe Ser Val Leu Gln Asp Ile Val Ser Thr
                565                 570                 575

Val Asp Ala Ala Gly Ala Pro Pro Arg Ala Pro His Met Ser Met Ala
            580                 585                 590

Ala Thr Ser Leu Gly Asn Ser Arg Glu Gln Ser Pro Asp Arg Gly Val
            595                 600                 605

Gly Gly Gly Gly Gly Gly Val Leu Ala Thr Leu Phe Ala Lys Pro
            610                 615                 620

Ala Ala Ala Ser Lys Leu Tyr Ser Pro Val Pro Leu Asn Thr Trp Ala
625                 630                 635                 640

Ser Pro Ser Pro Ala Val Ser Ser Val Pro Ala Arg Ala Gly Val Ser
                645                 650                 655

Ile Ala His Leu Pro Met Phe Ala Ala Trp Thr Asp Ala
            660                 665

<210> SEQ ID NO 10
<211> LENGTH: 1137
<212> TYPE: DNA
<213> ORGANISM: Gossypium hirsutum

<400> SEQUENCE: 10
ctgagaagga aaagcagcgg cttctcgcgc ggcgcttcga tctaccgggg agtcaccagg        60
catcaccagc acgggcggtg gcaggcgcgc atcggccgcg tctcgggcaa caaggacctc       120
tacctgggaa cgttcagcac gcaggaggag ccgcgcgagg cgtacgacgt ggccgcgatc       180
aagttccgcg gcctcagcgc ggtcaccaac ttcgacatca gcggtacga cgtggacaag       240 atcatggaga gcagcacgct gctcccgggc gagcaggtcc ggcgcaggaa ggaaggcgcc       300
gacgccgcgg tctcggaggc cgccgccgcg ctggtgcagg ccggcaactg catgacggac       360
acctggaaga tccaggcggc tctgccagct gccgcgcggg ccgacgagcg cggcgccggc       420
cagcagcagc gccaggactt gctgtcgagc gaggccttct cgctgctcca cgacatcgtg       480
tccgtcgacg ctgctgctgg tacagggaca gggacagggg gcatgtcgaa cgcgtcgtcg       540
tcgctggccc ccagcgtgag caactcccgg gagcagagcc cggaccgggg cggcgccagc       600
ctcgccatgc tcttcgccaa gccgtcgcgc gcgcccaagc tggcttgccc gctgccgctg       660
gggtcgtggg tgtcgccgtc cgcggtgtcc gccaggccgc ccggcgtgtc aatcgcgcac       720
```

```
ctgccggtgt cgccgcgtg gaccgacgca tgaacaaaca tccgtgtcat taccagggta    780
tggttctttt ggtttgctta gagcgtgctt tttagctggg taaggttagc tgcgtagcgg    840
tgatctgatc agcatatgtg agaggaacta gccatgcgtg tctgctttgt cctcctgcga    900
ttcctcctcc agttgcgttg cgaggaggtt tcttttgta ataccggggc tagatagcac    960
agcatggatc tcctcctgta gccaacacta atttggagta ggatggttag tgttgatctc   1020
ctaacttcaa ttaggaaaaa tatgccaagt aagataagtt taaacctgtg cgctttgcaa   1080
ttcatcaatg agctgggatt cagacctcaa aaaaaaaaaa aaaaaaaaaa aaaaaaa     1137
```

<210> SEQ ID NO 11
<211> LENGTH: 585
<212> TYPE: PRT
<213> ORGANISM: Gossypium hirsutum

<400> SEQUENCE: 11

```
Met Ser Asn Trp Leu Gly Phe Ser Leu Thr Pro Asp Leu Arg Ile Asp
1               5                   10                  15

Glu Ser Phe Gly Arg Glu Asp His Gly Gly Phe Pro Ser Val Met Pro
            20                  25                  30

Leu Arg Ser Asp Gly Ser Leu Cys Val Val Asp Pro Phe Arg Arg Ser
        35                  40                  45

Ser Ile Ala Ala Asp Glu Asp Trp Arg Tyr Glu Asn Gly Ile Gly Ser
    50                  55                  60

Ala Thr Ala Asn Glu Gln Gly Pro Lys Leu Glu Asp Phe Leu Gly Cys
65                  70                  75                  80

Tyr Ser Asn Ser Pro Ser Gln Glu Thr Lys Ala Tyr Cys Gly Thr His
                85                  90                  95

Glu Asn Gln Asn Thr Val Pro Ser Pro Thr Arg Ile Asn Val Asn Val
            100                 105                 110

Ala Pro Asn Tyr Ser Ser Ser Gly Asp Ala Glu Ala Ala Glu Asn Phe
        115                 120                 125

Thr Asn Pro Ser Ser Phe Ile Gln Thr Tyr Arg Asn Tyr Asn Glu Asn
    130                 135                 140

Pro Gln Thr Leu Met Ala Gly Gly His Ser Leu Gln Gln Cys Asp Pro
145                 150                 155                 160

Asn Pro Asn His Asn Gln Arg Ser Gly Val His His Val Pro Phe Glu
                165                 170                 175

Ser Ala Thr Ser Val Ser Gly Phe Lys Ser Trp Leu Arg Gln Thr Pro
            180                 185                 190

Phe Pro Gly Gly Lys Ala Ser Gly Asn Glu Thr Asn Asn Asn Phe Asn
        195                 200                 205

Phe Gln Ala Leu Ser Leu Thr Met Ser Pro Thr Ser Arg Asn Gly Phe
    210                 215                 220

Pro Ala Ile Ala Pro Leu Glu Val Val Asp Asn Arg Lys Arg Pro Val
225                 230                 235                 240

Gly Lys Asn Leu Thr Arg Glu Ser Val Pro Arg Lys Ser Ile Asp Thr
                245                 250                 255

Phe Gly Gln Arg Thr Ser Gln Tyr Arg Gly Val Thr Arg His Arg Trp
            260                 265                 270

Thr Gly Arg Tyr Glu Ala His Leu Trp Asp Asn Ser Cys Arg Lys Glu
        275                 280                 285

Gly Gln Thr Arg Lys Gly Arg Gln Val Tyr Leu Gly Gly Tyr Asp Lys
    290                 295                 300
```

-continued

```
Glu Lys Ala Ala Lys Ala Tyr Asp Leu Ala Ala Leu Lys Tyr Trp
305                 310                 315                 320

Gly Pro Thr Thr His Ile Asn Phe Pro Leu Ser Thr Tyr Glu Lys Glu
                325                 330                 335

Leu Glu Glu Met Lys Asn Met Thr Arg Gln Glu Phe Val Ala His Leu
            340                 345                 350

Arg Arg Lys Ser Ser Gly Phe Ser Arg Gly Ala Ser Val Tyr Arg Gly
        355                 360                 365

Val Thr Arg His His Gln His Gly Arg Trp Gln Ala Arg Ile Gly Arg
370                 375                 380

Val Ala Gly Asn Lys Asp Leu Tyr Leu Gly Thr Phe Ser Thr Gln Glu
385                 390                 395                 400

Glu Ala Ala Glu Ala Tyr Asp Ile Ala Ala Ile Lys Phe Arg Gly Thr
                405                 410                 415

Ser Ala Val Thr Asn Phe Asp Ile Ser Arg Tyr Asp Val Lys Arg Ile
                420                 425                 430

Cys Ser Ser Ser Thr Leu Ile Gly Gly Glu Leu Ala Lys Arg Ser Pro
        435                 440                 445

Lys Asp Thr Ala Ser Ile Ala Pro Glu Asp Tyr Asn Ser Cys Ala Ser
    450                 455                 460

Ser Ala Ser Pro Gln Pro Leu Leu Ala Ile Pro Ser Gly Glu Ala Ser
465                 470                 475                 480

Asp Glu Leu Ala Asp Met Val Trp Thr Ala Asn Ser Asp Glu Gln Gln
                485                 490                 495

Gln His Gln Ser Thr Asn Thr Asn Asn Asp Ala Ser Leu Ala Asn Ser
                500                 505                 510

Ser Ser Arg Asn Ser Ser Asn Pro Gln Ser Pro Lys Gly Ser Ile Gly
        515                 520                 525

Leu Ala Ser Asp Lys Phe Gly Ile Gly Gly Asp Tyr Ser His His Gly
    530                 535                 540

Tyr Phe Ser Leu Lys Gly Ser Lys Tyr Glu Asp Gly Asn Ser Glu Thr
545                 550                 555                 560

Asp Asn Ser Asn Glu Asn Arg Leu Gly Asn Leu Gly Leu Val His Lys
                565                 570                 575

Ile Pro Met Phe Ala Leu Trp Asn Glu
            580                 585

<210> SEQ ID NO 12
<211> LENGTH: 1137
<212> TYPE: DNA
<213> ORGANISM: Zea mays

<400> SEQUENCE: 12
ctgagaagga aaagcagcgg cttctcgcgc ggcgcttcga tctaccgggg agtcaccagg      60
catcaccagc acgggcggtg gcaggcgcgc atcggccgcg tctcgggcaa caaggacctc     120
tacctgggaa cgttcagcac gcaggaggag ccgcggagg cgtacgacgt ggccgcgatc     180
aagttccgcg gcctcagcgc ggtcaccaac ttcgacatca cgcggtacga cgtggacaag     240
atcatggaga gcagcacgct gctcccgggc gagcaggtcc ggcgcaggaa ggaaggcgcc     300
gacgccgcgc tctcggaggc cgccgccgcg ctggtgcagg ccggcaactg catgacggac     360
acctggaaga tccaggcggc tctgccagct gccgcgcggg ccgacgagcg cggcgccggc     420
cagcagcagc gccaggactt gctgtcgagc gaggccttct cgctgctcca cgacatcgtg     480
tccgtcgacg ctgctgctgg tacagggaca gggacagggg gcatgtcgaa cgcgtcgtcg     540
```

-continued

```
tcgctggccc ccagcgtgag caactcccgg gagcagagcc cggaccgggg cggcgccagc    600
ctcgccatgc tcttcgccaa gcccgtcgcg gcgcccaagc tggcttgccc gctgccgctg    660
gggtcgtggg tgtcgccgtc cgcggtgtcc gccaggccgc ccggcgtgtc aatcgcgcac    720
ctgccggtgt tcgccgcgtg gaccgacgca tgaacaaaca tccgtgtcat taccagggta    780
tggttctttt ggtttgctta gagcgtgctt tttagctggg taaggttagc tgcgtagcgg    840
tgatctgatc agcatatgtg agaggaacta gccatgcgtg tctgctttgt cctcctgcga    900
ttcctcctcc agttgcgttg cgaggaggtt ctttttgta ataccggggc tagatagcac    960
agcatggatc tcctcctgta gccaacacta atttggagta ggatggttag tgttgatctc    1020
ctaacttcaa ttaggaaaaa tatgccaagt aagataagtt taaacctgtg cgctttgcaa    1080
ttcatcaatg agctgggatt cagacctcaa aaaaaaaaa aaaaaaaaaa aaaaaaa       1137
```

<210> SEQ ID NO 13
<211> LENGTH: 255
<212> TYPE: PRT
<213> ORGANISM: Zea mays

<400> SEQUENCE: 13

```
Arg Pro Thr Arg Pro Leu Arg Arg Lys Ser Ser Gly Phe Ser Arg Gly
1               5                   10                  15

Ala Ser Ile Tyr Arg Gly Val Thr Arg His His Gln His Gly Arg Trp
            20                  25                  30

Gln Ala Arg Ile Gly Arg Val Ser Gly Asn Lys Asp Leu Tyr Leu Gly
        35                  40                  45

Thr Phe Ser Thr Gln Glu Glu Ala Ala Glu Ala Tyr Asp Val Ala Ala
    50                  55                  60

Ile Lys Phe Arg Gly Leu Ser Ala Val Thr Asn Phe Asp Ile Thr Arg
65                  70                  75                  80

Tyr Asp Val Asp Lys Ile Met Glu Ser Ser Thr Leu Leu Pro Gly Glu
                85                  90                  95

Gln Val Arg Arg Lys Glu Gly Ala Asp Ala Ala Val Ser Glu Ala
            100                 105                 110

Ala Ala Leu Val Gln Ala Gly Asn Cys Met Thr Asp Thr Trp Lys
        115                 120                 125

Ile Gln Ala Ala Leu Pro Ala Ala Arg Ala Asp Glu Arg Gly Ala
    130                 135                 140

Gly Gln Gln Gln Arg Gln Asp Leu Leu Ser Ser Glu Ala Phe Ser Leu
145                 150                 155                 160

Leu His Asp Ile Val Ser Val Asp Ala Ala Ala Gly Thr Gly Thr Gly
                165                 170                 175

Thr Gly Gly Met Ser Asn Ala Ser Ser Ser Leu Ala Pro Ser Val Ser
            180                 185                 190

Asn Ser Arg Glu Gln Ser Pro Asp Arg Gly Gly Ala Ser Leu Ala Met
        195                 200                 205

Leu Phe Ala Lys Pro Val Ala Ala Pro Lys Leu Ala Cys Pro Leu Pro
    210                 215                 220

Leu Gly Ser Trp Val Ser Pro Ser Ala Val Ser Ala Arg Pro Gly
225                 230                 235                 240

Val Ser Ile Ala His Leu Pro Val Phe Ala Ala Trp Thr Asp Ala
                245                 250                 255
```

```
<210> SEQ ID NO 14
<211> LENGTH: 34
<212> TYPE: DNA
<213> ORGANISM: Artificial Sequence
<220> FEATURE:
<223> OTHER INFORMATION: see misc features
<221> NAME/KEY: misc_feature
<222> LOCATION: (1)..(12)
<223> OTHER INFORMATION: Arabidopsis thalania with EcoRI linker at 5'
      end, linker encomapsses nucleotides 1-12

<400> SEQUENCE: 14
cgcggcgaat tcatgaagtc tttttgtgat aatg                               34

<210> SEQ ID NO 15
<211> LENGTH: 29
<212> TYPE: DNA
<213> ORGANISM: Artificial Sequence
<220> FEATURE:
<223> OTHER INFORMATION: see misc features
<221> NAME/KEY: misc_feature
<222> LOCATION: (1)..(12)
<223> OTHER INFORMATION: Arabidopsis thalania with SalI linker at 5'
      end - linker encompasses nucleotides 1-12

<400> SEQUENCE: 15
cgcggcgtcg acgaatcagc ccaagcagc                                     29

<210> SEQ ID NO 16
<211> LENGTH: 31
<212> TYPE: DNA
<213> ORGANISM: Glycine max

<400> SEQUENCE: 16
cgcggcccat ggatgaagcg cataaatgag a                                  31

<210> SEQ ID NO 17
<211> LENGTH: 31
<212> TYPE: DNA
<213> ORGANISM: Artificial Sequence
<220> FEATURE:
<223> OTHER INFORMATION: see misc features
<221> NAME/KEY: misc_feature
<222> LOCATION: (1)..(12)
<223> OTHER INFORMATION: Glycine max with XhoI linker at 5' end - linker
      encompasses nucleotides 1-12

<400> SEQUENCE: 17
cgcggcctcg aggtatcagt ccaagaagca a                                  31

<210> SEQ ID NO 18
<211> LENGTH: 35
<212> TYPE: DNA
<213> ORGANISM: Glycine max

<400> SEQUENCE: 18
cgcggcccat ggaatgaaga gtatggaaaa tgatg                              35

<210> SEQ ID NO 19
<211> LENGTH: 30
<212> TYPE: DNA
<213> ORGANISM: Artificial Sequence
<220> FEATURE:
<221> NAME/KEY: misc_feature
<222> LOCATION: (1)..(12)
<223> OTHER INFORMATION: - Glycine max with 5' XhoI linker - linker
      encompasses nucleotides 1-12
```

```
-continued

<400> SEQUENCE: 19
cgcggcctcg aggcatctgt ccaagctgca                                          30

<210> SEQ ID NO 20
<211> LENGTH: 22
<212> TYPE: DNA
<213> ORGANISM: Pisum sativum Rubisco small subunit termination region

<400> SEQUENCE: 20
caacgttcgt caagttcaat gc                                                  22

<210> SEQ ID NO 21
<211> LENGTH: 26
<212> TYPE: DNA
<213> ORGANISM: Pisum sativum Rubisco small subunit termination region

<400> SEQUENCE: 21
tgccataata ctcgaactca gtagga                                              26

<210> SEQ ID NO 22
<211> LENGTH: 26
<212> TYPE: DNA
<213> ORGANISM: Pisum sativum Rubisco small subunit termination region

<400> SEQUENCE: 22
tcagtttcat tgcgcacaca ccagaa                                              26

<210> SEQ ID NO 23
<211> LENGTH: 20
<212> TYPE: DNA
<213> ORGANISM: Oryza sativa

<400> SEQUENCE: 23
gagcgtgtgc atggttggtg                                                     20

<210> SEQ ID NO 24
<211> LENGTH: 29
<212> TYPE: DNA
<213> ORGANISM: Oryza sativa

<400> SEQUENCE: 24
ctcgaggcat ctgtccaggc tgcaaaaac                                           29

<210> SEQ ID NO 25
<211> LENGTH: 6
<212> TYPE: PRT
<213> ORGANISM: Artificial Sequence
<220> FEATURE:
<223> OTHER INFORMATION: see misc features
<221> NAME/KEY: MISC_FEATURE
<222> LOCATION: (1)..(1)
<223> OTHER INFORMATION: X = Gly, Ala, Val, Leu, or Ile

<400> SEQUENCE: 25

Xaa Ser Ser Ser Arg Glu
1               5

<210> SEQ ID NO 26
<211> LENGTH: 6
<212> TYPE: PRT
<213> ORGANISM: Artificial Sequence
<220> FEATURE:
<223> OTHER INFORMATION: see misc features
```

```
<221> NAME/KEY: MISC_FEATURE
<222> LOCATION: (1)..(1)
<223> OTHER INFORMATION: X = Gly, Ala, Val, Leu, or Ile

<400> SEQUENCE: 26

Xaa Ser Asn Ser Arg Glu
1               5

<210> SEQ ID NO 27
<211> LENGTH: 6
<212> TYPE: PRT
<213> ORGANISM: Artificial Sequence
<220> FEATURE:
<223> OTHER INFORMATION: see misc features

<400> SEQUENCE: 27

Asn Ser Ser Ser Arg Asn
1               5

<210> SEQ ID NO 28
<211> LENGTH: 12
<212> TYPE: PRT
<213> ORGANISM: Artificial Sequence
<220> FEATURE:
<223> OTHER INFORMATION: see misc features
<221> NAME/KEY: MISC_FEATURE
<222> LOCATION: (7)..(7)
<223> OTHER INFORMATION: X = Gly, Ala, Val, Leu, or Ile
<221> NAME/KEY: MISC_FEATURE
<222> LOCATION: (4)..(4)
<223> OTHER INFORMATION: X = Gly, Ala, Val, Leu, or Ile

<400> SEQUENCE: 28

Ser Ser Leu Xaa Thr Ser Xaa Ser Ser Ser Arg Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: see misc features
<221> NAME/KEY: MISC_FEATURE
<222> LOCATION: (4)..(4)
<223> OTHER INFORMATION: X = Gly, Ala, Val, Leu, and Ile.
<221> NAME/KEY: MISC_FEATURE
<222> LOCATION: (7)..(7)
<223> OTHER INFORMATION: X = Gly, Ala, Val, Leu, and Ile.

<400> SEQUENCE: 29

Ser Ser Leu Xaa Pro Ser Xaa Ser Asn Ser Arg Glu
1               5                   10

<210> SEQ ID NO 30
<211> LENGTH: 12
<212> TYPE: PRT
<213> ORGANISM: Artificial sequence
<220> FEATURE:
<223> OTHER INFORMATION: see misc features
<221> NAME/KEY: MISC_FEATURE
<222> LOCATION: (1)..(11)
<223> OTHER INFORMATION: X = Gly, Ala, Val, Leu, or Ile
<221> NAME/KEY: MISC_FEATURE
<222> LOCATION: (1)..(11)
<223> OTHER INFORMATION: Xaa = Gly, Ala, Val, Leu, or Ile
```

```
<400> SEQUENCE: 30

Ser Ser Leu Xaa Thr Ser Xaa Ser Asn Ser Arg Glu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: see misc features
<221> NAME/KEY: MISC_FEATURE
<222> LOCATION: (3)..(3)
<223> OTHER INFORMATION: X= Gly, Ala, Val, Leu, or Ile

<400> SEQUENCE: 31

Ser Leu Xaa Asn Ser Ser Ser Arg Asn
1               5

<210> SEQ ID NO 32
<211> LENGTH: 31
<212> TYPE: DNA
<213> ORGANISM: Artificial Sequence
<220> FEATURE:
<223> OTHER INFORMATION: see misc features
<221> NAME/KEY: misc_feature
<222> LOCATION: (1)..(8)
<223> OTHER INFORMATION: AscI restriction enzyme site

<400> SEQUENCE: 32
ggcgcgccac aatggccagc ggcggcggca g                           31

<210> SEQ ID NO 33
<211> LENGTH: 31
<212> TYPE: DNA
<213> ORGANISM: Artificial Sequence
<220> FEATURE:
<223> OTHER INFORMATION: see misc features
<221> NAME/KEY: misc_feature
<222> LOCATION: (1)..(8)
<223> OTHER INFORMATION: Sse8387I restriction site

<400> SEQUENCE: 33
cctgcaggtc aggcatctgt ccaggctgca a                           31
```